US011787795B2

(12) United States Patent
Choudhary et al.

(10) Patent No.: US 11,787,795 B2
(45) Date of Patent: Oct. 17, 2023

(54) INHIBITORS OF RNA GUIDED NUCLEASES AND USES THEREOF

(71) Applicants: PRESIDENT AND FELLOWS OF HARVARD COLLEGE, Cambridge, MA (US); THE BRIGHAM AND WOMEN'S HOSPITAL, INC., Boston, MA (US); THE REGENTS OF THE UNIVERSITY OF CALIFORNIA, Oakland, CA (US)

(72) Inventors: Amit Choudhary, Cambridge, MA (US); Peng Wu, Boston, MA (US); Basudeb Maji, Boston, MA (US); Elisa Franco, Oakland, CA (US); Hari K. K. Subramanian, Oakland, CA (US)

(73) Assignees: PRESIDENT AND FELLOWS OF HARVARD COLLEGE, Cambridge, MA (US); THE BRIGHAM AND WOMEN'S HOSPITAL, INC., Boston, MA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1200 days.

(21) Appl. No.: 16/346,392

(22) PCT Filed: Oct. 31, 2017

(86) PCT No.: PCT/US2017/059365
§ 371 (c)(1),
(2) Date: Apr. 30, 2019

(87) PCT Pub. No.: WO2018/085288
PCT Pub. Date: May 11, 2018

(65) Prior Publication Data
US 2019/0263807 A1    Aug. 29, 2019

Related U.S. Application Data

(60) Provisional application No. 62/416,017, filed on Nov. 1, 2016.

(51) Int. Cl.
| *C12N 9/22* | (2006.01) |
| *C12Q 1/6837* | (2018.01) |
| *G01N 33/58* | (2006.01) |
| *C07D 471/04* | (2006.01) |
| *C07D 487/10* | (2006.01) |
| *C07D 493/04* | (2006.01) |
| *C07D 471/20* | (2006.01) |
| *C07C 291/00* | (2006.01) |

(52) U.S. Cl.
CPC .......... *C07D 471/04* (2013.01); *C07C 291/00* (2013.01); *C07D 471/20* (2013.01); *C07D 487/10* (2013.01); *C07D 493/04* (2013.01); *C12N 9/22* (2013.01); *C12Q 1/6837* (2013.01); *G01N 33/582* (2013.01)

(58) Field of Classification Search
CPC ...... C07D 471/04; C12N 9/22; C12Q 1/6837; G01N 33/582
See application file for complete search history.

(56) References Cited

U.S. PATENT DOCUMENTS
2009/0275568 A1   11/2009 Kajino et al.

FOREIGN PATENT DOCUMENTS
WO    2016022363 A2    2/2016

OTHER PUBLICATIONS

Maji et al., "A High-Throughput Platform to Identify Small-Molecule Inhibitors of CRISPR-Cas9," Cell, May 2, 2019, vol. 177, No. 4, pp. 1067-1079.e19.
International Search Report and Written Opinion for corresponding PCT patent application PCT/US17/59365, dated Mar. 12, 2018 (16 pages).
Comer et al., "Fragment-based domain shuffling approach for the synthesis of pyran-based macrocycles," Proceedings of the National Academy of Sciences of the United States of America, Apr. 26, 2011, vol. 108, No. 17, pp. 6751-6756.
Davis et al., "Small Molecule-Triggered Cas9 Protein with Improved Genome-Editing Specificity," Nature Chemical Biology, May 2015, vol. 11, No. 5, pp. 316-318.
Fu et al., "High-frequency off-target mutagenesis induced by CRISPR-Cas nucleases in human cells," Nature Biotechnology, Sep. 2013, vol. 31, No. 9, pp. 822-826.
Gonzalez et al., "An iCRISPR Platform for Rapid, Multiplexable, and Inducible Genome Editing in Human Pluripotent Stem Cells," Cell Stem Cell, Aug. 7, 2014, vol. 15, No. 2, pp. 215-226.
Heler et al., "Cas9 specifies functional viral targets during CRISPR-Cas adaptation," Nature, Mar. 12, 2015, vol. 519, No. 7542, pp. 199-202.
Kim et al., "Genome-wide analysis reveals specificities of Cpf1 endonucleases in human cells," Nature Biotechnology, Aug. 2016, vol. 34, No. 8, pp. 863-868.
Kleinstiver et al., "Engineered CRISPR-Cas9 nucleases with altered PAM specificities," Nature, Jul. 23, 2015, vol. 523, No. 7561, pp. 481-485.
Lowe et al., "Synthesis and Profiling of a Diverse Collection of Azetidine-Based Scaffolds for the Development of CNS-Focused Lead-Like Libraries," The Journal of Organic Chemistry, Sep. 7, 2012, vol. 77, No. 17, pp. 7187-7211.
Marcaurelle et al., "An Aldol-Based Build/Couple/Pair Strategy for the Synthesis of Medium- and Large-Sized Rings: Discovery of Macrocyclic Histone Deacetylase Inhibitors," Journal of the American Chemical Society, Dec. 1, 2010, vol. 132, No. 47, pp. 16962-16976.

(Continued)

*Primary Examiner* — Alicia L Otton
(74) *Attorney, Agent, or Firm* — Melissa Hunter-Ensor; Scott Goncher; Greenberg Traurig, LLP

(57) ABSTRACT

Compositions and methods are provided for the inhibition of the function of RNA guided endonucleases, including the identification and use of such inhibitors.

3 Claims, 22 Drawing Sheets

Specification includes a Sequence Listing.

(56) References Cited

OTHER PUBLICATIONS

Nunez et al., "Integrase-mediated spacer acquisition during CRISPR-Cas adaptive immunity," Nature, Mar. 12, 2015, vol. 519, No. 7542, pp. 193-198.

Richardson et al., "Enhancing homology-directed genome editing by catalytically active and inactive CRISPR-Cas9 using asymmetric donor DNA," Nature Biotechnology, Mar. 2016, vol. 34, No. 3, pp. 339-344.

Schreiber et al., "Towards patient-based cancer therapeutics," Nature Biotechnology, Sep. 2010, vol. 28, No. 9, pp. 904-906.

Schreiber, Stuart L., "Target-Oriented and Diversity-Oriented Organic Synthesis in Drug Discovery," Science, Mar. 17, 2000, vol. 287, No. 5460, pp. 1964-1969.

Senis et al., "CRISPR/Cas9-mediated genome engineering: An adeno-associated viral (AAV) vector toolbox," Biotechnology Journal, 2014, vol. 9, No. 11, pp. 1402-1412.

Wawer et al., "Toward performance-diverse small-molecule libraries for cell-based phenotypic screening using multiplexed high-dimensional profiling," Proceedings of the National Academy of Sciences of the United States of America, Jul. 29, 2014, vol. 111, No. 30, pp. 10911-10916.

Wright et al., "Rational design of a split-Cas9 enzyme complex," Proceedings of the National Academy of Sciences of the United State of America, Mar. 10, 2015, vol. 112, No. 10, pp. 2984-2989.

Zetsche et al., "A Split-Cas9 Architecture for Inducible Genome Editing and Transcription Modulation," Nature Biotechnology, Feb. 2015, vol. 33, No. 2, pp. 139-142.

FIG. 2A
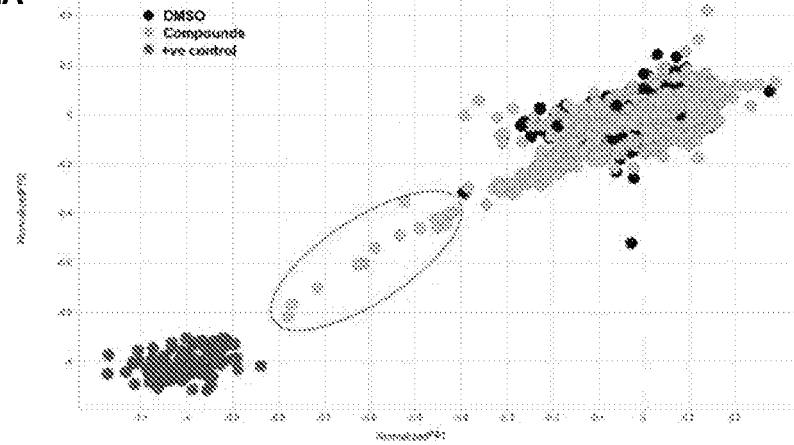
FIG. 2B
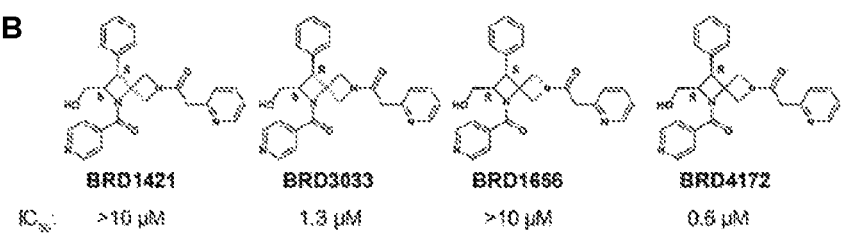
FIG. 2C
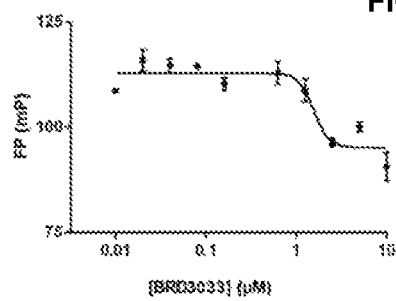
FIG. 2D
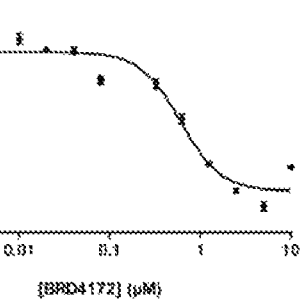
FIG. 2E
FIG. 2F
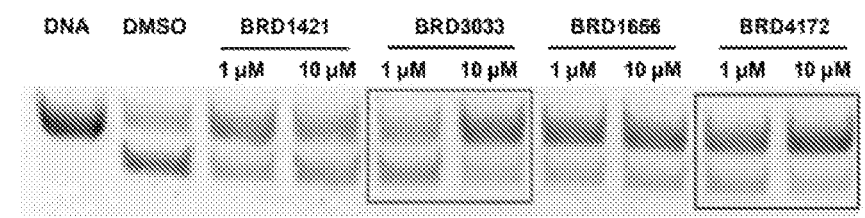

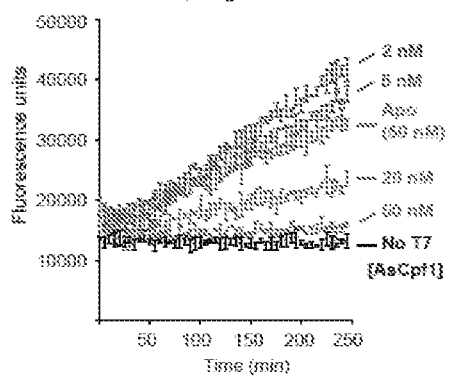
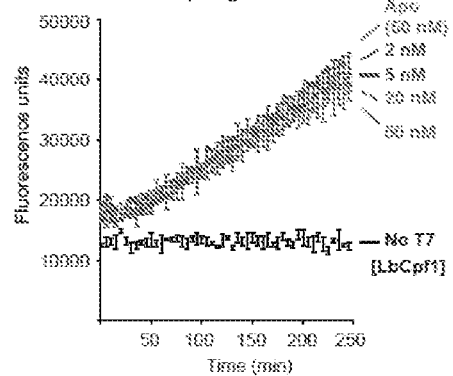

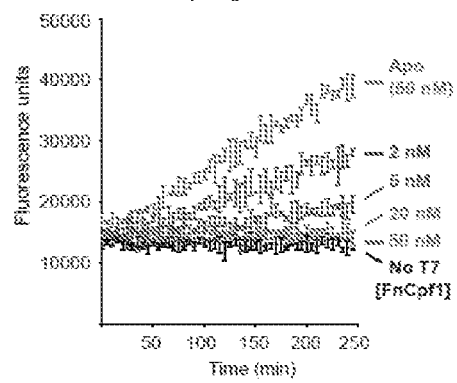

Chemical structure of hit compounds

BRD-K33182911-001-01-8
(BRD2911)

BRD-K36151368-001-01-8
(BRD1368)

BRD-K86027682-001-01-8
(BRD7682)

BRD-K96745813-001-01-5
(BRD5813)

Compound mediated inhibition of Cas9 activity in egfp-U2OS cells (48h treatment)

Cell images for compound mediated inhibition of Cas9
activity in egfp-U2OS cells (48h treatment)

Untreated cells

DMSO control

BRD2911

BRD1368

BRD7682

BRD5813

Compound mediated inhibition of Cas9 activity in HEK293T cells (48h treatment) as measured by Surveyor assay

SEQUENCE LISTING

<160> NUMBER OF SEQ ID NOS: 24

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ggctggacca cgcgggaaaa tccacctagg tggttcctct tcggatgttc catcctttt    58

<210> SEQ ID NO 2
<211> LENGTH: 58
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 2
aaaggatgga acatccgaag aggaaccacc taggtggatt ttcccgcgtg gtccagcc         58

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
taatacgact cactatagga cgcgaccgaa atggtgaagg acgggt                     46

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
actcactata gggacgcgac cgaaatggtg aaggacgggt ccagtgcttc gg              52

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cgtccttcac catttcggtc gcgtccctat agtgagtcgt attagttcca t               51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
atggaactaa tacgactcac tatagggacg cgaccgaaat ggtgaaggac g               51

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atagtgagtc gtatta                                                     16

<210> SEQ ID NO 8
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 8
cgtccctata gtgagt                                                         16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atggaactaa tacgac                                                         16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtcgtattag ttccat                                                         16

<210> SEQ ID NO 11
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
gcuauaggac gcgaccgaaa guuuuagagc uagaaauagc aaguuaaaau aaggcuaguc         60
cguuaucaac uugaaaaagu ggcaccgagu cggugcuuuu                              100

<210> SEQ ID NO 12
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggugacgcga ccgaaauggu gaaggacggg uccagugcuu cggcacuguu gaguagagug         60
ugagcuccgu aacuggucgc guc                                                 83

<210> SEQ ID NO 13
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: a, c, u, g, unknown or other

<400> SEQUENCE: 13
ggnnnngacg cgaccgaaau ggugaaggac ggguccagug cuucggcacu guugaguaga         60
```

```
gugugagcuc cguaacuggu cgcguc                                           86
```

<210> SEQ ID NO 14
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gcgcgctttc taatacgact cactataggg tgacgcgacc gaaatggtga aggacgggtc      60
cagtgcttcg gcactgttga gtagagtgtg agctccgtaa ctggtcgcgt c              111
```

<210> SEQ ID NO 15
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (31)..(34)
<223> OTHER INFORMATION: a, c, t, g, unknown or other

<400> SEQUENCE: 15

```
gcgcgcnnnn taatacgact cactataggg nnnngacgcg accgaaatgg tgaaggacgg      60
gtccagtgct tcggcactgt tgagtagagt gtgagctccg taactggtcg cgtc           114
```

<210> SEQ ID NO 16
<211> LENGTH: 1368
<212> TYPE: PRT
<213> ORGANISM: Streptococcus pyogenes

<400> SEQUENCE: 16

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
```

```
                    580             585             590
Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
            610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685

Ala Asn Arg Asn Phe Met Gln Leu Ile His Asp Asp Ser Leu Thr Phe
            690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
            770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp His Ile Val Pro Gln Ser Phe Leu Lys
            835             840             845

Asp Asp Ser Ile Asp Asn Lys Val Leu Thr Arg Ser Asp Lys Asn Arg
            850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
            915             920             925

Lys His Val Ala Gln Ile Leu Asp Ser Arg Met Asn Thr Lys Tyr Asp
            930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys  Tyr Pro Lys Leu Glu  Ser Glu Phe
            995             1000             1005
```

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 17
<211> LENGTH: 4107
<212> TYPE: DNA
<213> ORGANISM: Streptococcus pyogenes

<400> SEQUENCE: 17

```
atggataaga atactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaatct tataggggct ctttttattg acagtggaga gacagcggaa     180
gcgactcgtc tcaaacggac agctcgtaga aggtatacac gtcggaagaa tcgtatttgt    240
tatctacagg agattttttc aaatgagatg gcgaaagtag atgatagttt ctttcatcga    300
cttgaagagt cttttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca ttttttgatt gagggagatt taaatcctga ataatagtgat   540
gtggacaaac tatttatcca gttggtacaa acctacaatc aattatttga agaaaacccc    600
attaacgcaa gtggagtaga tgctaaagcg attctttctg cacgattgag taaatcaaga    660
cgattagaaa atctccattgc tcagctcccc ggtgagaaga aaaatggctt atttgggaat   720
ctcattgctt tgtcattggg tttgaccccct aattttaaat caaatttttga tttggcagaa  780
gatgctaaat tacagctttc aaaagatact tacgatgatg atttagataa tttattggcg   840
caaattggag atcaatatgc tgatttgttt ttggcagcta agaatttatc agatgctatt   900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc ttttttgatc aatcaaaaaa cggatatgca   1080
ggttatattg atgggggagc tagccaagaa gaattttata aatttatcaa accaattttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga aagacaagaa agacttttat ccattttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagttttgc tttatgagta ttttacggtt  1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat aaaagaaga ttatttcaaa aaaatagaat gttttgatag tgttgaaatt    1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa acatatgct    1920
cacctctttg atgataaggt gatgaaacag cttaaacgtc gccgttatac tggttgggga   1980
cgtttgtctc gaaaattgat taatggtatt agggataagc aatctggcaa acaatatta    2040
gatttttga aatcagatgg ttttgccaat cgcaatttta tgcagctgat ccatgatgat   2100
agtttgacat ttaaagaaga cattcaaaaa gcacaagtgt ctggacaagg cgatagtta    2160
catgaacata ttgcaaattt agctggtagc cctgctatta aaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
```

```
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taacttattc gagaggttaa agtgattac cttaaaatct    2880
aaattagttt ctgacttccg aaaagatttc caattctata agtacgtga gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060
atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatgaaa agaagttcct ttgaaaaaaa tccgattgac    3540
tttttagaag ctaaaggata taggaagtt aaaaaagact taatcattaa actacctaaa    3600
tatagtcttt ttgagttaga aaacggtcgt aacggatgc tggctagtgc cggagaatta    3660
caaaaaggaa atgagctggc tctgccaagc aaatatgtga atttttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga acacgcatt     4080
gatttgagtc agctaggagg tgactga                                        4107
```

<210> SEQ ID NO 18
<211> LENGTH: 1300
<212> TYPE: PRT
<213> ORGANISM: Francisella tularensis

<400> SEQUENCE: 18

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
```

```
            50                  55                  60
Ile Leu Ser Ser Val Cys Ile Ser Glu Asp Leu Leu Gln Asn Tyr Ser
 65                  70                  75                  80

Asp Val Tyr Phe Lys Leu Lys Lys Ser Asp Asp Asn Leu Gln Lys
                 85                  90                  95

Asp Phe Lys Ser Ala Lys Asp Thr Ile Lys Lys Gln Ile Ser Glu Tyr
                    100                 105                 110

Ile Lys Asp Ser Glu Lys Phe Lys Asn Leu Phe Asn Gln Asn Leu Ile
                115                 120                 125

Asp Ala Lys Lys Gly Gln Glu Ser Asp Leu Ile Leu Trp Leu Lys Gln
            130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                    165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
                195                 200                 205

Pro Lys Phe Leu Glu Asn Lys Ala Lys Tyr Glu Ser Leu Lys Asp Lys
                210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                    245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
                275                 280                 285

Phe Val Asn Gly Glu Asn Thr Lys Arg Lys Gly Ile Asn Glu Tyr Ile
                290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                    325                 330                 335

Phe Val Ile Asp Lys Leu Glu Asp Asp Ser Asp Val Val Thr Thr Met
                    340                 345                 350

Gln Ser Phe Tyr Glu Gln Ile Ala Ala Phe Lys Thr Val Glu Glu Lys
                355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                    405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
                435                 440                 445

Lys Tyr Leu Ser Leu Glu Thr Ile Lys Leu Ala Leu Glu Glu Phe Asn
                450                 455                 460

Lys His Arg Asp Ile Asp Lys Gln Cys Arg Phe Glu Glu Ile Leu Ala
465                 470                 475                 480
```

```
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
                500                 505                 510
Asp Leu Leu Gln Ala Ser Ala Glu Asp Val Lys Ala Ile Lys Asp
                515                 520                 525
Leu Leu Asp Gln Thr Asn Asn Leu Leu His Lys Leu Lys Ile Phe His
            530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
                580                 585                 590
Asp Glu Lys Phe Lys Leu Asn Phe Glu Asn Ser Thr Leu Ala Asn Gly
                595                 600                 605
Trp Asp Lys Asn Lys Glu Pro Asp Asn Thr Ala Ile Leu Phe Ile Lys
                610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
                660                 665                 670
Phe Phe Ser Ala Lys Ser Ile Lys Phe Tyr Asn Pro Ser Glu Asp Ile
                675                 680                 685
Leu Arg Ile Arg Asn His Ser Thr His Thr Lys Asn Gly Ser Pro Gln
                690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
                740                 745                 750
Phe Tyr Arg Glu Val Glu Asn Gln Gly Tyr Lys Leu Thr Phe Glu Asn
                755                 760                 765
Ile Ser Glu Ser Tyr Ile Asp Ser Val Val Asn Gln Gly Lys Leu Tyr
770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
                820                 825                 830
Arg Lys Gln Ser Ile Pro Lys Lys Ile Thr His Pro Ala Lys Glu Ala
                835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
```

```
Asn Asp Glu Ile Asn Leu Leu Leu Lys Glu Lys Ala Asn Asp Val His
                900                 905                 910
Ile Leu Ser Ile Asp Arg Gly Glu Arg His Leu Ala Tyr Tyr Thr Leu
        915                 920                 925
Val Asp Gly Lys Gly Asn Ile Ile Lys Gln Asp Thr Phe Asn Ile Ile
    930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
        980                 985                 990
Ala Lys Leu Val Ile Glu Tyr Asn Ala Ile Val Val Phe Glu Asp Leu
    995                 1000                1005
Asn Phe Gly Phe Lys Arg Gly Arg Phe Lys Val Glu Lys Gln Val
    1010                1015                1020
Tyr Gln Lys Leu Glu Lys Met Leu Ile Glu Lys Leu Asn Tyr Leu
    1025                1030                1035
Val Phe Lys Asp Asn Glu Phe Asp Lys Thr Gly Gly Val Leu Arg
    1040                1045                1050
Ala Tyr Gln Leu Thr Ala Pro Phe Glu Thr Phe Lys Lys Met Gly
    1055                1060                1065
Lys Gln Thr Gly Ile Ile Tyr Tyr Val Pro Ala Gly Phe Thr Ser
    1070                1075                1080
Lys Ile Cys Pro Val Thr Gly Phe Val Asn Gln Leu Tyr Pro Lys
    1085                1090                1095
Tyr Glu Ser Val Ser Lys Ser Gln Glu Phe Phe Ser Lys Phe Asp
    1100                1105                1110
Lys Ile Cys Tyr Asn Leu Asp Lys Gly Tyr Phe Glu Phe Ser Phe
    1115                1120                1125
Asp Tyr Lys Asn Phe Gly Asp Lys Ala Ala Lys Gly Lys Trp Thr
    1130                1135                1140
Ile Ala Ser Phe Gly Ser Arg Leu Ile Asn Phe Arg Asn Ser Asp
    1145                1150                1155
Lys Asn His Asn Trp Asp Thr Arg Glu Val Tyr Pro Thr Lys Glu
    1160                1165                1170
Leu Glu Lys Leu Leu Lys Asp Tyr Ser Ile Glu Tyr Gly His Gly
    1175                1180                1185
Glu Cys Ile Lys Ala Ala Ile Cys Gly Glu Ser Asp Lys Lys Phe
    1190                1195                1200
Phe Ala Lys Leu Thr Ser Val Leu Asn Thr Ile Leu Gln Met Arg
    1205                1210                1215
Asn Ser Lys Thr Gly Thr Glu Leu Asp Tyr Leu Ile Ser Pro Val
    1220                1225                1230
Ala Asp Val Asn Gly Asn Phe Phe Asp Ser Arg Gln Ala Pro Lys
    1235                1240                1245
Asn Met Pro Gln Asp Ala Asp Ala Asn Gly Ala Tyr His Ile Gly
    1250                1255                1260
Leu Lys Gly Leu Met Leu Leu Gly Arg Ile Lys Asn Asn Gln Glu
    1265                1270                1275
Gly Lys Lys Leu Asn Leu Val Ile Lys Asn Glu Glu Tyr Phe Glu
    1280                1285                1290
Phe Val Gln Asn Arg Asn Asn
```

1295        1300

<210> SEQ ID NO 19
<211> LENGTH: 3903
<212> TYPE: DNA
<213> ORGANISM: Francisella tularensis

<400> SEQUENCE: 19

| | | | | | |
|---|---|---|---|---|---|
| atgtcaattt | atcaagaatt | tgttaataaa | tatagtttaa | gtaaaactct | aagatttgag | 60 |
| ttaatcccac | agggtaaaac | acttgaaaac | ataaaagcaa | gaggtttgat | tttagatgat | 120 |
| gagaaaagag | ctaaagacta | caaaaaggct | aaacaaataa | ttgataaata | tcatcagttt | 180 |
| tttatagagg | agatattaag | ttcggtttgt | attagcgaag | atttattaca | aaactattct | 240 |
| gatgtttatt | ttaaacttaa | aaagagtgat | gatgataatc | tacaaaaaga | ttttaaaagt | 300 |
| gcaaaagata | cgataaagaa | acaaatatct | gaatatataa | aggactcaga | gaaatttaag | 360 |
| aatttgttta | tcaaaaccct | tatcgatgct | aaaaaagggc | aagagtcaga | tttaattcta | 420 |
| tggctaaagc | aatctaagga | taatggtata | gaactatttta | aagccaatag | tgatatcaca | 480 |
| gatatagatg | aggcgttaga | aataatcaaa | tcttttaaag | gttggacaac | ttattttaag | 540 |
| ggttttcatg | aaaatagaaa | aaatgttatt | agtagcaatg | atattcctac | atctattatt | 600 |
| tataggatag | tagtgataaa | tttgcctaaa | tttctagaaa | ataaagctaa | gtatgagagt | 660 |
| ttaaaagaca | aagctccaga | agctataaac | tatgaacaaa | ttaaaaaaga | tttggcagaa | 720 |
| gagctaaccct | ttgatattga | ctacaaaaca | tctgaagtta | tcaaagagt | ttttcactt | 780 |
| gatgaagttt | ttgagatagc | aaactttaat | aattatctaa | atcaaagtgg | tattactaaa | 840 |
| tttaatacta | ttattggtgg | taaatttgta | aatggtgaaa | atacaaagag | aaaaggtata | 900 |
| aatgaatata | taaatctata | ctcacagcaa | ataaatgata | aaacactcaa | aaaatataaa | 960 |
| atgagtgttt | tatttaagca | aattttaagt | gatacagaat | ctaaatcttt | tgtaattgat | 1020 |
| aagttagaag | atgatagtga | tgtagttaca | acgatgcaaa | gttttttatga | gcaaatagca | 1080 |
| gcttttaaaa | cagtagaaga | aaaatctatt | aagaaacac | tatctttatt | atttgatgat | 1140 |
| ttaaaagctc | aaaaacttga | tttgagtaaa | atttattttta | aaaatgataa | atctcttact | 1200 |
| gatctatcac | aacaagtttt | tgatgattat | agtgttattg | gtacagcggt | actagaatat | 1260 |
| ataactcaac | aaatagcacc | taaaaatctt | gataaccccta | gtaagaaaga | gcaagaatta | 1320 |
| atagccaaaa | aaactgaaaa | agcaaaatac | ttatctctag | aaactataaa | gcttgcctta | 1380 |
| gaagaattta | ataagcatag | agatatagat | aaacagtgta | ggtttgaaga | atacttgca | 1440 |
| aactttgcgg | ctattccgat | gatatttgat | gaaatagctc | aaaacaaaga | caatttggca | 1500 |
| cagatatcta | tcaaatatca | aaatcaaggt | aaaaaagacc | tacttcaagc | tagtgcggaa | 1560 |
| gatgatgtta | agctatcaa | ggatctttta | gatcaaacta | taatctctt | acataaacta | 1620 |
| aaaatatttc | atattagtca | gtcagaagat | aaggcaaata | ttttagacaa | ggatgagcat | 1680 |
| ttttatctag | tatttgagga | gtgctacttt | gagctagcga | atatagtgcc | tctttataac | 1740 |
| aaaattagaa | actatataac | tcaaaagcca | tatagtgatg | agaaatttaa | gctcaatttt | 1800 |
| gagaactcga | ctttggctaa | tggttgggat | aaaaataaag | agcctgacaa | tacggcaatt | 1860 |
| ttatttatca | aagatgataa | atattatctg | ggtgtgatga | ataagaaaaa | taacaaaata | 1920 |
| tttgatgata | aagctatcaa | agaaaataaa | ggcgagggtt | ataaaaaaat | tgtttataaa | 1980 |
| cttttacctg | gcgcaaataa | aatgttacct | aaggttttct | tttctgctaa | atctataaaa | 2040 |
| ttttataatc | ctagtgaaga | tatacttaga | ataagaaatc | attccacaca | tacaaaaaat | 2100 |

```
ggtagtcctc aaaaaggata tgaaaaattt gagtttaata ttgaagattg ccgaaaattt    2160 atagatttt ataaacagtc tataagtaag catccggagt ggaaagattt tggatttaga     2220
ttttctgata ctcaaagata taattctata gatgaatttt atagagaagt tgaaaatcaa    2280
ggctacaaac taacttttga aaatatatca gagagctata ttgatagcgt agttaatcag    2340
ggtaaattgt acctattcca aatctataat aaagattttt cagcttatag caaagggcga    2400
ccaaatctac atactttata ttggaaagcg ctgtttgatg agagaaatct tcaagatgtg    2460
gtttataagc taaatggtga ggcagagctt ttttatcgta aacaatcaat acctaaaaaa    2520
atcactcacc cagctaaaga ggcaatagct aataaaaaca aagataatcc taaaaaagag    2580 agtgttttg aatatgattt aatcaaagat aaacgcttta ctgaagataa gtttttcttt     2640
cactgtccta ttacaatcaa ttttaaatct agtggagcta ataagtttaa tgatgaaatc    2700
aatttattgc taaagaaaaa agcaaatgat gttcatatat taagtataga tagaggtgaa    2760
agacatttag cttactatac tttggtagat ggtaaaggca atatcatcaa acaagatact    2820
ttcaacatca ttggtaatga tagaatgaaa acaaactacc atgataagct tgctgcaata    2880
gagaaagata gggattcagc taggaaagac tggaaaaaga taaataacat caaagagatg    2940
aaagagggct atctatctca ggtagttcat gaaatagcta agctagttat agagtataat    3000
gctattgtgg ttttgagga tttaaatttt ggatttaaaa gagggcgttt caaggtagag    3060
aagcaggtct atcaaaagtt agaaaaaatg ctaattgaga aactaaacta tctagttttc    3120
aaagataatg agtttgataa aactggggga gtgcttagag cttatcagct aacagcacct    3180
tttgagactt ttaaaaagat gggtaaacaa acaggtatta tctactatgt accagctggt    3240
tttacttcaa aaatttgtcc tgtaactggt tttgtaaatc agttatatcc taagtatgaa    3300
agtgtcagca atctcaaga gttctttagt aagtttgaca gatttgtta taaccttgat    3360 aagggctatt ttgagtttag ttttgattat aaaaactttg gtgacaaggc tgccaaaggc    3420
aagtggacta tagctagctt tgggagtaga ttgattaact ttagaaattc agataaaaat    3480
cataattggg atactcgaga agtttatcca actaaagagt tggagaaatt gctaaaagat    3540
tattctatcg aatatgggca tggcgaatgt atcaaagcag ctatttgcgg tgagagcgac    3600
aaaaagtttt ttgctaagct aactagtgtc ctaaatacta tcttacaaat gcgtaactca    3660
aaaacaggta ctgagttaga ttatctaatt tcaccagtag cagatgtaaa tggcaatttc    3720
tttgattcgc gacaggcgcc aaaaaatatg cctcaagatg ctgatgccaa tggtgcttat    3780
catattgggc taaaaggtct gatgctacta ggtaggatca aaaataatca agagggcaaa    3840
aaactcaatt tggttatcaa aaatgaagag tatttgagt cgtgcagaa taggaataac      3900 taa                                                                   3903
```

<210> SEQ ID NO 20
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20

```
gggagacgca acugaaugaa auggugaagg acggguccag guguggcugc uucggcagug    60
cagcuuguug aguagagugu gagcuccgcg uaacuagucg cgucac                   106
```

```
<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acccgtcctt caccatttcg gtcgcgtcct atagtgagtc gtatta            46

<210> SEQ ID NO 22
<211> LENGTH: 15
<212> TYPE: DNA
<213> ORGANISM: Unknown
<220> FEATURE:
<223> OTHER INFORMATION: Description of Unknown:
      T7 promoter

<400> SEQUENCE: 22
taatacgact cacta                                              15

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccaagcgca cctaatttcc                                         20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggaaauuagg ugcgcuuggc                                         20
```

INHIBITORS OF RNA GUIDED NUCLEASES AND USES THEREOF

CROSS-REFERENCE TO RELATED APPLICATION

This application is the U.S. national phase application, pursuant to 35 U.S.C. § 371, of PCT international application Ser. No.: PCT/US2017/059365, filed Oct. 31, 2017, designating the United States and published in English, which claims the benefit of the following U.S. Provisional Application No. 62/416,017, filed Nov. 1, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 5, 2017, is named 167741_014101-PCT_SL.txt and is 39,480 bytes in size.

STATEMENT OF RIGHTS TO INVENTIONS MADE UNDER FEDERALLY SPONSORED RESEARCH

This invention was made with government support under Grant No. AI126239 awarded by the National Institutes of Health. The government has certain rights in the invention.

BACKGROUND OF THE INVENTION

The CRISPR (clustered regularly interspaced short palindromic repeat) system is an adaptive immune system used by bacteria and archaea to defend against invading phages or mobile genetic elements. The most studied CRISPR system employs an RNA-guided endonuclease Cas9, which can cleave double-stranded target DNA in multiple cell types. Cas9 identifies the target sequence by two recognition mechanisms: (i) Watson-Crick base-pairing between the target DNA sequence and guide RNA and (ii) Protospacer Adjacent Motif (PAM) sequence on the target DNA. Upon target recognition, Cas9 induces double-strand breaks in the target gene, which when repaired by non-homologous end joining (NHEJ) can result in frameshift mutations and gene knockdown. Alternatively, homology-directed repair (HDR) at the double-strand break site can allow insertion of the desired sequence.

Two common variants of Cas9 are SpCas9 and SaCas9, which naturally occur in *S pyogenes* and *S aureus*, respectively, and recently another endonuclease called Cpf1 has been reported. The relative ease of targeting Cas9/Cpf1 to specific genomic loci has enabled the development of revolutionary biomedical technologies. For example, catalytically inactive Cas9 (called dCas9), when fused to transcriptional activators, has enabled genome-wide screening of gene targets. Further, by targeting dCas9 to the promoter or exonic sequences, transcriptional repression has been accomplished. In yet another example, a fusion of dCas9 to acetyltransferases has enabled epigenome editing. Imaging of specific genomic loci has been accomplished by fusing dCas9 to GFP.

There are multiple reasons to establish controls on Cas9 activity. First, as described by Paracelsus' "The dose makes the poison", dosable control of the therapeutic activity is important for effective therapeutic strategies. Indeed, Cas9 exhibits undesirable off-target editing and chromosomal translocations when present at high concentrations. Second, most gene delivery systems have constitutively active Cas9, which is important to be terminated rapidly following on-target gene-editing. Third, Cas9-based technologies (e.g., transcriptional regulation) would benefit from dosable and temporal control of Cas9 activity.

The rapid ascension of CRISPR-based genome editing technologies has raised serious biosafety and bioterrorism concerns, leading to calls for a moratorium and responsible conduct. In particular, much concern has surrounded CRISPR-based gene drives. In sexual reproduction, the progenies receive two versions of a gene, one from each parent. Gene drives enable replacement of one version of the gene with the other "selfish" version of the gene, thereby converting a heterozygous individual to homozygous individual. In laboratory settings, CRISPR-based gene drives have successfully enabled self-propagation of engineered genes in multiple organisms (e.g., mosquitoes) and complete annihilation of wild-type genes. For example, using gene drives engineered mosquitoes have been generated that can wipe out the entire species by ensuring that every female progeny is infertile. Gene drives can be used to propagate a particular trait in the entire ecosystem, which may find use in the elimination of diseases (e.g., malaria, dengue fever) or invasive species, and reversing pesticide resistance in plants. On the other hand, there exists the malevolent use of gene drives in entomological and agricultural settings.

Reports of small-molecule controlled Cas9 activity are present in literature and involve fusing Cas9 to small-molecule controlled protein domains. Genetic-fusions of Cas9 to small-molecule controlled degrons (e.g., Wandless' destabilized domains) may allow aforementioned controls, but such fusions to have unacceptably high background activity presumably owing to the large size of Cas9. These systems also do not ensure dosage control—the small molecules act merely as an inducer of Cas9 activity. Further, these "inducer" small molecules cannot control gene drives containing wild-type Cas9/Cpf1. A general approach would be desirable to control all variants of Cas9/Cpf1, including the wild type and engineered versions. The use of "inducible" systems to control gene drives is also questionable given that the "inducer" small molecules are toxic at the organismal level (albeit not at the cellular level, where these systems were developed).

More importantly, large-sized genetic-fusion constructs are incompatible with the most common Cas9 gene delivery systems under investigation for therapeutic gene therapy. The application of these "inducible systems" in a therapeutic setting will be challenging as they involve fusion of large genes to Cas9 gene. Since Cas9 is a large protein, fitting even Cas9 gene into virus delivery systems (e.g., AAV) has been an enormous challenge. Even the smallest of the small-molecule controlled systems will aggrandize the delivery problems. Finally, many small-molecule "inducible" Cas9 constructs exist, but none allow dosable control. The reported "inducible" systems are not reversible upon removal of the small molecule, and therefore, do not allow complete temporal control.

Currently, no method exists for rapid, reversible dosage and temporal control of CRISPR-based technologies or to thwart the malevolent use of gene drives. Accordingly, a need exists for compositions and methods for inhibiting one or more activities of RNA guided endonuclease (e.g., Cas9, Cpf1). Such compositions and methods are useful for regulating the activity of RNA guided endonucleases (e.g., in genome editing).

SUMMARY OF THE INVENTION

The invention provides compositions and methods for inhibiting the activity of RNA guided endonucleases (e.g., Cas9, Cpf1), and methods of use therefor, including rapid, reversible, dosage, and/or temporal control of RNA guided endonuclease technologies. Also provided are high-throughput biochemical and cellular assays for detecting one or more activities of RNA guided endonucleases, and methods of using them to identify or screen agents that inhibit RNA guided nucleases.

In one aspect, the invention provides a compound having the structure of Formula IA, IB, IC, or ID:

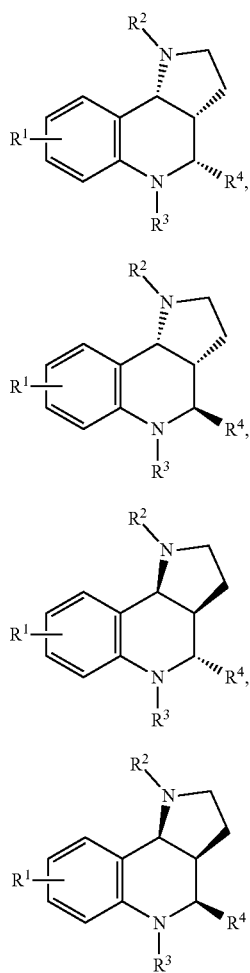

where $R^1$ is independently selected at each occurrence from hydrogen, —X, —R, -$L_1$-X, or -$L_1$-R; and $R^2$-$R^4$ are independently selected from hydrogen, —X, —R, -$L_1$-X, or -$L_1$-R; where X is independently selected at each occurrence from CN, OH, $CF_3$, COOH, OR, $NR_2$, or halogen (e.g., —Cl, —F, —Br, etc.);

$L_1$ is selected from —$(CH_2)_n$—, —$(CH_2)_n$—C(O)O—$(CH_2)_n$—, —$(CH_2)_n$—C(O)—NH—$(CH_2)_n$—, —$(CH_2)_n$—NH—C(O)—$(CH_2)_n$—, —$(CH_2)_n$—NH—$SO_2$—$(CH_2)_n$—, —$(CH_2)_n$—$SO_2$—NH—$(CH_2)_n$—, —$(CH_2)_n$—$SO_2$—$(CH_2)_n$—, —$(CH_2)_n$—$SO_2$—NH—C(O)—$(CH_2)_n$—, —$(CH_2)_n$—$R^L$—, —$R^L$—C(O)—O—, —S—, —S(O)—, —$SO_2$—NH—$(CH_2)_n$—, —$R^L$—NH—C(O)—$(CH_2)_n$—, —$R^L$—NH—$S(O)_2$—$(CH_2)_n$—, —$S(O)_2$—;

wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1\text{-}12}$ hydrocarbons (e.g., alkyl, alkenyl, alkynyl, aryl, alkyl-aryl, arayl-alkyl, and combinations thereof), optionally substituted with one or more groups X and/or with 1-10 heteroatoms selected from O, S, N, P, F, Cl, Br, I, and combinations thereof.

In another aspect, the invention provides a compound having the structure of Formula (II):

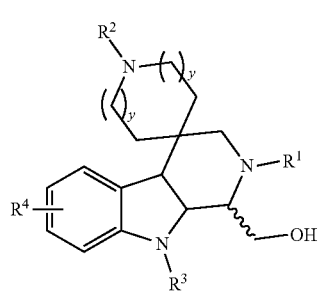

where "y" is 0 or 1, $R^4$ is independently selected at each occurrence from hydrogen, —X, —R, -$L_1$-X, or -$L_1$-R; and $R^1$-$R^3$ are independently selected from hydrogen, —X, —R, -$L_1$-X, or -$L_1$-R; where X is independently selected at each occurrence from CN, OH, $CF_3$, COOH, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—$(CH_2)_n$—, —$(CH_2)_n$—NH—C(O)—$(CH_2)_n$—, —$(CH_2)_n$—NH—$SO_2$—$(CH_2)_n$—, —$(CH_2)_n$—$SO_2$—NH—$(CH_2)_n$—, —$(CH_2)_n$—$SO_2$—$(CH_2)_n$—, —$(CH_2)_n$—$SO_2$—NH—C(O)—$(CH_2)_n$—, —$(CH_2)_n$—$R^L$—, —$R^L$—C(O)—O—, —$SO_2$—NH—$(CH_2)_n$—, —$R^L$—NH—C(O)—$(CH_2)_n$—, —$R^L$—NH—$S(O)_2$—$(CH_2)_n$—, —S—, —S(O)—, —$S(O)_2$—; wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1\text{-}12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In another aspect, the invention provides a compound having the structure of Formula (III):

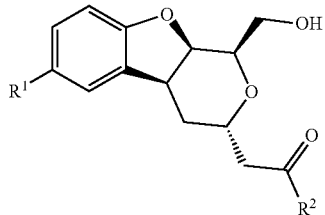

(III)

where $R^1$-$R^2$ are independently selected from hydrogen, —X, —R, -$L_1$-X, or -$L_1$-R; where X is independently selected at each occurrence from CN, OH, $CF_3$, COOH, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—$(CH_2)_n$—, —$(CH_2)_n$—NH—C(O)—$(CH_2)_n$—, —$(CH_2)_n$—NH—$SO_2$—$(CH_2)_n$—, —$(CH_2)_n$—$SO_2$—NH—$(CH_2)_n$—, —$(CH_2)_n$—$SO_2$—$(CH_2)_n$—, —$(CH_2)_n$—$SO_2$—NH—C(O)—$(CH_2)_n$—, —$(CH_2)_n$—$R^L$—, —$R^L$—C(O)—O—, —S—, —S(O)—, —$S(O)_2$—; wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In another aspect, the invention provides a compound having the structure:

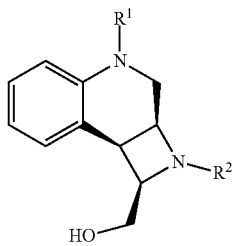

where each wavy bond may be in the R or the S configuration, $R^1$-$R^2$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—$(CH_2)_n$—, —$(CH_2)_n$—C(O)—NH—$(CH_2)_n$, —$(CH_2)_n$—NH—C(O)—$(CH_2)_n$—, —$(CH_2)_n$—NH—$SO_2$—$(CH_2)_n$—, —$(CH_2)_n$—$SO_2$—NH—$(CH_2)_n$, —$(CH_2)_n$—$SO_2$—$(CH_2)_n$—, —$(CH_2)_n$—$SO_2$—NH—C(O)—$(CH_2)_n$—, —$(CH_2)_n$—$R^L$—, —$R^L$—C(O)—O—, —S—, —S(O)—, —$S(O)_2$—; wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In another aspect, the invention provides a compound having the structure of formula (V):

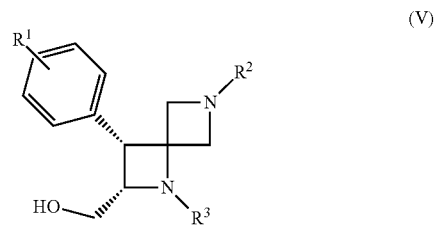

(V)

where $R^1$ is independently selected at each occurrence from hydrogen, —X, —R, -$L_1$-X, or -$L_1$-R; and $R^2$-$R^3$ are independently selected from hydrogen, —X, —R, -$L_1$-X, or -$L_1$-R; where X is independently selected at each occurrence from CN, OH, $CF_3$, COOH, OR, $NR_2$, or halogen (e.g., —Cl, —F, —Br, etc.);

$L_1$ is selected from —$(CH_2)_n$—, —$(CH_2)_n$—C(O)O—$(CH_2)_n$—, —$(CH_2)_n$—C(O)—NH—$(CH_2)_n$, —$(CH_2)_n$—NH—C(O)—$(CH_2)_n$—, —$(CH_2)_n$—NH—$SO_2$—$(CH_2)_n$—, —$(CH_2)_n$—$SO_2$—NH—$(CH_2)_n$—, —$(CH_2)_n$—$SO_2$—, —$(CH_2)_n$—$SO_2$—NH—C(O)—$(CH_2)_n$—, —$(CH_2)_n$—$R^L$—, —$R^L$—C(O)—O—, —S—, —S(O)—, —$S(O)_2$—; wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In another aspect, the invention provides a method of inhibiting the activity of an RNA guided endonuclease-guide RNA complex, involving contacting the RNA guided endonuclease-guide RNA complex with a small molecule.

In another aspect, the invention provides a method of detecting nucleic acid binding of an RNA guided endonuclease-guide RNA complex involving contacting the RNA guided endonuclease-guide RNA complex with a probe including an oligonucleotide having at least 4-12 PAM sites and a fluorescent reporter at the 5' terminus; and detecting an increase in fluorescence polarization relative to a reference, thereby detecting nucleic acid binding of the RNA guided endonuclease-guide RNA complex.

In another aspect, the invention provides a method of detecting nuclease activity of an RNA guided endonuclease-guide RNA complex involving providing an RNA guided endonuclease-guide RNA complex bound to a probe including an oligonucleotide having at least one PAM site and a fluorescent reporter at the 5' terminus; and detecting a decrease in fluorescence polarization relative to a reference, thereby detecting nucleic acid binding of the RNA guided endonuclease-guide RNA complex.

In another aspect, the invention provides a method of identifying an agent that inhibits an RNA guided endonuclease-guide RNA complex, involving contacting an RNA guided endonuclease-guide RNA complex with an agent in the presence of a probe including an oligonucleotide having at least 4-12 PAM sites and a fluorescent reporter at the 5' terminus; and failing to detect an increase in fluorescence polarization to a reference, thereby identifying the agent as an agent that inhibits an RNA guided endonuclease-guide RNA complex.

In another aspect, the invention provides a method of identifying an agent that inhibits nuclease activity of an RNA guided endonuclease-guide RNA complex, involving contacting an RNA guided endonuclease-guide RNA complex with an agent, where the RNA guided endonuclease-guide RNA complex is bound to a probe including an oligonucleotide having at least one PAM site and a fluorescent reporter at the 5' terminus; and detecting an increase in fluorescence polarization relative to a reference, thereby identifying the agent as an agent that inhibits nuclease activity of the RNA guided endonuclease-guide RNA complex.

In another aspect, the invention provides a method of identifying an agent that inhibits an RNA guided endonuclease-guide RNA complex, involving contacting a nucleic acid expressing a nucleic acid aptamer with the RNA guided endonuclease-guide RNA complex in the presence of a fluorophore molecule and an agent, where binding of the aptamer to the fluorophore molecule generates a fluorescent signal; and failing to detect a decrease in fluorescent signal relative to a reference, thereby identifying the agent as an agent that inhibits an RNA guided endonuclease-guide RNA complex.

In another aspect, the invention provides a method of detecting nucleic acid binding and/or nuclease activity of an RNA guided endonuclease-guide RNA complex involving contacting a nucleic acid expressing a nucleic acid aptamer with the RNA guided endonuclease-guide RNA complex in the presence of a fluorophore molecule, where binding of the aptamer to the fluorophore molecule generates a fluorescent signal, and detecting a decrease in fluorescent signal relative to a reference, thereby detecting nucleic acid binding or nuclease activity of the RNA guided endonuclease-guide RNA complex.

In another aspect, the invention provides a method of identifying an agent that inhibits an RNA guided endonuclease-guide RNA complex, involving one or more methods according to any aspect delineated herein.

In another aspect, the invention provides an oligonucleotide having at least 4, 5, 6, 7, 8, 9, 10, 11, 12, 13 or more PAM sites and a fluorescent reporter at the 5' or 3' terminus.

In another aspect, the invention provides a kit containing the oligonucleotide according to any aspect delineated herein.

In various embodiments of any aspect delineated herein, the nucleic acid binding and/or nuclease activity is inhibited or prevented by an agent (e.g., a small molecule). In various embodiments of any aspect delineated herein, the agent or small molecule inhibits one or more of nucleic acid binding or nuclease activity.

In various embodiments of any aspect delineated herein, the method is in vitro or in vivo. In various embodiments of any aspect delineated herein, the method is performed in a cell (e.g., a prokaryotic or eukaryotic cell). In some embodiments, the prokaryotic cell is a bacterium. In other embodiments, the eukaryotic cell is a human, mammalian, insect, plant, or yeast cell. In particular embodiments, the cell is in an organism (e.g., a human, mammal, vertebrate, invertebrate, insect, or plant).

In various embodiments of any aspect delineated herein, the agent or small molecule inhibits binding of the RNA guided endonuclease-guide RNA complex to a PAM site. In various embodiments, the RNA guided endonuclease is Cas9 or Cpf1. In various embodiments, the one or more PAM sites are 3' or 5' of a target nucleic acid (with reference to the non-target strand). In various embodiments of any aspect delineated herein, the one or more PAM sites have the nucleic acid sequence 5'-NGG-3' (SpCas9), 5'-TTN-3' (FnCpf1), 5'-NNGGGT-3' (SaCas9), or 5'-TTTN-3' (As/LbCpf1). In various embodiments of any aspect delineated herein, the fluorescent reporter is Fluorescein isothiocyanate (FITC).

In various embodiments, the probe includes an oligonucleotide having one or more of the nucleic acid sequences:

(SEQ ID NO: 1)
5'-GGCTGGACCACGCGGGAAAATCCACCTAGGTGGTTCCTCTTCGG

ATGTTCCATCCTTT/36-FAM-3', (SEQ ID NO: 2)
3'-CCGACCTGGTGCGCCCTTTTAGGTGGATCCACCAAGGAGAAGCC

TACAAGGTAGGAAA-5', (SEQ ID NO: 3)
5'-6-FAM/TAATACGACTCACTATAGGACGCGACCGAAATGGTGAA

GGACGGGT-3', (SEQ ID NO: 4)
5'-6-FAM/ACTCACTATAGGGACGCGACCGAAATGGTGAAGGACGG

GTCCAGTGCTTCGG-3', (SEQ ID NO: 5)
5'-CGTCCTTCACCATTTCGGTCGCGTCCCTATAGTGAGTCGTATTA

GTTCCAT/6-FAM-3',
and (SEQ ID NO: 6)
5'-6-FAM/ATGGAACTAATACGACTCACTATAGGGACGCGACCGAA

ATGGTGAAGGACG-3'.

In various embodiments, the probe or oligonucleotide specifically binds one or more of the nucleic acid sequences:

(SEQ ID NO: 7)
5'-ATAGTGAGTCGTATTA/3IABkFQ-3', (SEQ ID NO: 8)
5'-CGTCCCTATAGTGAGT/3IABkFQ-3',

-continued (SEQ ID NO: 9)
5'-5IABkFQ/ATGGAACTAATACGAC-3',
and (SEQ ID NO: 10)
5'-GTCGTATTAGTTCCAT/3IABkFQ-3'.

In various embodiments, the guide RNA includes the nucleic acid sequence:

(SEQ ID NO: 11)
5'-GCUAUAGGACGCGACCGAAAGUUUUAGAGCUAGAAAUAGCAAGU

UAAAAUAAGGCUAGUCCGUUAUCAACUUGAAAAAGUGGCACCGAGUC

GGUGCUUUU-3'.

In various embodiments of any aspect delineated herein, the reference is the fluorescence polarization of the probe in the presence of the agent or small compound and in the absence of the RNA guided endonuclease-guide RNA complex.

In various embodiments of any aspect delineated herein, the nucleic acid expresses a nucleic acid aptamer including a PAM site. In various embodiments, the nucleic acid aptamer has the sequence (SEQ ID NO: 11)
5'-GCUAUAGGACGCGACCGAAAGUUUUAGAGCUAGAAAUAGCAAGU

UAAAAUAAGGCUAGUCCGUUAUCAACUUGAAAAAGUGGCACCGAGUC

GGUGCUUUU-3', (SEQ ID NO: 12)
5'GGUGACGCGACCGAAAUGGUGAAGGACGGGUCCAGUGCUUCGG

CACUGUUGAGUAGAGUGUGAGCUCCGUAACUGGUCGCGUC-3',
or (SEQ ID NO: 13)
5'GGNNNNGACGCGACCGAAAUGGUGAAGGACGGGUCCAGUGCUUCG

GCACUGUUGAGUAGAGUGUGAGCUCCGUAACUGGUCGCGUC-3'.

In various embodiments, the DNA template of the nucleic acid has the sequence:

(SEQ ID NO: 14)
5'-GCGCGCTTTCTAATACGACTCACTATAGGGTGACGCGACCGAAA

TGGTGAAGGACGGGTCCAGTGCTTCGGCACTGTTGAGTAGAGTGTGA

GCTCCGTAACTGGTCGCGTC-3'
or (SEQ ID NO: 15)
5'-GCGCGCNNNNTAATACGACTCACTATAGGGNNNNGACGCGACCG

AAATGGTGAAGGACGGGTCCAGTGCTTCGGCACTGTTGAGTAGAGTG

TGAGCTCCGTAACTGGTCGCGTC-3'.

In various embodiments, the guide RNA includes the nucleic acid sequence:

(SEQ ID NO: 11)
5'-GCUAUAGGACGCGACCGAAAGUUUUAGAGCUAGAAAUAGCAAGU

UAAAAUAAGGCUAGUCCGUUAUCAACUUGAAAAAGUGGCACCGAGUC

GGUGCUUUU-3'

In various embodiments of any aspect delineated herein, the fluorophore molecule is one or more of 4-(3,5-difluoro-4-hydroxybenzylidene)-1,2-dimethyl-1H-imidazol-5-one (DFHBI).

In various embodiments, the reference is the fluorescence in the absence of the RNA guided endonuclease-guide RNA complex.

In various embodiments of any aspect delineated herein, the method further involves assaying the agent or small compound in one or more of an EGFP disruption assay, DNA cleavage assay, or Surveyor assay.

In various embodiments of any aspect delineated herein, the agent or small molecule is one or more of:

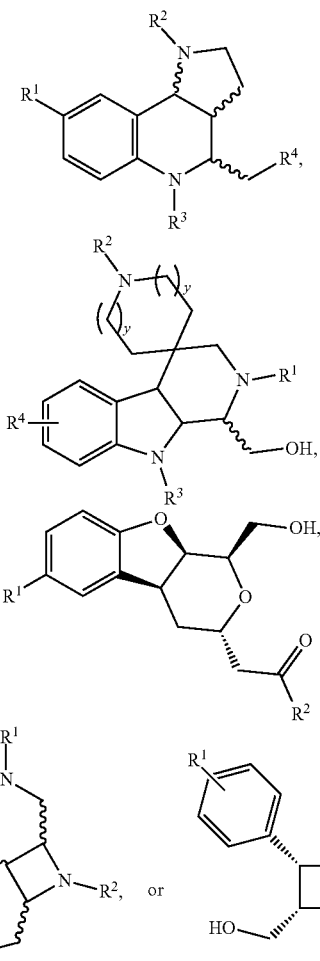

where each wavy bond may be in either the R or the S configuration, with the proviso that two wavy bonds of membered of a five or six membered fused ring have the same stereochemistry, $R^1$-$R^4$ are independently selected at each occurrence from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —NH—C(O)—$(CH_2)_n$—, —$(CH_2)_n$—$SO_2$—NH—, —$SO_2$—NH—$(CH_2)_n$, —$(CH_2)_n$—$SO_2$—, —$(CH_2)_n$—$SO_2$—NH—C(O)—, —R$^L$—NH—C(O)—(CH$_2$)$_n$—, —R$^L$—NH—S(O)$_2$—(CH$_2$)$_n$—, —(CH$_2$)$_n$—R$^L$—, —R$^L$—C(O)—O—, —S—, —S(O)—, —S(O)$_2$—; wherein n is independently at each occurrence 0, 1, 2, 3, 4, 5, or 6;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more groups X and/or with 1-10 heteroatoms selected from O, S, N, P, F, Cl, Br, I, and combinations thereof.

In various embodiments of any aspect delineated herein, the small molecule or compound has the formula of Formula I:

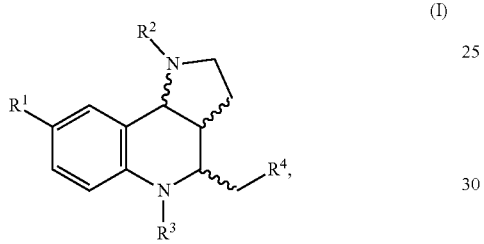

(I)

where R$^1$ is independently selected at each occurrence from hydrogen, —X, —R, -L$_1$-X, or -L$_1$-R; and R$_2$-R$_4$ are independently selected from hydrogen, —X, —R, -L$_1$-X, or -L$_1$-R; where X is independently selected at each occurrence from CN, OH, CF$_3$, COOH, OR, OR, NR$_2$, or halogen (e.g., —Cl, —F, —Br, etc.);

L$_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^L$—, —R$^L$—C(O)—O—, —R$^L$—NH—C(O)—(CH$_2$)$_n$—, —R$^L$—NH—S(O)$_2$—(CH$_2$)$_n$—, —S—, —S(O)—, —S(O)$_2$—; wherein n is independently at each occurrence 0, 1, 2, 3, 4, 5, or 6;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more groups X and/or with 1-10 heteroatoms selected from O, S, N, P, F, Cl, Br, I, and combinations thereof.

In various embodiments, the small molecule or compound has the formula of Formula IA, IB, IC, or ID:

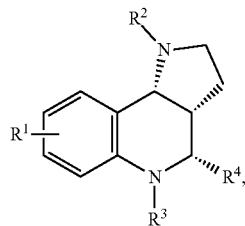

IA

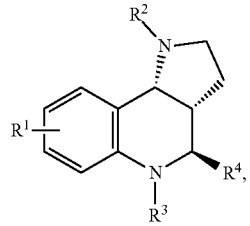

IB

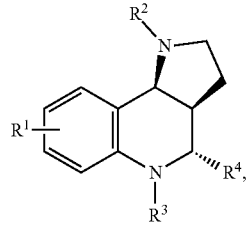

IC

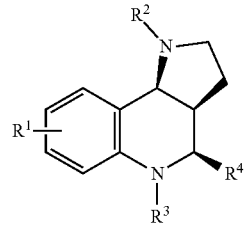

ID where R$^1$ is independently selected at each occurrence from hydrogen, —X, —R, -L$_1$-X, or -L$_1$-R; and R$^2$-R$^4$ are independently selected from hydrogen, —X, —R, -L$_1$-X, or -L$_1$-R; where X is independently selected at each occurrence from CN, OH, CF$_3$, COOH, OR, OR, NR$_2$, or halogen (e.g., —Cl, —F, —Br, etc.);

L$_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^L$—, —R$^L$—C(O)—O—, —R$^L$—NH—C(O)—(CH$_2$)$_n$—, —R$^L$—NH—S(O)$_2$—(CH$_2$)$_n$—, —S—, —S(O)—, —S(O)$_2$—;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more groups X and/or with 1-10 heteroatoms selected from O, S, N, P, F, Cl, Br, I, and combinations thereof.

In some embodiments, the small molecule or compound has the structure:

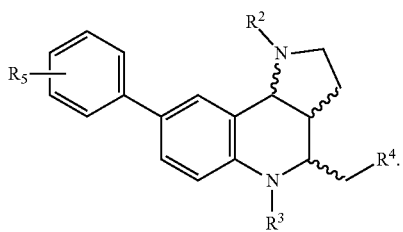
wherein $R_5$ is selected from hydrogen, —R, —X, -$L_1$-X, or -$L_1$-R. In some embodiments, $R_5$ is selected from halogen, alkoxy, —NH—CO-alkene, —NH—S(O)$_2$-alkene, or —NH—C(O)—(CH$_2$)$_n$-halogen.
In certain embodiments, the small molecule or compound is one or more of
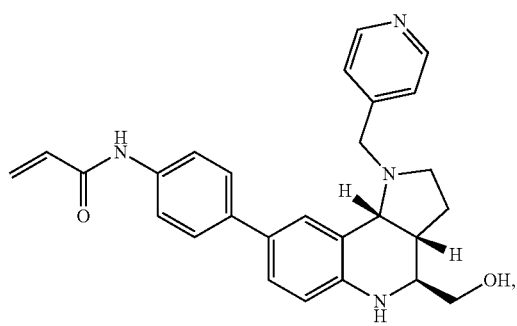
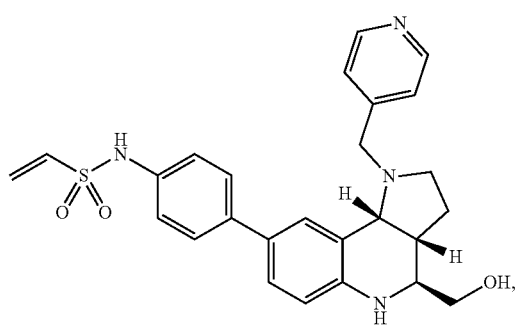
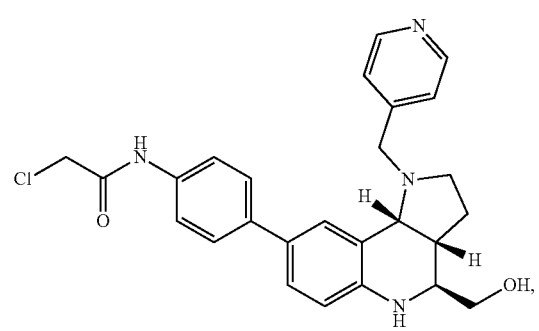
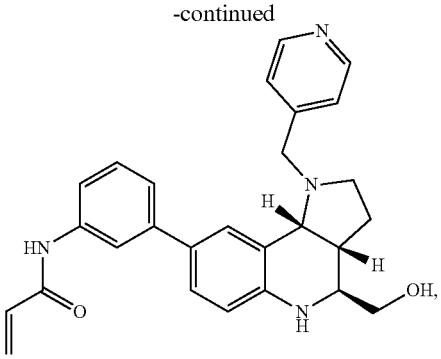
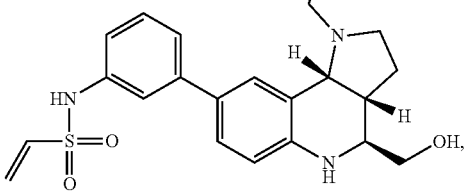
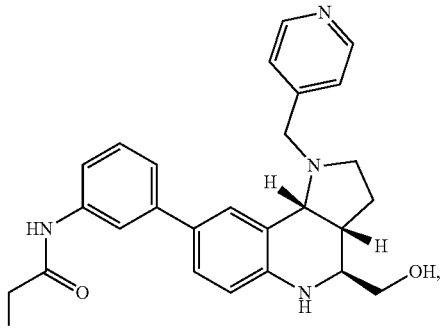
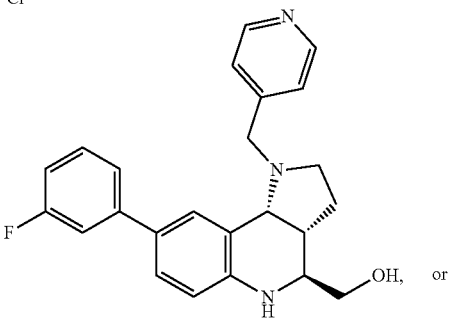
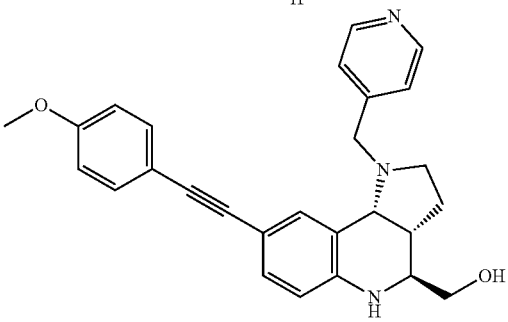
In various embodiments of any aspect delineated herein, the small molecule or compound has the formula of Formula II:

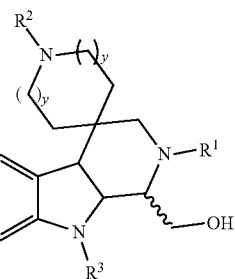

(II)

where "y" is 0 or 1, $R^4$ is independently selected at each occurrence from hydrogen, —X, —R, -L$_1$-X, or -L$_1$-R; and $R^1$-$R^3$ are independently selected from hydrogen, —X, —R, -L$_1$-X, or -L$_1$-R; where X is independently selected at each occurrence from CN, OH, CF$_3$, COOH, OR, OR, NR$_2$, or halogen (e.g., —Cl, —F, —Br, etc.);

L$_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —C(O)—NH—(CH$_2$)$_n$—, —(CH$_2$)$_n$—SO$_2$—NH—, —SO$_2$—NH—(CH$_2$)$_n$, —R$^L$—NH—C(O)—(CH$_2$)$_n$—, —R$^L$—NH—S(O)$_2$—(CH$_2$)$_n$—, —(CH$_2$)$_n$—SO$_2$—, —(CH$_2$)$_n$—SO$_2$—NH—C(O)—, —(CH$_2$)$_n$—R$^L$—, —R$^L$—C(O)—O—, —S—, —S(O)—, —S(O)$_2$—; wherein n is independently at each occurrence 0, 1, 2, 3, 4, 5, or 6;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In various embodiments, the small molecule or compound is one or more of:

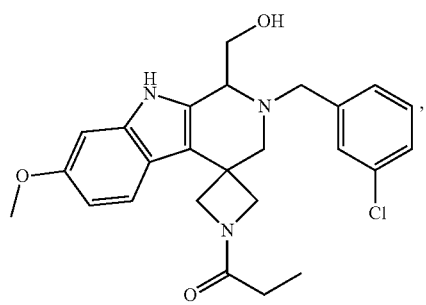

-continued

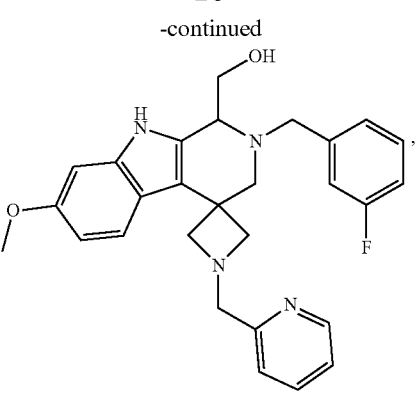

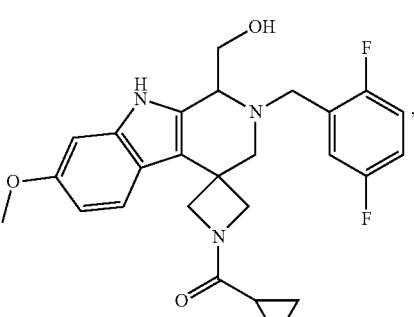

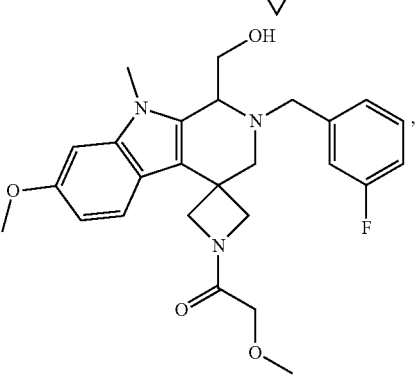

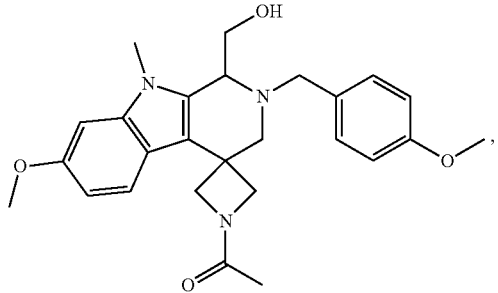

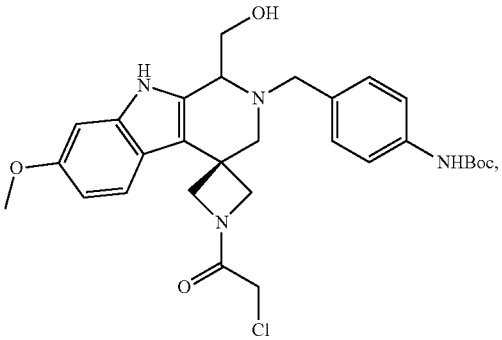

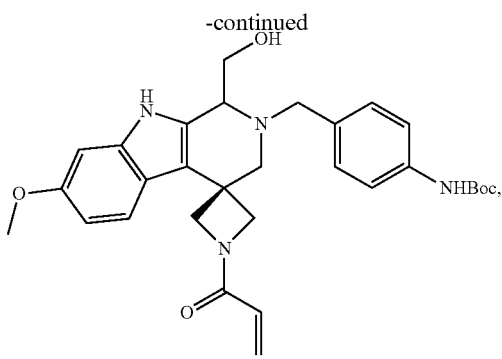

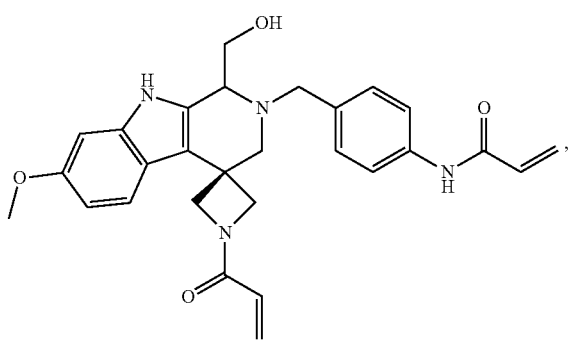

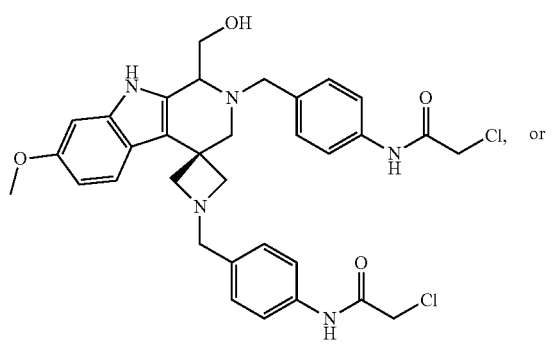

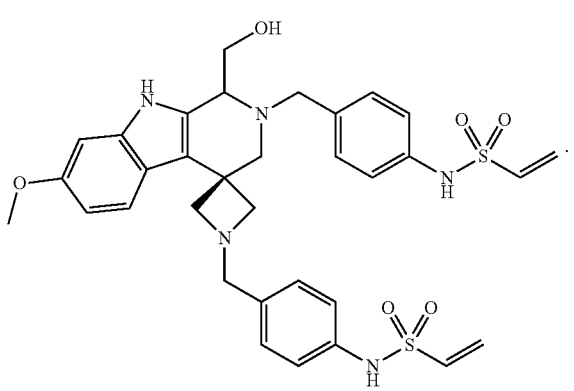

In various embodiments of any aspect delineated herein, the small molecule or compound has the formula of Formula III:

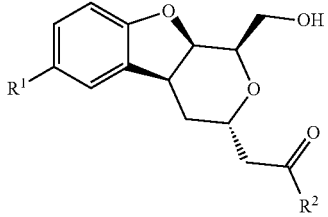

where $R^1$-$R^2$ are independently selected from hydrogen, —X, —R, -$L_1$-X, or -$L_1$-R; where X is independently selected at each occurrence from CN, OH, CF$_3$, COOH, OR, OR, NR$_2$, or halogen (e.g., —Cl, —F, —Br, etc.);

$L_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^L$—, —R$^L$—C(O)—O—, —S—, —S(O)—, —S(O)$_2$—;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In various embodiments of any aspect delineated herein, the small molecule or compound has the formula:

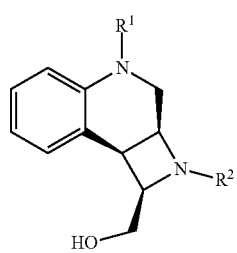

where each wavy bond may be in the R or the S configuration, $R^1$-$R^2$ are independently selected from hydrogen, —X, —R, -$L_1$-X, or -$L_1$-R; where X is independently selected at each occurrence from CN, OH, CF$_3$, COOH, OR, OR, NR$_2$, or halogen (e.g., —Cl, —F, —Br, etc.);

$L_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^L$—, —R$^L$—C(O)—O—, —S—, —S(O)—, —S(O)$_2$—;

R$^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In various embodiments of any aspect delineated herein, the small molecule or compound has the formula of Formula V:

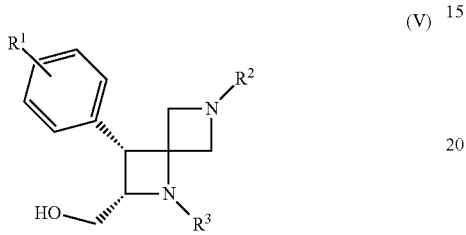

(V)

where $R^1$ is independently selected at each occurrence from hydrogen, —X, —R, -$L_1$-X, or -$L_1$-R; and $R^2$-$R^3$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —S—, —S(O)—, —$S(O)_2$—;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In various embodiments, the small molecule or compound is one or more of

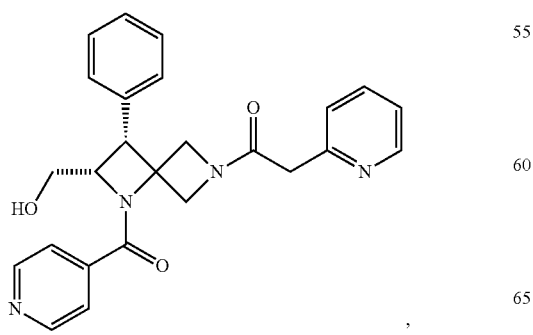

,

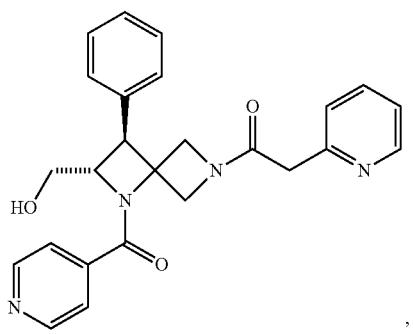

,

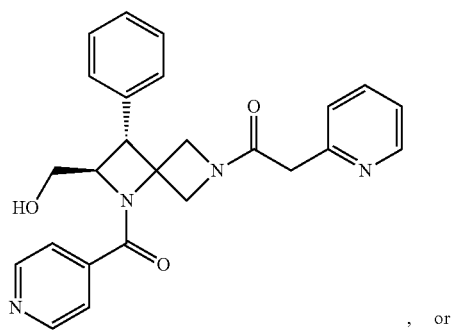

,

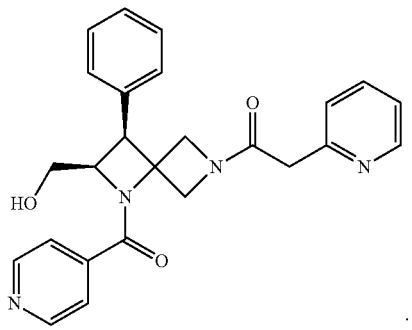

, or

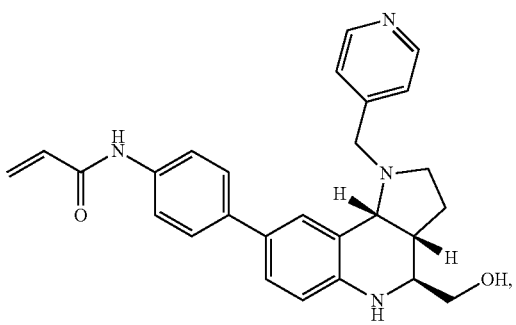

.

In various embodiments of any aspect delineated herein, the small molecule or compound is one or more of:

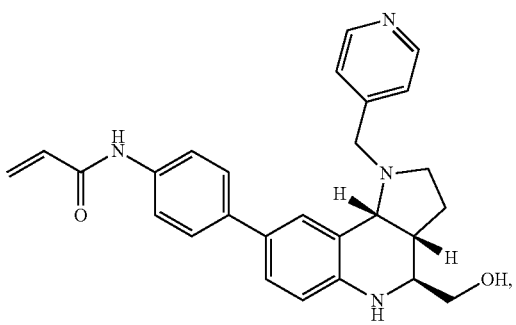

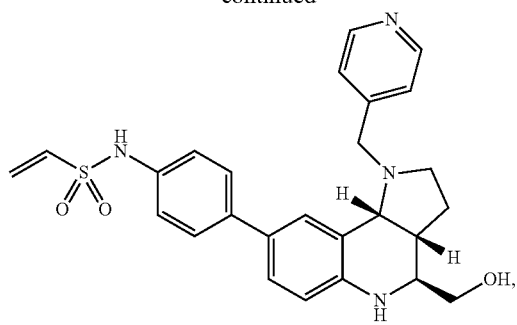
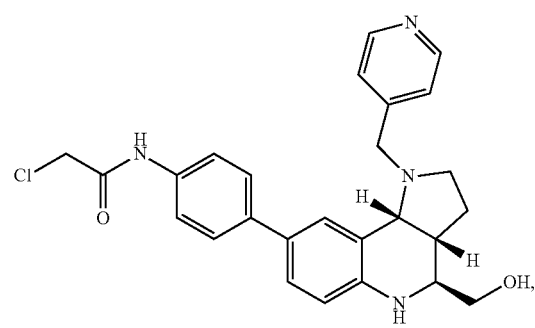
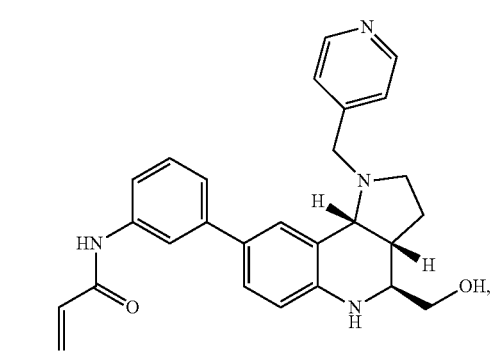
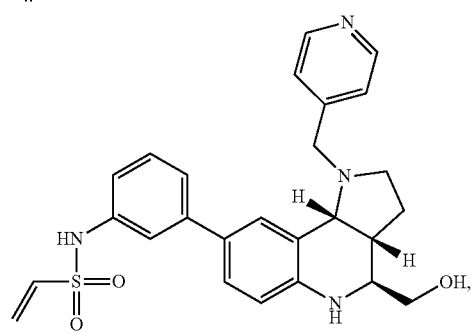
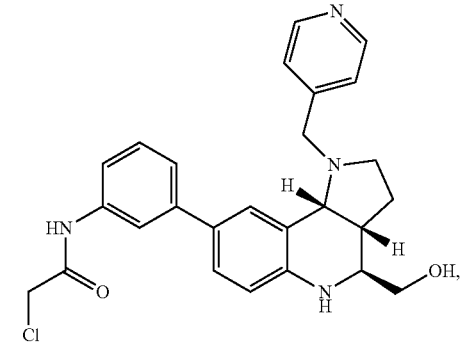
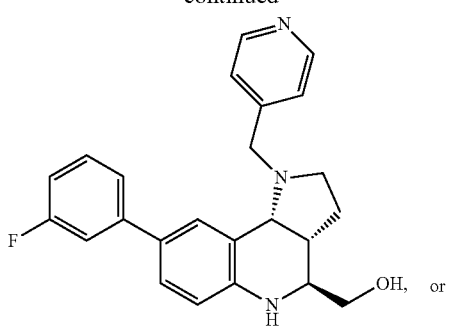
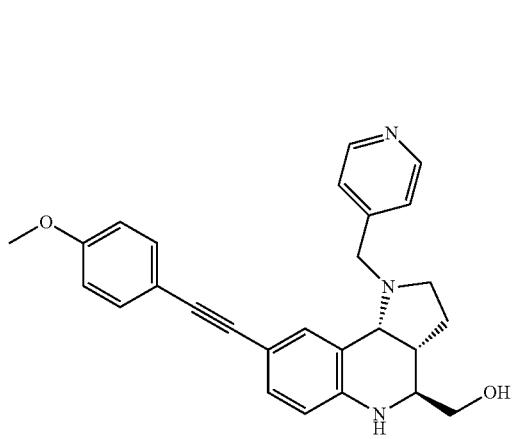
In various embodiments of any aspect delineated herein, the small molecule or compound is one or more of:
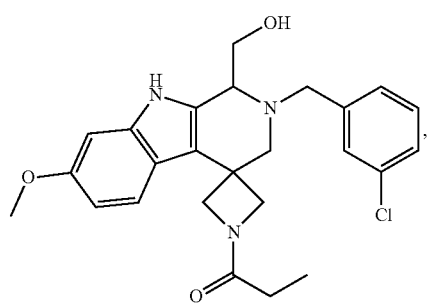
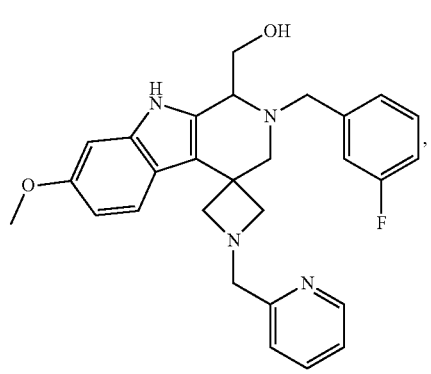

-continued
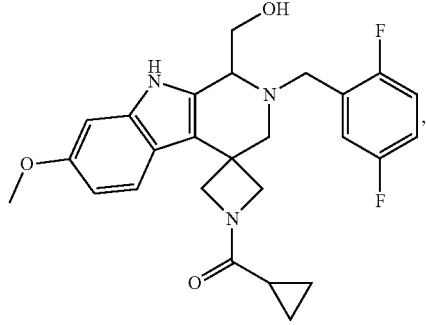
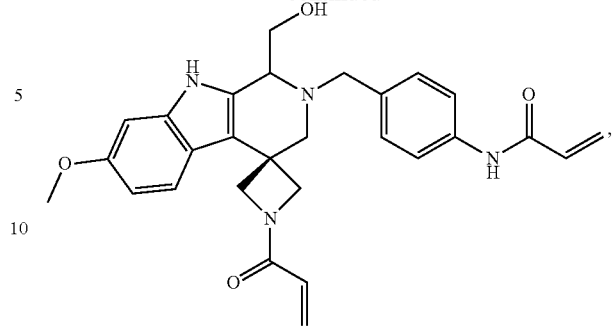
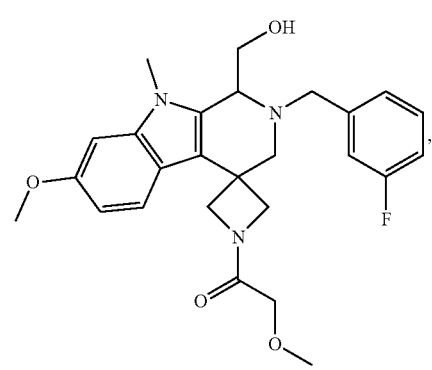
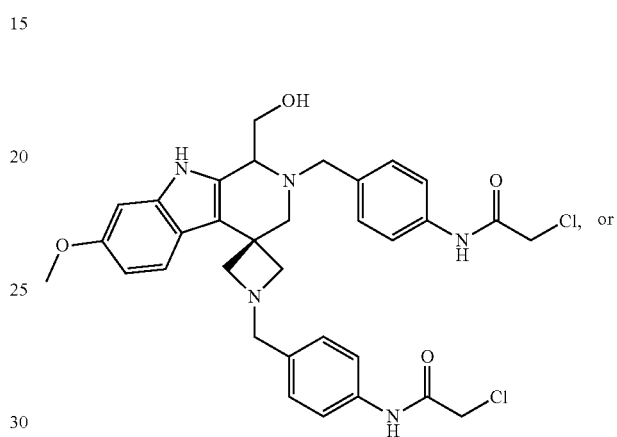
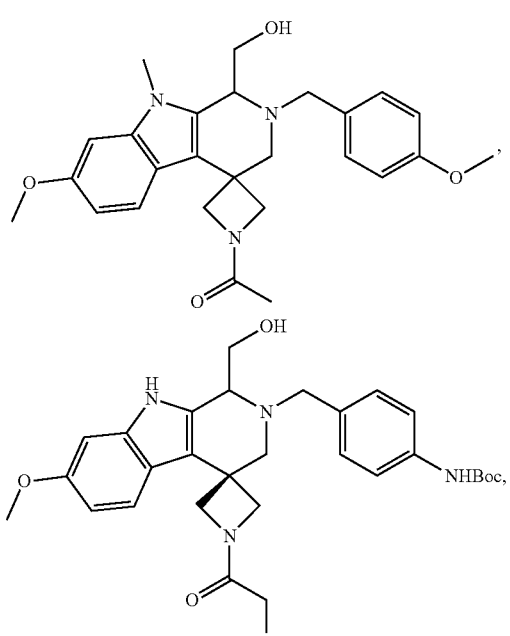
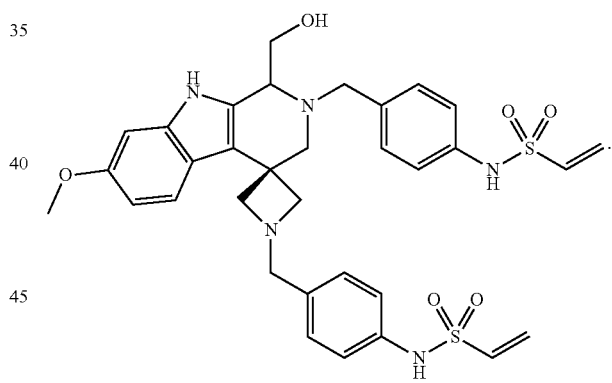
In various embodiments of any aspect delineated herein, the small molecule or compound is one or more of:
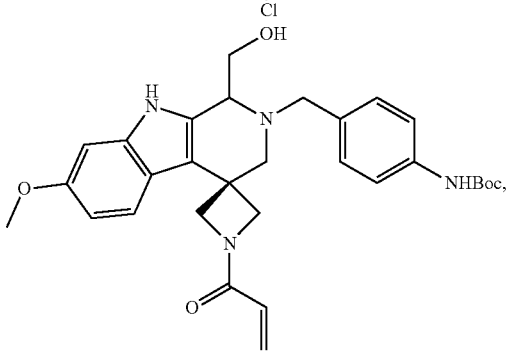
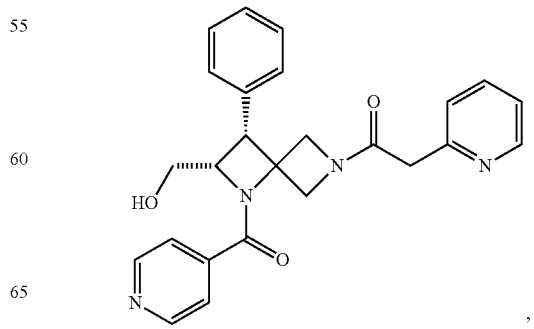

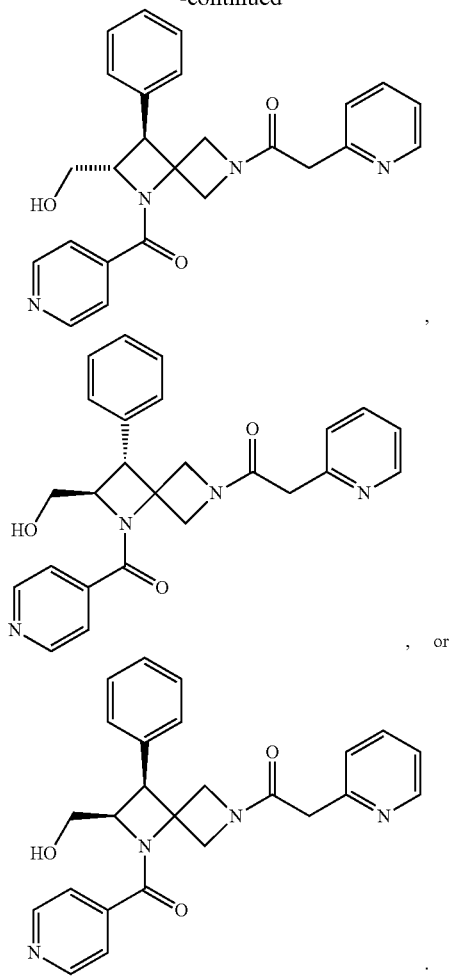

, or

In various embodiments of any aspect delineated herein, compositions comprising any of the compounds delineated may include stereo centers which each may independently be in the (R) configuration, the (S) configuration, or racemic mixtures.

Other features and advantages of the invention will be apparent from the detailed description, and from the claims.

Definitions

Unless various defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "RNA guided endonuclease" is meant a polypeptide having RNA binding activity, DNA binding activity, and/or DNA cleavage activity. RNA guided endonucleases form a complex with a guide RNA, which contains a sequence that is able to bind a target sequence on double stranded DNA. In some embodiments, the RNA guided endonuclease cleaves the double stranded target DNA. Exemplary, RNA guided endonucleases include, without limitation, Cpf1, Cas9, and active fragments, derivatives, and variants thereof.

By "Protospacer adjacent motif (PAM)" is meant a nucleic acid sequence immediately adjacent the nucleic acid sequence targeted by an RNA guided endonuclease (e.g., Cas9, Cpf1). In certain embodiments, the PAM sequence is the Cas9 PAM sequence: 5'-NGG-3'.

By "Cas9 (CRISPR associated protein 9)" is meant a polypeptide or fragment thereof having at least about 85% amino acid identity to NCBI Accession No. NP_269215 and having RNA binding activity, DNA binding activity, and/or DNA cleavage activity (e.g., endonuclease or nickase activity). An exemplary Cas9 polypeptide sequence is provided below.

(SEQ ID NO: 16)

```
  1  mdkkysigld igtnsvgwav itdeykvpsk kfkvlgntdr hsikknliga llfdsgetae
 61  atrlkrtarr rytrrknric ylqeifsnem akvddsffhr leesflveed kkherhpifg
121  nivdevayhe kyptiyhlrk klvdstdkad lrliylalah mikfrghfli egdlnpdnsd
181  vdklfiqlvq tynqlfeenp inasgvdaka ilsarlsksr rlenliaqlp gekknglfgn
241  lialslgltp nfksnfdlae daklqlskdt ydddldnlla qigdqyadlf laaknlsdai
301  llsdilrvnt eitkaplsas mikrydehhq dltllkalvr qqlpekykei ffdqskngya
361  gyidggasqe efykfikpil ekmdgteell vklnredllr kqrtfdngsi phqihlgelh
421  ailrrqedfy pflkdnreki ekiltfripy yvgplargns rfawmtrkse etitpwnfee
481  vvdkgasaqs fiermtnfdk nlpnekvlpk hsllyeyftv yneltkvkyv tegmrkpafl
541  sgeqkkaivd llfktnrkvt vkqlkedyfk kiecfdsvei sgvedrfnas lgtyhdllki
601  ikdkdfldne enediledv ltltlfedre mieerlktya hlfddkvmkq lkrrrytgwg
661  rlsrklingi rdkqsgktil dflksdgfan rnfmqlihdd sltfkediqk aqvsgqgdsl
721  hehianlags paikkgilqt vkvvdelvkv mgrhkpeniv iemarenqtt qkgqknsrer
781  mkrieegike lgsqilkehp ventqlqnek lylyylqngr dmyvdgeldi nrlsdydvdh
```

```
 841   ivpqsflkdd sidnkvltrs dknrgksdnv pseevvkkmk nywrqllnak litqrkfdnl
 901   tkaergglse ldkagfikrq lvetrqitkh vaqildsrmn tkydendkli revkvitlks
 961   klvsdfrkdf qfykvreinn yhhandayln avvgtalikk ypklesefvy gdykvydvrk
1021   miakseqeig katakyffys nimnffktei tlangeirkr plietngetg eivwdkgrdf
1081   atvrkvlsmp qvnivkktev qtggfskesi lpkrnsdkli arkkdwdpkk yggfdsptva
1141   ysvlvvakve kgkskklksv kellgitime rssfeknpid fleakgykev kkdliiklpk
1201   yslfelengr krmlasagel qkgnelalps kyvnflylas hyeklkgspe dneqkqlfve
1261   qhkhyldeii eqisefskry iladanldkv lsaynkhrdk pireqaenii hlftltnlga
1321   paafkyfdtt idrkrytstk evldatlihq sitglyetri dlsqlggd
```

"Cas9 function" can be defined by any of a number of assays including, but not limited to, fluorescence polarization-based nucleic acid bind assays, fluorescence polarization-based strand invasion assays, transcription assays, EGFP disruption assays, DNA cleavage assays, and/or Surveyor assays, for example, as described herein.

By "Cas 9 nucleic acid molecule" is meant a polynucleotide encoding a Cas9 polypeptide or fragment thereof. An exemplary Cas9 nucleic acid molecule sequence is provided at NCBI Accession No. NC_002737 and is shown below.

(SEQ ID NO: 17)
```
   1   atggataaga aatactcaat aggcttagat atcggcacaa atagcgtcgg atgggcggtg
  61   atcactgatg aatataaggt tccgtctaaa aagttcaagg ttctgggaaa tacagaccgc
 121   cacagtatca aaaaaatct tataggggct cttttatttg acagtggaga gacagcggaa
 181   gcgactcgtc tcaaacggac agctcgtaga aggtatacac gtcggaagaa tcgtatttgt
 241   tatctacagg agatttttc aaatgagatg gcgaaagtag atgatagttt ctttcatcga
 301   cttgaagagt ctttttggt ggaagaagac aagaagcatg aacgtcatcc tattttgga
 361   aatatagtag atgaagttgc ttatcatgag aaatatccaa ctatctatca tctgcgaaaa
 421   aaattggtag attctactga taaagcggat tgcgcttaa tctatttggc cttagcgcat
 481   atgattaagt tcgtggtca ttttttgatt gagggagatt aaatcctga taatagtgat
 541   gtggacaaac tatttatcca gttggtacaa acctacaatc aattatttga agaaaaccct
 601   attaacgcaa gtggagtaga tgctaaagcg attctttctg cacgattgag taaatcaaga
 661   cgattagaaa atctccattgc tcagctcccc ggtgagaaga aaatggctt atttgggaat
 721   ctcattgctt tgtcattggg tttgacccct aatttaaat caaattttga tttggcagaa
 781   gatgctaaat tacagctttc aaaagatact tacgatgatg atttagataa tttattggcg
 841   caaattggag atcaatatgc tgatttgttt ttggcagcta agaatttatc agatgctatt
 901   ttactttcag atatcctaag agtaaatact gaaataacta aggctcccct atcagcttca
 961   atgattaaac gctacgatga acatcatcaa gacttgactc ttttaaaagc tttagttcga
1021   caacaacttc cagaaaagta taagaaatc ttttttgatc aatcaaaaaa cggatatgca
1081   ggttatattg atgggggagc tagccaagaa gaatttata aatttatcaa accaattta
1141   gaaaaaatgg atggtactga ggaattattg gtgaaactaa atcgtgaaga tttgctgcgc
1201   aagcaacgga cctttgacaa cggctctatt ccccatcaaa ttcacttggg tgagctgcat
1261   gctatttga aagacaaga agactttat ccattttaa aagacaatcg tgaagatt
1321   gaaaaatct tgactttcg aattccttat tatgttggtc cattggcgcg tggcaatagt
1381   cgttttgcat ggatgactcg gaagtctgaa gaaacaatta ccccatggaa ttttgaagaa
```

-continued

```
1441  gttgtcgata aaggtgcttc agctcaatca tttattgaac gcatgacaaa ctttgataaa
1501  aatcttccaa atgaaaaagt actaccaaaa catagtttgc tttatgagta ttttacggtt
1561  tataacgaat tgacaaaggt caaatatgtt actgaaggaa tgcgaaaacc agcatttctt
1621  tcaggtgaac agaagaaagc cattgttgat ttactcttca aaacaaatcg aaaagtaacc
1681  gttaagcaat taaaagaaga ttatttcaaa aaaatagaat gttttgatag tgttgaaatt
1741  tcaggagttg aagatagatt taatgcttca ttaggtacct accatgattt gctaaaaatt
1801  attaaagata aagattttt ggataatgaa gaaaatgaag atatcttaga ggatattgtt
1861  ttaacattga ccttatttga agatagggag atgattgagg aaagacttaa aacatatgct
1921  cacctctttg atgataaggt gatgaaacag cttaaacgtc gccgttatac tggttgggga
1981  cgtttgtctc gaaaattgat taatggtatt agggataagc aatctggcaa aacaatatta
2041  gattttttga aatcagatgg ttttgccaat cgcaattta tgcagctgat ccatgatgat
2101  agtttgacat taaagaaga cattcaaaaa gcacaagtgt ctggacaagg cgatagttta
2161  catgaacata ttgcaaattt agctggtagc cctgctatta aaaaaggtat tttacagact
2221  gtaaaagttg ttgatgaatt ggtcaaagta atggggcggc ataagccaga aaatatcgtt
2281  attgaaatgg cacgtgaaaa tcagacaact caaaagggcc agaaaaattc gcgagagcgt
2341  atgaaacgaa tcgaagaagg tatcaaagaa ttaggaagtc agattcttaa agagcatcct
2401  gttgaaaata ctcaattgca aaatgaaaag ctctatctct attatctcca aaatggaaga
2461  gacatgtatg tggaccaaga attagatatt aatcgtttaa gtgattatga tgtcgatcac
2521  attgttccac aaagtttcct taaagacgat tcaatagaca ataaggtctt aacgcgttct
2581  gataaaaatc gtggtaaatc ggataacgtt ccaagtgaag aagtagtcaa aaagatgaaa
2641  aactattgga gacaacttct aaacgccaag ttaatcactc aacgtaagtt tgataattta
2701  acgaaagctg aacgtggagg tttgagtgaa cttgataaag ctggttttat caaacgccaa
2761  ttggttgaaa ctcgccaaat cactaagcat gtggcacaaa ttttggatag tcgcatgaat
2821  actaaatacg atgaaaatga taaacttatt cgagaggtta aagtgattac cttaaaatct
2881  aaattagttt ctgacttccg aaaagatttc caattctata agtacgtga gattaacaat
2941  taccatcatg cccatgatgc gtatctaaat gccgtcgttg gaactgcttt gattaagaaa
3001  tatccaaaac ttgaatcgga gtttgtctat ggtgattata agtttatga tgttcgtaaa
3061  atgattgcta agtctgagca agaaataggc aaagcaaccg caaaatattt cttttactct
3121  aatatcatga acttcttcaa aacagaaatt acacttgcaa atggagagat tcgcaaacgc
3181  cctctaatcg aaactaatgg ggaaactgga gaaattgtct gggataaagg gcgagatttt
3241  gccacagtgc gcaaagtatt gtccatgccc caagtcaata ttgtcaagaa aacagaagta
3301  cagacaggcg gattctccaa ggagtcaatt ttaccaaaaa gaaattcgga caagcttatt
3361  gctcgtaaaa agactgggga tccaaaaaaa tatggtggtt ttgatagtcc aacggtagct
3421  tattcagtcc tagtggttgc taaggtggaa aaagggaaat cgaagaagtt aaaatccgtt
3481  aaagagttac tagggatcac aattatggaa agaagttcct ttgaaaaaaa tccgattgac
3541  ttttagaag ctaaaggata taaggaagtt aaaaaagact taatcattaa actacctaaa
3601  tatagtcttt ttgagttaga aaacggtcgt aaacggatgc tggctagtgc cggagaatta
3661  caaaaaggaa atgagctggc tctgccaagc aaatatgtga atttttata tttagctagt
3721  cattatgaaa agttgaaggg tagtccagaa gataacgaac aaaaacaatt gtttgtggag
3781  cagcataagc attatttaga tgagattatt gagcaaatca gtgaattttc taagcgtgtt
```

```
3841  attttagcag atgccaattt agataaagtt cttagtgcat ataacaaaca tagagacaaa 3901  ccaatacgtg aacaagcaga aaatattatt catttattta cgttgacgaa tcttggagct 3961  cccgctgctt ttaaatattt tgatacaaca attgatcgta aacgatatac gtctacaaaa 4021  gaagttttag atgccactct tatccatcaa tccatcactg gtctttatga aacacgcatt 4081  gatttgagtc agctaggagg tgactga
```

By "Cpf1 (CRISPR associated protein Cpf1)" is meant a polypeptide or fragment thereof having at least about 85% amino acid identity to GenBank Accession No. AJI61006.1 and having RNA binding activity, DNA binding activity, and/or DNA cleavage activity (e.g., endonuclease or nickase activity). An exemplary Cas9 polypeptide sequence is provided below.

```
                                                          (SEQ ID NO: 18)
   1  msiyqefvnk yslsktlrfe lipqgktlen ikarglildd ekrakdykka kqiidkyhqf 61  fieeilssvc isedllqnys dvyfklkksd ddnlqkdfks akdtikkqis eyikdsekfk 121  nlfnqnlida kkgqesdlil wlkqskdngi elfkansdit didealeiik sfkgwttyfk 181  gfhenrknvy ssndiptsii yrivddnlpk flenkakyes lkdkapeain yeqikkdlae 241  eltfdidykt sevnqrvfsl devfeianfn nylnqsgitk fntiiggkfv ngentkrkgi 301  neyinlysqq indktlkkyk msvlfkqils dtesksfvid kleddsdvvt tmqsfyeqia 361  afktveeksi ketlsllfdd lkaqkldlsk iyfkndkslt dlsqqvfddy svigtavley 421  itqqiapknl dnpskkeqel iakktekaky lsletiklal eefnkhrdid kqcrfeeila 481  nfaaipmifd eiaqnkdnla qisikyqnqg kkdllqasae ddvkaikdll dqtnnllhkl 541  kifhisqsed kanildkdeh fylvfeecyf elanivplyn kirnyitqkp ysdekfklnf 601  enstlangwd knkepdntai lfikddkyyl gvmnkknnki fddkaikenk gegykkivyk 661  llpgankmlp kvffsaksik fynpsedilr irnhsthtkn gspqkgyekf efniedcrkf 721  idfykqsisk hpewkdfgfr fsdtqrynsi defyrevenq gykltfenis esyidsvvnq 781  gklylfqiyn kdfsayskgr pnlhtlywka lfdernlqdv vyklngeael fyrkqsipkk 841  ithpakeaia nknkdnpkke svfeydlikd krftedkfff hcpitinfks sgankfndei 901  nlllkekand vhilsidrge rhlayytlvd gkgniikqdt fniigndrmk tnyhdklaai 961  ekdrdsarkd wkkinnikem kegylsqvvh eiaklvieyn aivvfedlnf gfkrgrfkve 1021  kqvyqklekm lieklnylvf kdnefdktgg vlrayqltap fetfkkmgkq tgiiyyvpag 1081  ftskicpvtg fvnqlypkye sysksqeffs kfdkicynld kgyfefsfdy knfgdkaakg 1141  kwtiasfgsr linfrnsdkn hnwdtrevyp tkelekllkd ysieyghgec ikaaicgesd 1201  kkffakltsv lntilqmrns ktgteldyli spvadvngnf fdsrqapknm pqdadangay 1261  higlkglmll griknnqegk klnlviknee yfefvqnrnn
```

"Cpf1 function" can be defined by any of a number of assays including, but not limited to, fluorescence polarization-based nucleic acid bind assays, fluorescence polarization-based strand invasion assays, transcription assays, EGFP disruption assays, DNA cleavage assays, and/or Surveyor assays, for example, as described herein.

By "Cpf1 nucleic acid molecule" is meant a polynucleotide encoding a Cpf1 polypeptide or fragment thereof. An exemplary Cpf1 nucleic acid molecule sequence is provided at GenBank Accession No. CP009633, nucleotides 652838-656740 and is shown below.

(SEQ ID NO: 19)

```
   1  atgtcaatttatcaagaatttgttaataaatatagtttaagtaaaactctaagatttgag
  61  ttaatcccacagggtaaaacacttgaaaacataaaagcaagaggtttgattttagatgat
 121  gagaaaagagctaaagactacaaaaaggctaaacaataattgataaatatcatcagttt
 181  tttatagaggagatattaagttcggtttgtattagcgaagatttattacaaaactattct
 241  gatgtttattttaaacttaaaaagagtgatgatgataatctacaaaaagattttaaaagt
 301  gcaaaagatacgataaagaaacaaatatctgaatatataaaggactcagagaaatttaag
 361  aatttgtttaatcaaaaccttatcgatgctaaaaaagggcaagagtcagatttaattcta
 421  tggctaaagcaatctaaggataatggtatagaactatttaaagccaatagtgatatcaca
 481  gatatagatgaggcgttagaaataatcaaatcttttaaaggttggacaacttattttaag
 541  ggttttcatgaaaatagaaaaaatgtttatagtagcaatgatattcctacatctattatt
 601  tataggatagtagatgataatttgcctaaatttctagaaaataaagctaagtatgagagt
 661  ttaaaagacaaagctccagaagctataaactatgaacaaattaaaaaagatttggcagaa
 721  gagctaacctttgatattgactacaaaacatctgaagttaatcaaagagttttttcactt
 781  gatgaagtttttgagatagcaaactttaataattatctaaatcaaagtggtattactaaa
 841  tttaatactattattggtggtaaatttgtaaatggtgaaaatacaaagagaaaaggtata
 901  aatgaatatataaatctatactcacagcaaataaatgataaaacactcaaaaaatataaa
 961  atgagtgttttatttaagcaaattttaagtgatacagaatctaaatcttttgtaattgat
1021  aagttagaagatgatagtgatgtagttacaacgatgcaaagtttttatgagcaaatagca
1081  gcttttaaaacagtagaagaaaaatctattaaagaaacactatctttattatttgatgat
1141  ttaaaagctcaaaaacttgatttgagtaaaatttattttaaaaatgataaatctcttact
1201  gatctatcacaacaagttttgatgattatagtgttattggtacagcggtactagaatat
1261  ataactcaacaaatagcacctaaaaatcttgataaccctagtaagaaagagcaagaatta
1321  atagccaaaaaaactgaaaaagcaaaatacttatctctagaaactataaagcttgcctta
1381  gaagaatttaataagcatagagatatagataaacagtgtaggtttgaagaaatacttgca
1441  aactttgcggctattccgatgatatttgatgaaatagctcaaaacaaagacaatttggca
1501  cagatatctatcaaatatcaaatcaaggtaaaaaagacctacttcaagctagtgcggaa
1561  gatgatgttaaagctatcaaggatcttttagatcaaactaataatctcttacataaacta
1621  aaaatatttcatattagtcagtcagaagataaggcaaatattttagacaaggatgagcat
1681  ttttatctagtatttgaggagtgctactttgagctagcgaatatagtgcctctttataac
1741  aaaattagaaactatataactcaaaagccatatagtgatgagaaatttaagctcaatttt
1801  gagaactcgacttttggctaatggttgggataaaaataaagagcctgacaatacggcaatt
1861  ttatttatcaaagatgataaatattatctgggtgtgatgaataagaaaaataacaaaata
1921  tttgatgataaagctatcaaagaaaataaaggcgagggttataaaaaaattgtttataaa
1981  cttttacctggcgcaaataaaatgttacctaaggttttcttttctgctaaatctataaaa
2041  ttttataatcctagtgaagatatacttagaataagaaatcattccacacatacaaaaaat
2101  ggtagtcctcaaaaaggatatgaaaaatttgagtttaatattgaagattgccgaaaattt
2161  atagattttataaacagtctataagtaagcatccggagtggaaagattttggatttaga
2221  ttttctgatactcaaagatataattctatagatgaattttatagagaagttgaaaatcaa
2281  ggctacaaactaactttttgaaaatatatcagagagctatattgatagcgtagttaatcag
2341  ggtaaattgtaccctattccaaatctataataaagattttttcagcttatagcaaagggcga
```

```
-continued
2401  ccaaatctacatactttatattggaaagcgctgtttgatgagagaaatcttcaagatgtg 2461  gtttataagctaaatggtgaggcagagcttttttatcgtaaacaatcaatacctaaaaaa 2521  atcactcacccagctaaagaggcaatagctaataaaaacaaagataatcctaaaaaagag 2581  agtgttttttgaatatgatttaatcaaagataaacgctttactgaagataagttttttcttt 2641  cactgtcctattacaatcaatttttaaatctagtggagctaataagtttaatgatgaaatc 2701  aatttattgctaaaagaaaaagcaaatgatgttcatatattaagtatagatagaggtgaa 2761  agacatttagcttactatactttggtagatggtaaaggcaatatcatcaaacaagatact 2821  ttcaacatcattggtaatgatagaatgaaaacaaactaccatgataagcttgctgcaata 2881  gagaaagatagggattcagctaggaaagactggaaaaagataaataacatcaaagagatg 2941  aaagagggctatctatctcaggtagttcatgaaatagctaagctagttatagagtataat 3001  gctattgtggtttttgaggatttaaattttggatttaaaagagggcgtttcaaggtagag 3061  aagcaggtctatcaaaagttagaaaaaatgctaattgagaaactaaactatctagttttc 3121  aaagataatgagtttgataaaactgggggagtgcttagagcttatcagctaacagcacct 3181  tttgacttttaaaaagatgggtaaacaaacaggtattatctactatgtaccagctggt 3241  tttacttcaaaaatttgtcctgtaactggttttgtaaatcagttatatcctaagtatgaa 3301  agtgtcagcaaatctcaagagttctttagtaagtttgacaagatttgttataaccttgat 3361  aagggctattttgagtttagttttgattataaaaactttggtgacaaggctgccaaaggc 3421  aagtggactatagctagctttgggagtagattgattaactttagaaattcagataaaaat 3481  cataattgggatactcgagaagtttatccaactaaagagttggagaaattgctaaaagat 3541  tattctatcgaatatgggcatggcgaatgtatcaaagcagctatttgcggtgagagcgac 3601  aaaaagttttttgctaagctaactagtgtcctaaatactatcttacaaatgcgtaactca 3661  aaaacaggtactgagttagattatctaatttcaccagtagcagatgtaaatggcaatttc 3721  tttgattcgcgacaggcgccaaaaaatatgcctcaagatgctgatgccaatggtgcttat 3781  catattgggctaaaaggtctgatgctactaggtaggatcaaaaataatcaagagggcaaa 3841  aaactcaatttggttatcaaaaatgaagagtattttgagttcgtgcagaataggaataac 3901  taa
```

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Non-limiting examples of optional substituents as referred to herein include halogen, alkyl, aralkyl, heteroalkyl, alkenyl, alkynyl, cycloalkyl, hydroxyl, alkoxy, amino, amido, nitro, cyano, amido, carbonyl, carboxyl, silyl, ether, alkylthio, sulfonyl, sulfonamido, ketone, aldehyde, ester, heterocyclyl, aryl, and heteroaryl.

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalented bound to a carbon atom in the chain or backbone, as in "oxo").

In some embodiments, any hydrocarbon or substituted hydrocarbon disclosed herein may be substituted with one or more substituents X, where X is independently selected at each occurrence from one or more (e.g., 1-20) heteroatoms or one or more (e.g., 1-10) heteroatom-containing groups, where, for example, X may be selected from —F; —Cl; —Br; —I; —OH; —OR*; —NH$_2$; —NHR*; —N(R*)$_2$; —N(R*)$_3{}^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —C(=O)—R*; —CHO; —CO$_2$H; —CO$_2$—; —CO$_2$R*; —C(=O)—S—R*; —O—(C=O)—H; —O—(C=O)—R*; —S—C(=O)—R*; —(C=O)—NH$_2$; —C(=O)—N(R*)$_2$; —NH—(C=O)—R*; —NH—(C=O)—R*; —N(R*)—C(=O)—R*; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1\text{-}2}$—R*; —O—S(=O)$_2$—R*; —S(=O)$_2$—OR*; —N(R*)—S(=O)$_2$—R*; —S(=O)$_2$—N(R*)$_2$; —O—SO$_3$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1\text{-}6}$CH$_3$; —PR*$_2$; —O—P(=O)(OR*)$_2$; and —P(=O)(OR*)$_2$; where, independently at each occurrence, R* may be H or a $C_{1\text{-}10}$ or $C_{1\text{-}8}$ or $C_{1\text{-}6}$ or $C_{1\text{-}4}$ hydrocarbon, including without limitation alkyl, alkenyl, alkynyl, aryl (e.g., phenyl), alkyl-aryl (e.g., benzyl), aryl-alkyl (e.g., toluyl), etc. In other embodiments, X may comprise a $C_1$-$C_8$ or $C_1$-$C_6$ or $C_2$-$C_4$ perfluoroalkyl. In other embodiments, X may a $C_1$-$C_8$ or $C_2$-$C_6$ or $C_3$-$C_5$ heterocycle (e.g., heteroaryl radical). The term "halo" or "halogen" refers to any radical of fluorine, chlorine, bromine or iodine. In some embodiments, X is independently selected at each occurrence from —OH, —SH, —NH$_2$; —N(R*)$_2$; —F, and —Cl.

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As used herein, the term "straight chain $C_{n\text{-}m}$ alkylene," employed alone or in combination with other terms, refers to a non-branched divalent alkyl linking group having n to m carbon atoms. Any atom can be optionally substituted, e.g., by one or more substituents. Examples include methylene (i.e., —CH$_2$—).

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "halothioalkoxy" refer to —O(haloalkyl) and —S(haloalkyl), respectively. The term "sulfhydryl" refers to —SH. As used herein, the term "hydroxyl," employed alone or in combination with other terms, refers to a group of formula —OH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds.

Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N($C_1$-$C_6$ alkyl), NC(O) ($C_1$-$C_6$ alkyl), O, and S; and wherein said heterocyclic ring is optionally substituted with from 1-3 independently selected $R^{a''}$" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The terms "arylcycloalkyl" and "arylheterocyclyl" refer to bicyclic, tricyclic, or other polycyclic ring systems that include an aryl ring fused to a cycloalkyl and heterocyclyl, respectively. Similarly, the terms "heteroarylheterocyclyl," and "heteroarylcycloalkyl" refer to bicyclic, tricyclic, or other polycyclic ring systems that include a heteroaryl ring fused to a heterocyclyl and cycloalkyl, respectively. Any atom can be substituted, e.g., by one or more substituents. For example, arylcycloalkyl can include indanyl; arylheterocyclyl can include 2,3-dihydrobenzofuryl, 1,2,3,4-tetrahydroisoquinolyl, and 2,2-dimethylchromanyl.

The term "vicinal" refers to the configuration in which any two atoms or groups are, respectively, bonded to two adjacent atoms (i.e., the two atoms are directly bonded to one another). The term "geminal" describes a configuration in which any atoms or two functional groups are bonded to the same atom. As used herein, when any two groups are said to together form a ring, unless otherwise indicated, it is meant that a bond is formed between each of said two groups, with the valences of the atoms appropriately adjusted to accommodate at least a bond (e.g., a hydrogen atom may be removed from each group).

The descriptors "C=O" or "C(O)" or "carbonyl" refers to a carbon atom that is doubly bonded to an oxygen atom. "Alkyl carbonyl" has a common formula of R—C(O)— wherein R may be $C_{1-12}$ alkyl, $C_{2-12}$ alkenyl, $C_{2-12}$ alkynyl, $C_{3-12}$ cycloalkyl, $C_{6-12}$ aryl, $C_{3-12}$ heteroaryl, or $C_{3-12}$ heterocyclyl.

The term "oxo" refers to double bonded oxygen which can be a substituent on carbon or other atoms. When oxo is a substituent on nitrogen or sulfur, it is understood that the resultant groups has the structures N→O⁻ and S(O) and $SO_2$, respectively.

As used herein, the term "cyano," employed alone or in combination with other terms, refers to a group of formula —CN, wherein the carbon and nitrogen atoms are bound together by a triple bond. The term "azide" refers to a group of formula —$N_3$. The term "nitro" refers to a group of formula —$NO_2$. The term "amine" includes primary (—$NH_2$), secondary (—NHR), tertiary (—NRR'), and quaternary (—N⁺RR'R") amine having one, two or three independently selected substituents such as straight chain or branched chain alkyl, alkenyl, alkynyl, cycloalkyl, aryl, heteroaryl, heterocycle, and the like.

When any variable (e.g., $R^1$) occurs more than one time in any constituent or formula for a compound, its definition at each occurrence is independent of its definition at every other occurrence. Thus, for example, if a group is shown to be substituted with one or more $R^1$ moieties, then $R^1$ at each occurrence is selected independently from the Markush group recited for $R^1$. Also, combinations of substituents and/or variables are permissible, but only if such combinations result in stable compounds within a designated atom's normal valency.

As used herein, "unsaturated" refers to compounds or structures having at least one degree of unsaturation (e.g., at least one double or triple bond).

The term "acid addition salt" refers to a salt of a compound prepared by reaction of a compound with a mineral or organic acid. For exemplification of pharmaceutically acceptable acid addition salts, see, e.g., Berge, S. M., Bighley, L. D., and Monkhouse, D. C., *J. Pharm. Sci.*, 66:1, 1977. For example, amine compounds are basic in nature and accordingly react with any of a number of inorganic and organic acids to form pharmaceutically acceptable acid addition salts.

Pharmaceutically acceptable acid addition salts can be formed by the reaction of a disclosed compound with an equimolar or excess amount of acid. Alternatively, hemisalts can be formed by the reaction of a compound with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, iso-butyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycolate, tartrate, methanesulfonate, propanesulfonate, naphthalene-1-sulfonate, naphthalene-2-sulfonate, mandalate and the like.

By "agent" is meant any small molecule chemical compound, antibody, nucleic acid molecule, or polypeptide, or fragments thereof.

By "decreases" is meant a negative alteration. Such alterations are by 5%, 10%, 25%, 50%, 75%, 85%, 90% or even by 100% of a reference value.

By "effective amount" is meant the amount of an agent required to ameliorate the symptoms of a condition, disease or disorder relative to an untreated subject or organism. In particular embodiments, the subject or organism expresses an active RNA guided endonuclease polypeptide. The effective amount of active agent(s) used to practice the present invention varies depending upon the manner of administration, the age, body weight, and general health of the subject.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "hybridize" is meant pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "increases" is meant a positive alteration. Such alterations are by 5%, 10%, 25%, 50%, 75%, 85%, 90% or even by 100% of a reference value.

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ═══ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. In some chemical structures, stereocenters may be identified with "wavy" bonds indicating that the stereocenter may be in the R or S configuration, unless otherwise specified. However, stereocenters without a wavy bond (i.e., a "straight" bond) may also be in the (R) or (S) configuration, unless otherwise specified. Compositions comprising compounds may comprise stereocenters which each may independently be in the (R) configuration, the (S) configuration, or racemic mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, a disclosed compound can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds and intermediates made therein are encompassed by the present disclosure. All tautomers of shown or described compounds are also encompassed by the present disclosure.

The terms "pharmaceutical" or "pharmaceutically acceptable", when used herein as an adjective, mean substantially non-toxic and substantially non-deleterious to the subject.

As used herein, "pharmaceutically acceptable carrier" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self-emulsifying drug delivery systems (SEDDS) such as d-ato-copherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

By "pharmaceutical formulation" it is further meant that the carrier, solvent, excipient(s) and/or salt must be compatible with the active ingredient of the formulation (e.g. a disclosed compound). It is understood by those of ordinary skill in this art that the terms "pharmaceutical formulation" and "pharmaceutical composition" are generally interchangeable, and they are so used for the purposes of this application.

By "prodrug" is meant any compound that must undergo bioactivation before exhibiting its intended pharmacological effects. Since prodrugs are known to enhance numerous desirable qualities of pharmaceuticals (e.g., solubility, bioavailability, manufacturing, etc.), the disclosed compounds can be delivered in prodrug form. Thus, both prodrugs of the compounds, methods of delivering the same and compositions containing the same are disclosed herein. Prodrugs are intended to include any covalently bonded carriers that release an active parent drug (compound) in vivo when such prodrug is administered to a subject. Prodrugs are prepared, for example, by modifying functional groups present in the compound in such a way that the modifications are cleaved, either in routine manipulation or in vivo, to the parent compound. Prodrugs include compounds wherein a hydroxyl or amino group is bonded to any group that, when the prodrug is administered to a subject, it cleaves to form a free hydroxyl or free amino group, respectively. Examples of prodrugs include, but are not limited to, acetate, formate, and benzoate derivatives of alcohol and amine functional groups in the disclosed compounds. Examples of prodrugs include, but are not limited to, benzamide derivatives of an amine functional group in the active compound and the like. Other examples of prodrugs include compounds that comprise —NO, —NO$_2$, —ONO, or —ONO$_2$ moieties.

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_{1-8})$alkyl, $(C_{1-12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as [3-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino $(C_{2-3})$alkyl.

Similarly, if a disclosed compound or a pharmaceutically acceptable form of the compound contains an alcohol functional group, a prodrug can be formed by the replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl, and α-aminoacyl, or α-aminoacyl-α-aminoacyl, where each α-aminoacyl group is independently selected from the naturally occurring L-amino acids, —P(O)(OH)$_2$, —P(O)(O$(C_{1-6})$alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_{1-10})$alkyl, $(C_{3-7})$cycloalkyl, benzyl, a natural α-aminoacyl or natural α-aminoacyl-natural-α-aminoacyl, —C(OH)C(O)OY$^1$ wherein Y$^1$ is H, $(C_{1-6})$ alkyl or benzyl, C(OY$^2$)Y$^3$ wherein Y$^2$ is $(C_{1-4})$alkyl and Y$^3$ is $(C_{1-6})$alkyl, carboxy$(C_{1-6})$alkyl, amino$(C_{1-4})$alkyl or mono-N— or di-N,N—$(C_{1-6})$alkylaminoalkyl, —C(Y$^4$)Y$^5$ wherein Y$^4$ is H or methyl and Y$^5$ is mono-N— or di-N,—$(C_{1-6})$alkylamino, morpholino, piperidin-1-yl or pyrrolidin-1-yl.

In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

By "reference" is meant a standard or control condition.
A "reference sequence" is a defined sequence used as a basis for sequence comparison. In one embodiment, the reference sequence is Cas9.

By "small molecule" is meant any chemical compound.
The terms "selecting a subject" or "identifying a subject" are understood as choosing one or more members of a mixed population of individuals based on specific characteristics including, but not limited to, physical symptoms, and/or clinical characteristics as determined by diagnostic methods.

The term "solvate" means a solvent addition form that contains either a stoichiometric or non-stoichiometric amount of solvent. Some compounds have a tendency to trap a fixed molar ratio of solvent molecules in a solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrates.

The term "suitable solvent" refers to any solvent, or mixture of solvents, that may be inert to the ongoing reaction that sufficiently solubilizes the reactants to afford a medium within which to effect the desired reaction.

By "specifically binds" is meant recognizes and binds a polynucleotide or polypeptide of the invention, but which does not substantially recognize and bind other molecules in a sample.

By "subject" is meant an organism, including, but not limited to, a human or non-human mammal, such as a bovine, equine, canine, ovine, or feline; vertebrate; invertebrate, such as an insect; or plant; or any commercially relevant organism.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

Unless specifically stated or obvious from context, as used herein, the term "or" is understood to be inclusive. Unless specifically stated or obvious from context, as used herein, the terms "a", "an", and "the" are understood to be singular or plural. Thus, for example, reference to "an amino acid substitution" includes reference to more than one amino acid substitution.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other features and advantages of the invention will be apparent from the following description of the desirable embodiments thereof, and from the claims.

BRIEF DESCRIPTION OF THE DRAWINGS

FIG. 2A is a plot of normalized FP values for two screening replicates. Hit compounds identified by the FP-assay are circled.

FIG. 2B depicts that stereoisomers of spirocyclicazetidine hit compounds have different $IC_{50}$ in the FP-assay.

FIG. 2C is a graph depicting dose-dependent reduction in FP-signal by the compound BRD3033.

FIG. 2D is a graph depicting dose-dependent reduction in FP-signal by the compound BRD4172.

FIG. 2E is DNA cleavage assay shows inhibition of SpCas9 activity by BRD3033 and BRD4172.

FIG. 2F show dose-dependence inhibition of SpCas9 in DNA cleavage assay by BRD 3033 and BRD4172.

FIG. 7A discloses SEQ ID NOs: 23 and 24, respectively, in order of appearance.

DETAILED DESCRIPTION OF THE INVENTION

Figure 1A:
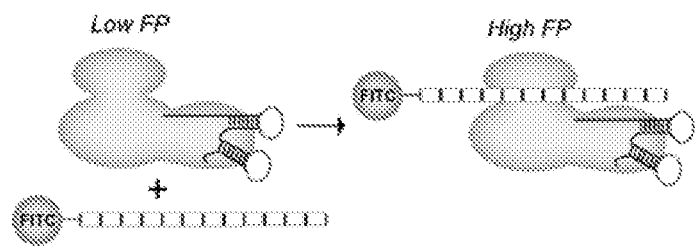
FIG. 1A is a schematic depicting a binding assay that measures Cas9 complex binding to PAM-rich DNA (FP-assay). Fluorescence polarization (FP) increases when [Cas9:guideRNA] complex binds to PAM-rich DNA.

The invention provides compositions and methods for inhibiting the activity of RNA guided endonucleases (e.g., Cas9, Cpf1), and methods of use therefore, as well as to inhibit or prevent Cas9 genome editing. The invention is based, at least in part, on the discovery of small molecule inhibitors of RNA guided endonucleases. As described herein, high-throughput biochemical and cellular assays, and workflows comprising combinations of such assays, were developed for screening and identifying small molecules with the ability to inhibit one or more activities of RNA guided endonucleases. Methods involving small molecule inhibitors of RNA guided endonucleases are useful for the modulation of RNA guided endonuclease activity, including rapid, reversible, dosage, and/or temporal control of RNA guided endonuclease technologies.

CRISPR (Clustered Regularly Interspaced Short Palindromic Repeat)-Cas System

The CRISPR (clustered regularly interspaced short palindromic repeat)-Cas system is an adaptive immune system used by bacteria and archaea to defend against invading phages or mobile genetic elements. Three types of CRISPR-Cas system occur naturally and the type II system was first to be employed for genome editing in mammalian cells. This system employs an RNA-guided endonuclease Cas9, which cleaves double stranded DNA using RuvC and HNH nuclease domains. Cas9 identifies the target sequence by two recognition mechanisms: (i) Watson-Crick base-pairing between the target sequence and gRNA, and (ii) Protospacer Adjacent Motif (PAM) sequence on the target sequence.

Upon target recognition, Cas9 induces double strand breaks in the target gene, which when repaired by non-homologous end joining (NHEJ) can result in frameshift mutations and gene knockdown. Alternatively, homology-directed repair (HDR) at the double-strand break site can allow insertion of the desired sequence.

Cas9 is a spectacular molecular machine with several fascinating attributes. First, the Cas9 employs molecular interactions and recognition between all the three elements of the central dogma—DNA, RNA, and protein. Second, Cas9 unwinds target DNA and facilitates strand invasion without utilizing ATP. Third, Cas9 efficiently induces DNA strand breaks in both prokaryotic and eukaryotic genome despite enormous differences in their genome size, structure, and organization. Finally, unlike transcription factors that often employ 1D diffusion and hopping for target search, Cas9:gRNA complex accomplishes target search by 3D diffusion only.

While Cas9 is a highly efficient molecular machine, its specificity is poor at best. Using genomewide, unbiased identification of double strand breaks enabled by sequencing (GUIDE-seq), Joung and co-workers showed that Cas9's off-targets were present on nearly every chromosome for the on-target gene EMX1. In another specificity study, Zhang and co-workers systematically studied the effect of single-base mismatch between gRNA and target sequence on Cas9 cleavage efficiency for the EMX1 gene. They found that Cas9 tolerated mismatches at PAM-distal sites on gRNA for multiple locations on EMX1 gene. Similar trends in mismatch tolerance were also reported by Doudna and Joung laboratories. Finally, Alt and co-workers have shown that in addition to off-target editing, Cas9 induces chromosomal translocations leading to dicentric chromosomes, which will generate genomic instability. They and others also demonstrated the inverse correlation between Cas9 activity and specificity.

Compounds

The compounds of the invention can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d.ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, Fieser and *Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FTIR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}$F NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

Disclosed herein are inhibitors of Cas9, an RNA-guided DNA endonuclease that naturally occurs in *S. pyogenes* (SpCas9) and *S. aureus* (SaCas9), respectively. Cas9 recognizes foreign DNA using Protospacer Adjacent Motif (PAM) sequence and the base-pairing of the target DNA by the guide RNA (gRNA). The relative ease of inducing targeted strand breaks at any genomic loci by Cas9 has enabled efficient genome editing in multiple cell types and organisms. Cas9 derivatives can also be used as transcriptional activators/repressors.

A challenge posed by Cas9 is that its cleavage selectivity is low. Off-target editing activity can result in undesired undesirable chromosomal translocation. This activity limits the use of Cas9 in a therapeutic setting due to unreliable gene manipulation and lack of ability to control the action of Cas9. The Cas9 inhibitors disclosed herein provide rapid, dosable, and/or temporal control of Cas9 that increases Cas9 specificity and enables external control and manipulation of gene targeting.

Provided herein are compounds having Formula I, II, III, IV, or V which may be used as Cas9 inhibitors in any embodiment of the invention described. Although each of the disclosed inventive compounds having formulas I-V may be disclosed with wedged bonds to indicate the specific stereochemistries, each stereocenter may independently have the R or S configuration, unless reference is given to specific compounds. For any compound having the structure of Formula I-V described herein, $R^1$-$R^4$ may be defined as $R^1$ is selected from Hydrogen, aryl, heteroaryl, —$C_{1-6}$alkyl, —$C_{2-6}$alkenyl, —$C_{2-6}$alkynyl, —$(CH_2)_n$COOH, —$(CH_2)_n$COOC$_{1-6}$lakyl, —$(CH_2)_n$COC$_{1-6}$alkyl, —$(CH_2)_n$OH, —$(CH_2)_n$CONHR, —$(CH_2)_n$NHCOR, —$(CH_2)_n$NHCOC$_{1-6}$alkyl, —$(CH_2)_n$NHSO$_2$R, —$(CH_2)SO_2$NHR, —$(CH_2)SO_2$R, —$(CH_2)SO_2$NHCOR, —$(CH_2)SO_2$NHCOOR, —$(CH_2)_n$SO$_2$NHCONRR, —$(CH_2)$CONHSO$_2$R, —$(CH_2)_n$NHCONRR, —$(CH_2)C_{3-10}$cycloalkyl-COOR, —$SC_{1-6}$alkyl, $SOC_{2-6}$alkyl, $SO_2C_{1-6}$alkyl, —$C_{3-10}$cycloheteroalkenyl, —$C_{3-10}$cycloheteroalkyl, substituted or unsubstituted phenyl, —$(CH_2)_n$-phenyl, —$(CH_2)_n$-aryl and —$(CH_2)$-heteroaryl, —$(CH_2)_nC_{3-10}$cycloalkyl, —$(CH_2)_nC_{3-10}$cycloalkyl-aryl, —$(CH_2)_nC_{3-10}$cycloalkyl-heteroaryl, —$(CH_2)_n$C$_{4-10}$cycloalkenyl, —$(CH_2)_nC_{4-10}$cycloalkenyl-aryl, —$(CH_2)C_{4-10}$cycloalkenyl-heteroaryl, —$(CH_2)C_{2-10}$cycloheteroalkyl, —$(CH_2)_nC_{2-10}$ cycloheteroalkenyl, —$C_{2-6}$alkenyl-alykl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkynyl-$(CH_2)_n$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{3-7}$ cycloheteroalkyl, —$C_{2-6}$alkynyl-$C_{3-7}$ cycloheteroalkenyl, —CONH—$(CH_2)_n$phenyl, wherein n equals to 0 to 6 (i.e., 0, 1, 2, 3, 4, 5, or 6), and each CH$_2$ is unsubstituted or substituted with one or two substituents selected from $C_1$-$C_6$alkyl, —OH, —CN, —CF$_3$, halogen, COOH, COC$_1$-$C_6$alkyl, COOC$_1$-$C_6$alkyl, and —NH$_2$, wherein each NH is unsubstituted or substituted with $C_1$-$C_6$alkyl, —OH, halogen, COOH, COC$_1$-$C_6$alkyl, COOC$_1$-$C_6$alkyl.

In some embodiments, the Cas9 inhibitors are compounds having the structure of Formula (I):

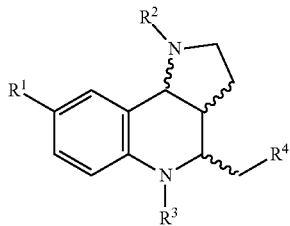
(I)

wherein each wavy bond indicates the presence of a stereocenter, and each stereocenter may be independently at each occurrence in the R or S configuration. In some embodiments, both stereocenters of the five membered fused ring are in the same configuration (i.e., both (R) or both (S)). The groups $R^1$-$R^4$ may be defined as shown below. In some embodiments, the Cas9 inhibiting compounds may have the structure of Formula IA, IB, IC, or ID:

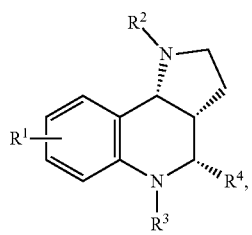
IA

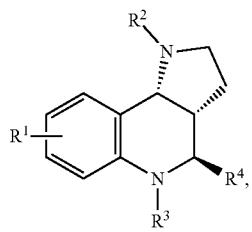
IB

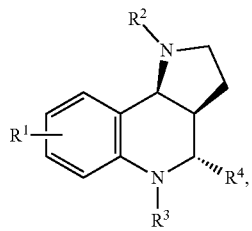
IC

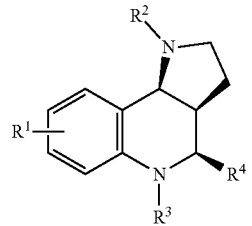
ID wherein $R_1$ is independently selected at each occurrence from hydrogen, —X, —R, -$L_1$-X, or -$L_1$-R; and $R_2$-$R_4$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —$R^L$—NH—C(O)—$(CH_2)_n$—, —$R^L$—NH—S$(O)_2$—$(CH_2)_n$—, —S—, —S(O)—, —S$(O)_2$—; wherein n is independently 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In some embodiments, $R^2$ is a group —$CH_2$—R. In some embodiments, $R^1$-$R^4$ are independently selected at each occurrence from hydrogen, —R, or -$L_1$-R, -$L_1$-X where $L_1$ independently selected at each occurrence from —$(CH_2)_{1-6}$— or —C≡C—. In some embodiments, R is a five or six membered optionally aromatic and optionally substituted ring. In some embodiments, R is selected from phenyl, benzyl, or pyridinyl. In some embodiments, —X is selected from —F, —Cl, —OH, or —OR. In some embodiments, $L_1$ is selected from —$(CH_2)_{1-6}$— or —C≡C—. In some embodiments, R is a $C_{3-6}$ optionally aromatic cyclic hydrocarbon optionally substituted with one or more (e.g., two, three, etc.) functional groups selected from —F, —Cl, —OR* (e.g., —$OCH_3$), or —NH—C(O)O—C$(CH_3)_3$ (i.e. NHBoc). In some embodiments, R is methyl, ethyl, propyl, butyl, ethenyl (i.e., —CH=$CH_2$), or ethynyl (e.g., —C≡CH). In some embodiments, $R^2$ is -$L_1$-X, or -$L_1$-R, where $L_1$ is —$R^L$—NH—C(O)—$(CH_2)_n$—, —$R^L$—NH—S$(O)_2$—$(CH_2)_n$—, or —C(O)—$(CH_2)_n$—. In some embodiments, $R^L$ has the structure:

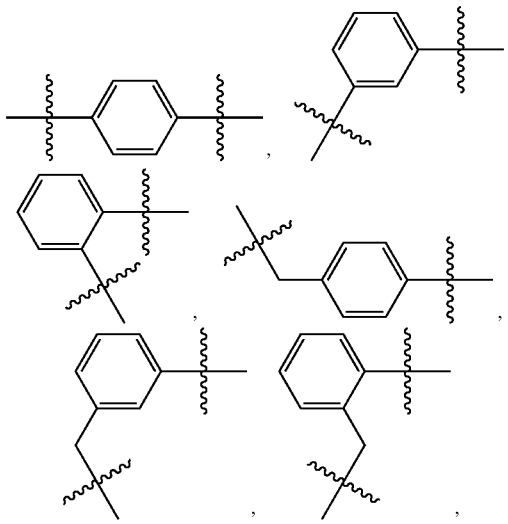

-continued
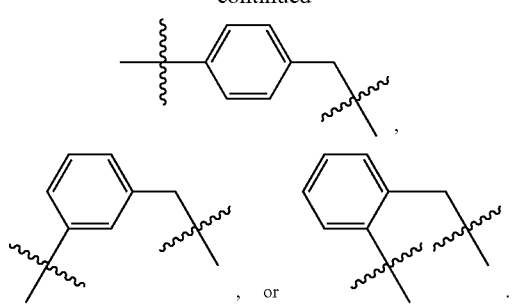
, or
In some embodiments, $R^L$ has the structure:
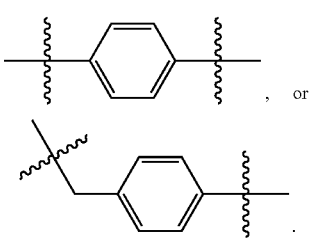
, or
In some embodiments, each $R^1$ is hydrogen. In some embodiments, one of $R^1$ is a group —R, or —$R^L$—R and each other $R^1$ is hydrogen. The Cas9 inhibiting compounds may have the structure:
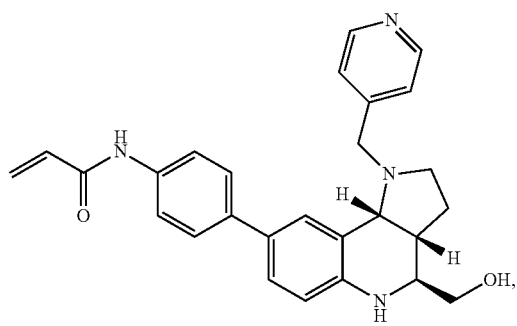
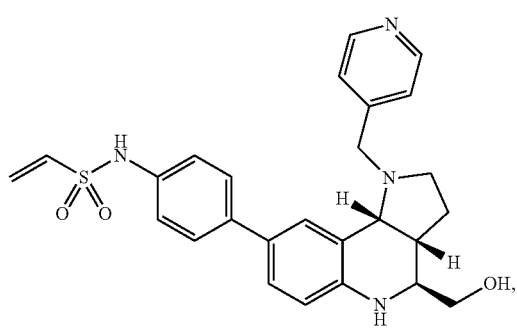
-continued
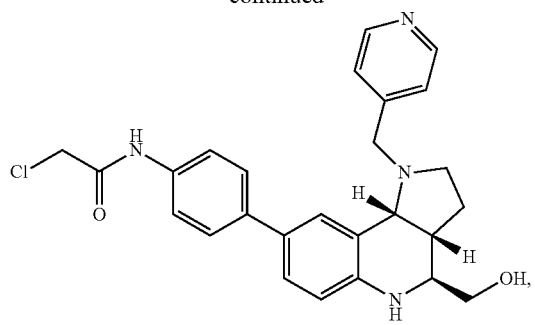
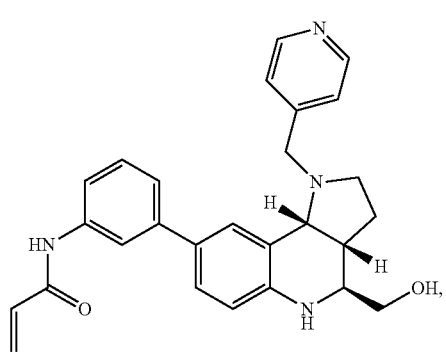
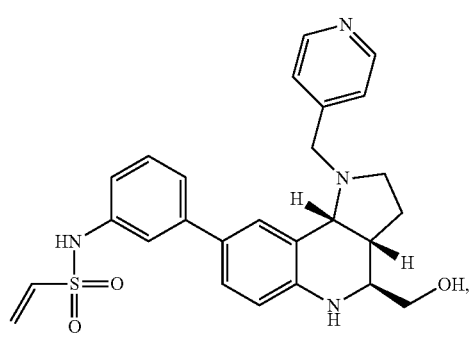
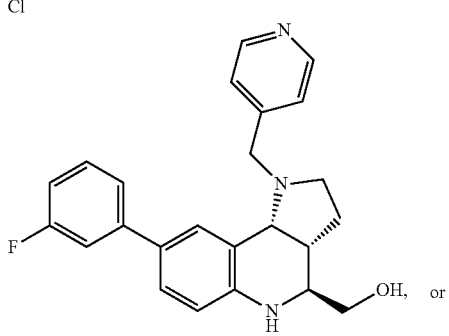
or -continued

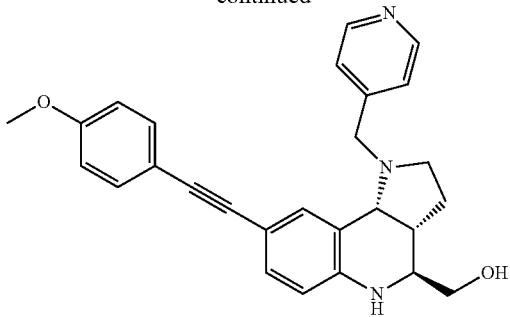

In some embodiments, the Cas9 inhibiting compounds may have the structure of Formula (II):

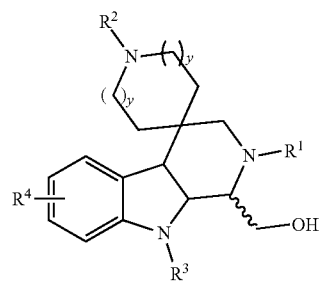

wherein "y" is independently selected at each occurrence from 0 or 1, and the wavy bond indicates the presence of a stereocenter which may be in the (R) or (S) configuration. In some embodiments, "y" is selected from 0 or 1. In some embodiments, the Cas9 inhibiting compounds have the structure of Formula IIA or IIB:

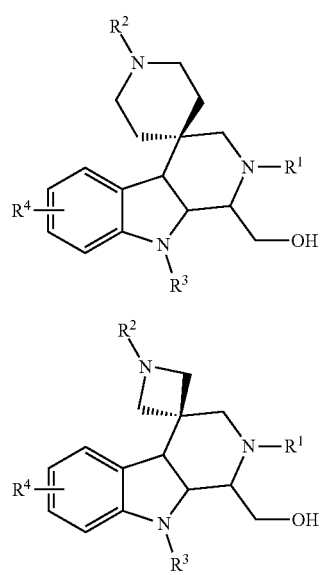

wherein $R_4$ is independently selected at each occurrence from hydrogen, —X, —R, -$L_1$-X, or -$L_1$-R; and
$R^1$-$R^3$ are independently selected from hydrogen, —X, —R, -$L_1$-X, or -$L_1$-R; where X is independently selected at each occurrence from CN, OH, CF$_3$, COOH, OR, OR, NR$_2$, or halogen (e.g., —Cl, —F, —Br, etc.);

$L_1$ is selected from —(CH$_2$)$_n$—, —(CH$_2$)$_n$—C(O)O—, —(CH$_2$)$_n$—C(O)—NH—, —(CH$_2$)$_n$—NH—C(O)—, —(CH$_2$)$_n$—NH—SO$_2$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^L$—, —R$^L$—NH—C(O)—(CH$_2$)$_n$—, —R$^L$—NH—S(O)$_2$—(CH$_2$)$_n$—, —R$^L$—C(O)—O—, —S—, —S(O)—, —S(O)$_2$—; wherein n is independently at each occurrence 0, 1, 2, 3, 4, 5, or 6;

$R^L$ is independently selected at each occurrence from C$_1$-C$_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from C$_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In some embodiments, $R^4$ is selected at each occurrence from hydrogen or —OR. In some embodiments, one of $R^4$ is —OR and each other of $R^4$ is hydrogen. In some embodiments, $R^2$ is a group -$L_1$-R, -$L_1$-X, where $L_1$ is selected from —C(O), —(CH$_2$)$_n$—, —C(O)—(CH$_2$)$_n$—, —CH$_2$)$_n$—C(O)—. In some embodiments, R is a C$_{3-6}$ optionally aromatic cyclic hydrocarbon optionally substituted with one or more (e.g., two, three, etc.) functional groups selected from —F, —Cl, —OR* (e.g., —OCH$_3$), or —NH—C(O)O—C(CH$_3$)$_3$ (i.e. NHBoc). In some embodiments, R is methyl, ethyl, propyl, butyl, ethenyl (i.e., —CH═CH$_2$), or ethynyl (e.g., —C≡CH). In some embodiments, $R^2$ is -$L_1$-X, or -$L_1$-R, where $L_1$ is —R$^L$—NH—C(O)—(CH$_2$)$_n$—, —R$^L$—NH—S(O)$_2$—(CH$_2$)$_n$—, or —C(O)—(CH$_2$)$_n$—. In some embodiments, R$^L$ has the structure:

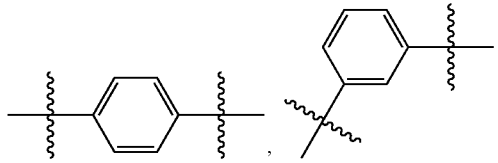

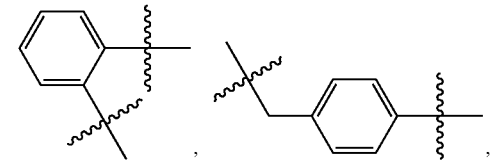

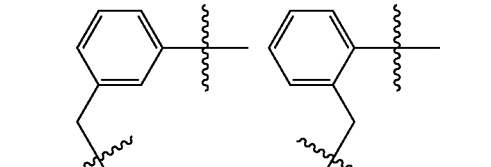

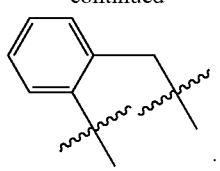
In some embodiments, $R^L$ has the structure:
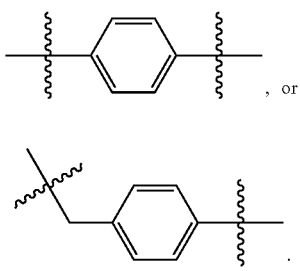
In some embodiments, the Cas9 inhibiting compounds have the structure:
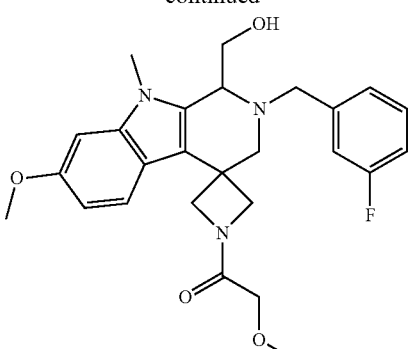
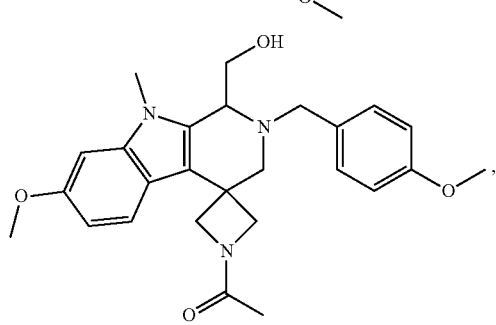
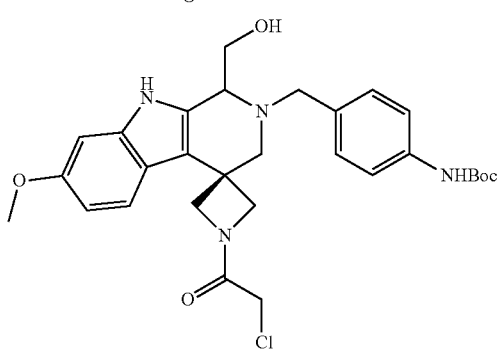
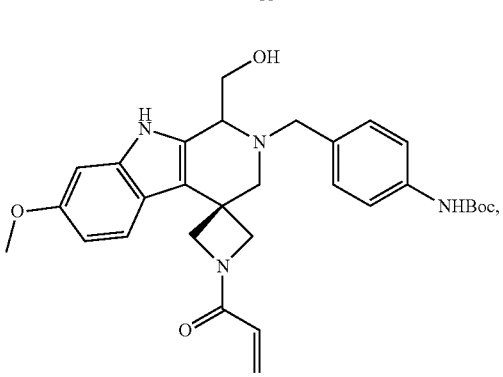
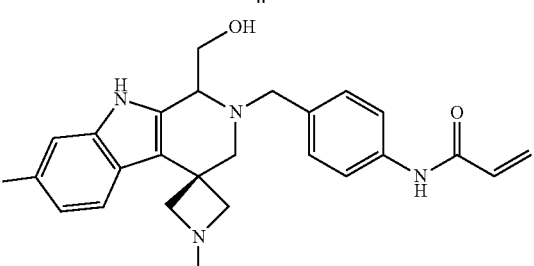
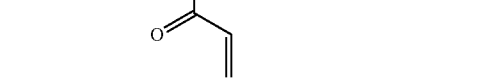

-continued

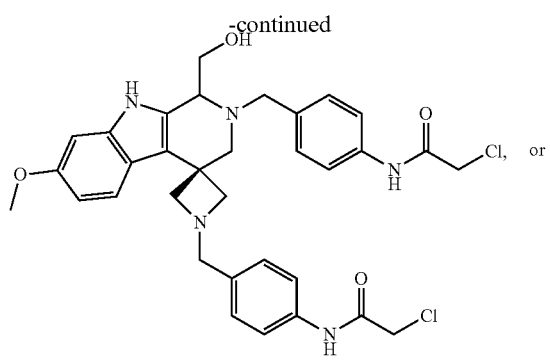

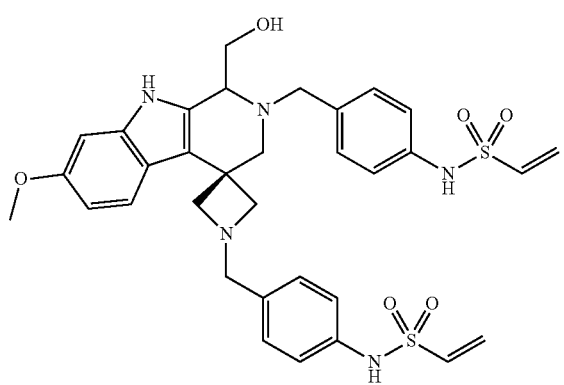

In some embodiments, the Cas9 inhibiting compounds have the structure of Formula (III):

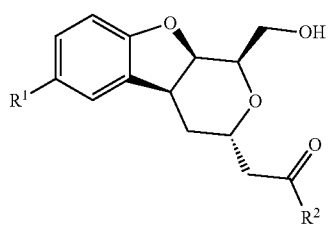

(III)

wherein $R^1$-$R^2$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —S—, —S(O)—, —$S(O)_2$—; wherein n is independently 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof.

In some embodiments, the Cas9 inhibiting compounds have the structure of Formula (IV):

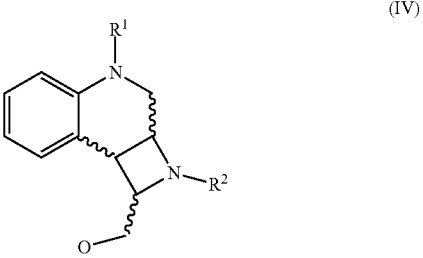

(IV)

wherein each wavy bond may be in the R or the S configuration, $R^1$-$R^2$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —S—, —S(O)—, —$S(O)_2$—; wherein n is independently 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof. In some embodiments, the Cas9 inhibiting compounds have the structure:

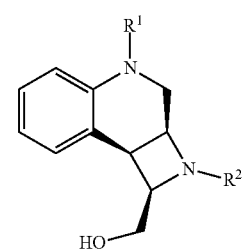

In some embodiments, the Cas9 inhibiting compounds have the structure of Formula V:

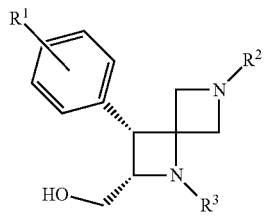

(V)

wherein $R^1$ is independently selected at each occurrence from hydrogen, —X, —R, -$L_1$-X, or -$L_1$-R; and $R^2$-$R^3$ are independently selected from hydrogen, —X, —R, -$L_1$-X, or -$L_1$-R; where X is independently selected at each occurrence from CN, OH, $CF_3$, COOH, OR, OR, $NR_2$, or halogen (e.g., —Cl, —F, —Br, etc.);

$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —S—, —S(O)—, —$S(O)_2$—; wherein n is independently 0, 1, 2, 3, 4, 5, or 6;

$R^L$ is independently selected at each occurrence from $C_1$-$C_{12}$ linear and/or branched and/or cyclic and/or aromatic bivalent radicals (e.g., alkyl, alkenyl, alkynyl, aryl, alkyl-aryl, arayl-alkyl, and combinations thereof); optionally substituted with one or more (e.g., 1-5) groups X and/or with 1-6 heteroatoms selected from O, S, N, P, F, Cl, Br, I; and R is selected from $C_{1-12}$ hydrocarbons (e.g., alkyl, alkenyl, alkynyl, aryl, alkyl-aryl, arayl-alkyl, and combinations thereof), optionally substituted with one or more (e.g., 1-5) groups X and/or with 1-10 heteroatoms selected from O, S, N, P, F, Cl, Br, I, and combinations thereof. In some embodiments, each of $R^1$ is hydrogen. In some embodiments, $R^2$ or $R^3$ is independently -$L_1$-R, where $L_1$ is selected from —C(O)—, or —C(O)—$(CH_2)_n$—. In some embodiments R is a six membered aromatic ring optionally substituted with N. In some embodiments, the Cas9 inhibitors have the structure:

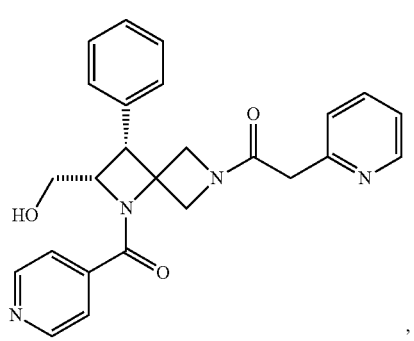

,

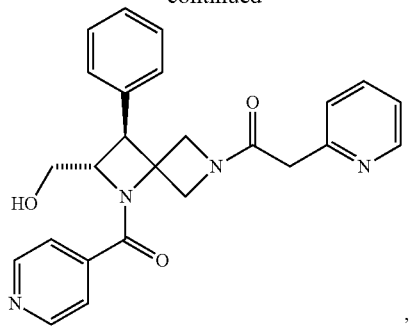

,

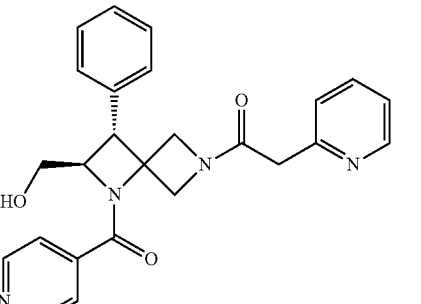

, or

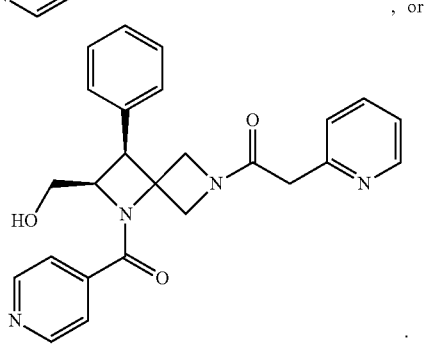

.

The disclosed compounds can be in free base form unassociated with other ions or molecules, or they can be a pharmaceutically acceptable salt, solvate, or prodrug thereof. One aspect provides a disclosed compound or a pharmaceutically acceptable salt. One aspect provides a disclosed compound or a pharmaceutically acceptable salt or solvate thereof. One aspect provides a pharmaceutically acceptable salt of a disclosed compound. One aspect provides a solvate of a disclosed compound. One aspect provides a hydrate of a disclosed compound. One aspect provides a prodrug of a disclosed compound.

The disclosed compounds can be in free base form unassociated with other ions or molecules, or they can be a pharmaceutically acceptable salt, solvate, or prodrug thereof. One aspect provides a disclosed compound or a pharmaceutically acceptable salt. One aspect provides a disclosed compound or a pharmaceutically acceptable salt or solvate thereof. One aspect provides a pharmaceutically acceptable salt of a disclosed compound. One aspect provides a solvate of a disclosed compound. One aspect provides a hydrate of a disclosed compound. One aspect provides a prodrug of a disclosed compound.

Methods of Use

Small molecule inhibitors of RNA guided endonucleases (e.g., Cas9) were developed that have the potential to allow rapid, dosable, and/or temporal control of Cas9 activities. Reports of small-molecule controlled Cas9 activity are present in literature (Senis et al., *Biotechnol J* 2014, 9, 1402-12; Wright et al., *Proc Natl Acad Sci USA*. 2015 March 10; 112(10):2984-9; Gonzalez et al., *Cell Stem Cell* 2014, 15, 215-26; Davis et al., *Nat Chem Biol* 2015, 11, 316-8). However, none of them ensure dosability—the small molecules act merely as inducers of Cas9 activity. Further, most of these small molecule systems are not reversible upon removal of the small molecule (Zetsche et al., *Nat Biotech* 2015, 33, 139-142; Davis et al., *Nat Chem Biol* 2015, 11, 316-8), and therefore, do not allow precise temporal control in transcriptional regulatory technologies.

Small molecule inhibitors of RNA guided endonucleases (e.g., Cas9) have potential therapeutic uses for regulating genome editing technologies involving RNA guided endonucleases. Dosable control of the therapeutic activity of RNA guided endonucleases introduced into a subject or cell of a subject is important for effective genome editing therapeutic strategies. Small molecule inhibitors of RNA guided endonucleases can be administered to a subject undergoing RNA guided endonuclease based gene therapy or any other RNA guided endonuclease based therapy. In certain embodiments, the subject is a human or mammal. Small molecule inhibitors of RNA guided endonucleases eliminate or reduce undesirable off-target editing and chromosomal translocations when present at high concentrations Furthermore, small molecule inhibitors of RNA guided endonucleases can be used to rapidly terminate constitutively active Cas9, following on-target gene-editing.

Small molecule inhibitors of RNA guided endonucleases can also be used to regulate genome editing technologies in other organisms, including invertebrates, plants, and unicellular organisms (e.g., bacteria). Potential uses include regulating gene drives for entomological and agricultural uses. In addition, it is anticipated that Cas9 inhibitors will be valuable probes to understand the role of Cas9 in CRISPR-mediated bacterial immunity (e.g., spacer acquisition) (Nunez et al., *Nature*. 2015 Mar. 12; 519(7542):193-8; Heler et al., *Nature* 2015, 519, 199-202). Along similar lines, Cas9 inhibitors can be deployed for directed evolution of Cas9. It is hypothesized that Cas9 inhibitors will disrupt bacterial immunity against bacteriophages (or toxic DNA) by interfering with the CRISPR-Cas9-based immune surveillance system in bacteria. Akin to the development of antibiotic resistance, bacteria will be forced to evolve Cas9 protein. Accordingly, the inhibitors may also be used as an anti-infective agent.

Formulations

Agents described herein, including analogs thereof, and/or agents discovered to have medicinal value using the methods described herein are useful as a drug for inhibiting RNA guided nucleases (e.g., Cas9, Cpf1). For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms. Generally, amounts will be in the range of those used for other agents used in the treatment of disease.

The disclosed compounds may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus calmatte-guerin, Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The disclosed compounds may be administered by any route known, such as, for example, orally, transdermally, intravenously, cutaneously, subcutaneously, nasally, intramuscularly, intraperitoneally, intracranially, and intracerebroventricularly.

In certain embodiments, disclosed compounds are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than about 0.001 mg/kg or greater than about 50 mg/kg (for example about 50-100 mg/kg) can also be administered to a subject.

In one embodiment, the compound is administered once-daily, twice-daily, or three-times daily. In one embodiment, the compound is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds can be administered on a non-regular basis e.g., whenever symptoms begin. For any compound described herein the effective amount can be initially determined from animal models.

Toxicity and efficacy of the compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices may have a greater effect when practicing the methods as disclosed herein. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds disclosed herein for use in humans. The dosage of such agents lies within a range of circulating concentrations that include the $ED_{50}$ with little or no toxicity. The dosage may vary within this range depending upon the dosage form employed and the route of administration utilized. For any compound used in the disclosed methods, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Multiple doses of the compounds are also contemplated.

The formulations disclosed herein are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more disclosed compounds can be administered to a subject by any mode that delivers the compound(s) to the desired surface, e.g., mucosal, systemic. Administering the pharmaceutical composition of the present disclosure may be accomplished by any means known to the skilled artisan. Disclosed compounds may be administered orally, transdermally, intravenously, cutaneously, subcutaneously, nasally, intramuscularly, intraperitoneally, intracranially, or intracerebroventricularly.

For oral administration, one or more compounds can be formulated readily by combining the active compound(s) with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more disclosed compounds. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. In some aspects for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. In some aspects, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The disclosed compounds can be included in the formulation as fine multiparticulates in the form of granules or pellets of particle size about 1 mm. The formulation of the material for capsule administration could also be as a powder, lightly compressed plugs or even as tablets. The compound could be prepared by compression.

Colorants and flavoring agents may all be included. For example, the compound may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the disclosure. The compound is delivered to the lungs of a mammal while inhaling and traverses across the lung epithelial lining to the blood stream using methods well known in the art.

Contemplated for use in the practice of methods disclosed herein are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of these methods are the Ultravent nebulizer, manufactured by Mallinckrodt, Inc., St. Louis, Missouri; the Acorn II nebulizer, manufactured by Marquest Medical Products, Englewood, Colorado; the Ventolin metered dose inhaler, manufactured by Glaxo Inc., Research Triangle Park, North Carolina; and the Spinhaler powder inhaler, manufactured by Fisons Corp., Bedford, Massachusetts All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to about 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., about 50 to about 90% by weight of the formulation. The compound should most advantageously be prepared in particulate form with an average particle size of less than 10 mm (or microns), such as about 0.5 to about 5 mm, for an effective delivery to the distal lung.

Nasal delivery of a disclosed compound is also contemplated. Nasal delivery allows the passage of a compound to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition solution into a chamber of defined volume, which chamber has an aperture dimensioned to aerosolize and aerosol formulation by forming a spray when a liquid in the chamber is compressed. The chamber is compressed to administer the pharmaceutical composition. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. In some aspects, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (about 1-2% w/v); citric acid and a salt (about 1-3% w/v); boric acid and a salt (about 0.5-2.5% w/v); and phosphoric acid and a salt (about 0.8-2% w/v). Suitable preservatives include benzalkonium chloride (about 0.003-0.03% w/v); chlorobutanol (about 0.3-0.9% w/v); parabens (about 0.01-0.25% w/v) and thimerosal (about 0.004-0.02% w/v).

The pharmaceutical compositions contain an effective amount of a disclosed compound optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds, and with each other, in a manner such that there is no interaction which would substantially impair the desired pharmaceutical efficiency.

Provided herein are methods of synthesizing disclosed compounds. A compound provided herein can be synthesized using a variety of methods known in the art. The schemes and description below depict general routes for the preparation of disclosed compounds.

Fluorescence Polarization-Based Assays

In one aspect, the invention provides an assay that monitors the change in the fluorescence polarization of the fluorophore-labelled PAM-rich target DNA (henceforth called 12PAM-DNA) upon binding to [Cas9:guideRNA] complex. In this assay, the complexation of [Cas9:guideRNA] to 12PAM-DNA shows a dose-dependent increase in fluorophore polarization.

Fluorescence polarization is a useful technique to monitor the interaction between two molecules, including for example, Cas9-gRNA (ribonucleoprotein) complex and target DNA (12PAM). Exemplary fluorophore-labelled PAM-rich target DNA is shown below:

(SEQ ID NO: 1)
5'-GGCTGGACCACGCGGGAAAATCCACCTAGGTGGTTCCTCTTCGG

ATGTTCCATCCTTT/36-FAM-3'

(SEQ ID NO: 2)
3'-CCGACCTGGTGCGCCCTTTTAGGTGGATCCACCAAGGAGAAGCC

TACAAGGTAGGAAA-5'

The technique is based on the change in the tumbling rate or mass after complexation. Following the FP principle, smaller fragment was fluorescently labelled and polarizations were compared before and after complexation in the presence and absence of compounds. While complexation of Cas9:gRNA-DNA showed an enhancement in the FP value, the inhibitors should revert back the enhanced signal intensity. To verify this assumption, Cas9:gRNA-DNA complexation was formed in the presence of excess unlabeled DNA template (with no fluorophore tagging) and measured the FP value. As expected, a sharp decrease in the FP value was observed. Without being bound to theory, this was due at least in part to the displacement of the fluorophore labeled DNA by the cold one. Furthermore, it was investigate whether the displacement by the cold DNA was random or specific. To address this, a competition assay was performed where Cas9-gRNA was incubated with 12PAM DNA template either in the absence or presence of unlabeled DNA with increasing number of PAM density. Interestingly, zero (0) PAM DNA template did not show any considerable inhibition of fluorophore labeled 12PAM binding. In contrast, both 4PAM and 12PAM showed efficient inhibition though the extent was considerably more for 12PAM than the 4PAM DNA. These findings confirmed that the interaction between Cas9:gRNA and DNA template was specific and can be precisely monitored by reading out the FP value. In conclusion, the FP based assay can be used for the Cas9 inhibitor screening assay.

At an initial stage, FP-based screening of 10,000 compounds was performed consisting of structurally diverse scaffolds with vast functional variability. DMSO was used as a negative control while 12PAM cold DNA was used as the competitive positive control. Upon transformation of the large set of data into scatter plot, nearly 0.5% (>3 standard deviation) of the compounds were identified as the potential hits. Interestingly, a large portion of the hit compounds found to have similarity in their molecular scaffold with variation in the stereochemistry and functionality. Numerous structural and functional diversities in the compound library offered a wide scope of medicinal chemistry. Some of the hit compounds like spirocyclic library showed exciting stereocentric dependence of the compound on their activity. To further understand the nature of these hit compounds, their dose dependence on activity was examined. The potential hit compounds showed excellent dose dependent Cas9 inhibition activity with an $IC_{50}$ value as low as 0.6 µM. These finding further re-confirms the validation of the primary assay.

Spinach Transcription Assay

In one aspect, the invention provides a transcription assay to detect the activity of an RNA guided endonuclease. In one embodiment, the level of transcription is suppressed by Cas9 nuclease activity in an in vitro assay. In various embodiments, the transcription assay involves expression of a nucleic acid aptamer that binds a molecular fluorophore to generate a fluorescent signal. Such aptamer-fluorophore combinations are known in the art, including for example, the Spinach aptamer having the sequence (SEQ ID NO: 20)
5'-GGGAGACGCAACUGAAUGAAAUGGUGAAGGACGGGUCCAGGUGU

GGCUGCUUCGGCAGUGCAGCUUGUUGAGUAGAGUGUGAGCUCCGCGU

AACUAGUCGCGUCAC-3' and the fluorophore 4-(3,5-difluoro-4-hydroxybenzylidene)-1,2-dimethyl-1H-imidazol-5-one (DFHBI) (see, e.g., US20120252699 and US20140220560, each of which is incorporated herein in their entirety). In the Spinach assay, Cas9 can cleave the DNA template and thus inhibit in vitro transcription of the nucleic acid aptamer. In certain embodiments, the guide RNA targeting the Spinach aptamer has the sequence (SEQ ID NO: 11)
5'-GCUAUAGGACGCGACCGAAAGUUUUAGAGCUAGAAAUAGCAAGU

UAAAAUAAGGCUAGUCCGUUAUCAACUUGAAAAAGUGGCACCGAGUC

GGUGCUUUU-3'

In the presence of fluorophore, suppression in transcription results in the reduction of RNA aptamer-fluorophore concentration and hence in the fluorescence signal. In vitro transcription reactions may comprise a purified linear DNA template containing a promoter operatively linked to a nucleic acid sequence encoding an RNA aptamer, ribonucleotide triphosphates, a buffer system (e.g., including DTT and magnesium ions, and an appropriate phage RNA polymerase (e.g., T7 polymerase).

EGFP Disruption Assay

In some embodiments, a quantitative human cell-based reporter assay that enables rapid quantitation of targeted nuclease activities is used to characterize off-target cleavage of Cas9-based RNA guided endonucleases. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end-joining (NHEJ) repair of nuclease-induced double-stranded breaks (DSBs).

In one protocol, U2OS.EGFP cells harboring a single integrated copy of an EGFP-PEST fusion gene are cultured (see e.g., Reyon et al., Nat Biotech 30, 460-465 (2012), which is herein incorporated by reference in its entirety). For transfections, 200,000 cells are Nucleofected with gRNA expression plasmid and pJDS246 together with 30 ng of a Td-tomato-encoding plasmid using the SE Cell Line 4D-Nucleofector™ X Kit (Lonza) according to the manufacturer's protocol. Cells are analyzed 2 days post-transfection using a BD LSRII flow cytometer. Transfections for optimizing gRNA/Cas9 plasmid concentration are performed in triplicate and all other transfections are performed in duplicate.

PCR amplification is used for sequence verification of endogenous human genomic sites. PCR reactions are performed using Phusion Hot Start II high-fidelity DNA polymerase (NEB). Loci are amplified using touchdown PCR (98° C., 10 s; 72-62° C., −1° C./cycle, 15 s; 72° C., 30 s] 10 cycles, [98° C., 10 s; 62° C., 15 s; 72° C., 30 s] 25 cycles). Alternatively, PCR for other targets are performed with 35 cycles at a constant annealing temperature of 68° C. or 72° C. and 3% DMSO or 1M betaine, if necessary. PCR products are analyzed on a QIAXCEL capillary electrophoresis system to verify both size and purity. Validated products are treated with ExoSap-IT (Affymetrix) and sequenced by the Sanger method (MGH DNA Sequencing Core) to verify each target site.

SURVEYOR Nuclease Assay

In various embodiments, SURVEYOR nuclease assay is used to assess genome modification (see e.g., US20150356239, which is herein incorporated by reference in its entirety. In one protocol, 293FT cells are transfected with plasmid DNA. Cells were incubated at 37° C. for 72 hours post-transfection prior to genomic DNA extraction. Genomic DNA is extracted using the QuickExtract DNA Extraction Solution (Epicentre) following the manufacturer's protocol. Briefly, pelleted cells are resuspended in QuickExtract solution and incubated at 65° C. for 15 minutes and 98° C. for 10 minutes.

The genomic region flanking the CR1SPR target site for each gene is PCR amplified, and products are purified using QiaQuick Spin Column (Qiagen) following the manufacturer's protocol. 400 ng total of the purified PCR products are mixed with 2 µl 10× Taq DNA Polymerase PCR buffer (Enzytrsaties) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products are treated with SURVEYOR nuclease and SURVEYOR enhancer S (Transgenomics) following the manufacturer's recommended protocol, and analyzed on 4-20% Novex TBE poly-acrylamide gels (Life Technologies). Gels re stained with SYBR Gold DNA stain (Life Technologies) for 30 minutes and imaged with a Gel Doe gel imaging system (Bio-rad). Quantification is based on relative band intensities.

Test Compounds and Extracts

In general, small molecule compounds are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. For example, a library of 8,000 novel small molecules is available, which was created using combinatorial methods of Diversity-Oriented Synthesis (DOS) (Comer et al, Proc Natl Acad Sci USA 108, 6751 (Apr. 26, 2011; Lowe et al, J Org Chem 77, 7187 (Sep. 7, 2012); Marcaurelle et al, J Am Chem Soc 132, 16962 (Dec. 1, 2010))—to investigate chemical compounds not represented in traditional pharmaceutical libraries (Schreiber, S. L. (2000). Science 287, 1964-1969; Schreiber et al, Nat Biotechnol 28, 904 (September, 2010), each of which is herein incorporated by reference in their entirety). Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J Med. Chem.* 37:1233, 1994. Furthermore, if desired, any library or compound is readily modified using standard chemical, physical, or biochemical methods.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:63786382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecules of the invention preferably have a molecular weight below 2,000 daltons, more preferably between 300 and 1,000 daltons, and most preferably between 400 and 700 daltons. It is preferred that these small molecules are organic molecules.

Kits

The present compositions may be assembled into kits or pharmaceutical systems. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Synthesis and Characterization of Compounds

The following Examples illustrate the synthesis of a representative number of compounds and the use of these compounds in the treatment of malaria. Accordingly, the Examples are intended to illustrate but not to limit the disclosure. Additional compounds not specifically exemplified may be synthesized using conventional methods in combination with the methods described herein.

Unless otherwise noted, reactions were performed under an argon atmosphere using freshly dried HPLC grade solvents in flame-dried glassware. All reagents were purchased and used as received from commercial sources or synthesized based on cited procedures. XPhos-Pd-G3, 4-pyridinecarboxaldehyde, palladium on carbon, and sodium triacetoxyborohydride were purchased from Sigma Aldrich; 3-fluorophenylboronic acid was purchased from Oakwood Chemical, and 4-methoxyphenylboronic acid was purchased from Combi-Blocks. All reactions were monitored by thin-layer chromatography (TLC) using Merck Silica gel 60 F254 pre-coated plates (0.25 mm) visualized by UV light at 254 nm. Yields refer to pure compounds after purification by flash column chromatography, unless otherwise noted. Flash column chromatography was performed using silica gel (60 Å mesh, 20-40 μm) on a Teledyne Isco CombiFlash Rf system.

Nuclear magnetic resonance (NMR) spectra were recorded on a Bruker 400 Spectrometer ($^1$H NMR, 400 MHz; $^{13}$C, 100 MHz; Dept-135 Carbon, 100 MHz; $^{19}$F NMR, 376 MHz). Chemical shifts are reported in parts per million (ppm) relative to the solvent used. NMR solvents were purchased from Cambridge Isotope Laboratories, Inc. NMR data were obtained in CDCl$_3$ or DMSO-d$_6$. Data for $^1$H NMR are reported as follows: chemical shift value in ppm, multiplicity (s=singlet, d=doublet, t=triplet, dd=double doublet, and m=multiplet), integration value, and coupling constant value in Hz. Optical rotations were recorded on an Autopol IV automatic Rudolph Research Analytical polarimeter. For each test, 4 mg of the appropriate compound was dissolved in 1 mL chloroform. The reported optical rotations values are averages of five independent measurements at 22° C. (set temperature at 20° C.). Enantiopurity of compounds was determined by analytic supercritical fluid chromatography (SFC) on a Waters UPC2 convergence chromatography system connected to a QDa single quadrupole mass spectrometer with Chiralcel AD-H, AS-H, IC, and OD-H columns using chiral stationary phase with mobile phase A consisting of supercritical carbon dioxide and mobile phase B consisting of isopropanol (IPA) at 45° C. Infrared spectra were recorded on a Nicolet IR 100 FTIR from Thermo Scientific and are reported in frequency of absorption (cm$^{-1}$). Tandem liquid chromatography mass spectrometry (LCMS) was performed on a Waters 2795 separations module with a 3100 mass detector. High-resolution mass-spectra (HRMS) were acquired on an Agilent 1290 Infinity separations module coupled to a 6230 time-of-flight (TOF) mass detector operating in ESI$^+$ or ESI$^-$ mode. "Find-by-Formula" feature in the MassHunter Qualitative Analysis Vb.06.00 was used to confirm mass values, which are averages of three independent measurements.

Compounds may be synthesized using the Synthetic Schemes S1 and S2. References to a substrate number include all compound permutations of that substrate number with alphabetic demarcations. For example, Substrate 12 includes compounds 12a, 12b, 12c, and 12d and Substrate 13 includes compounds 13a-h.

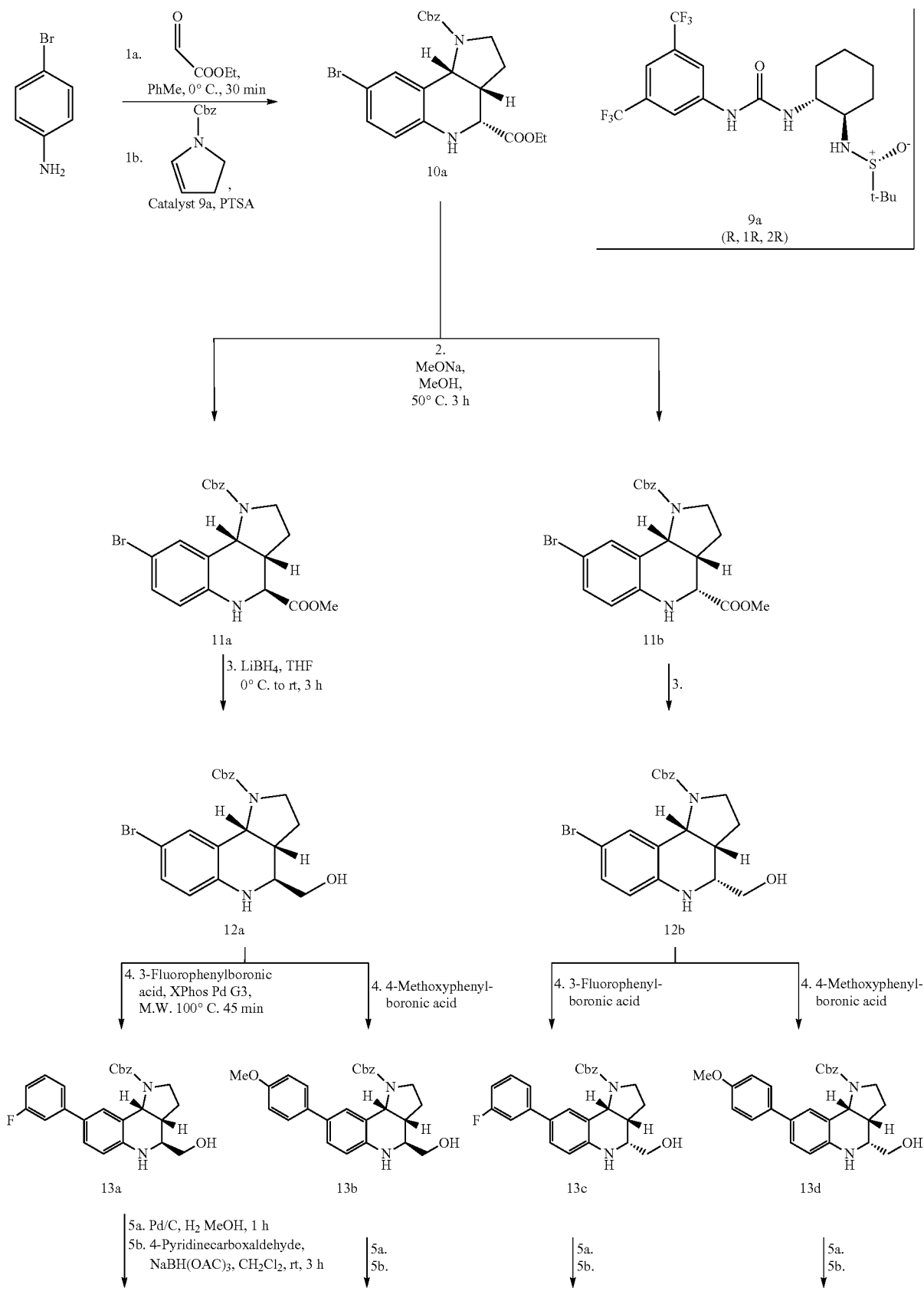

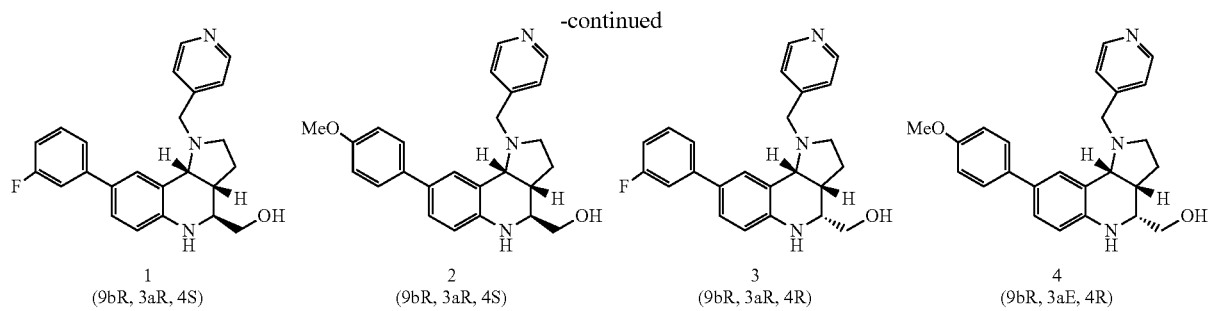
1 (9bR, 3aR, 4S)
2 (9bR, 3aR, 4S)
3 (9bR, 3aR, 4R)
4 (9bR, 3aE, 4R)
Scheme S2, Synthetic scheme for the ((3aS, 9bS)-1-(pyridin-4-ylmethyl)-2,3,3a,4,5,9b-hexahydro-1H-pyrrolo[3,2-c]quinolin-4-yl)methanols 5-8.
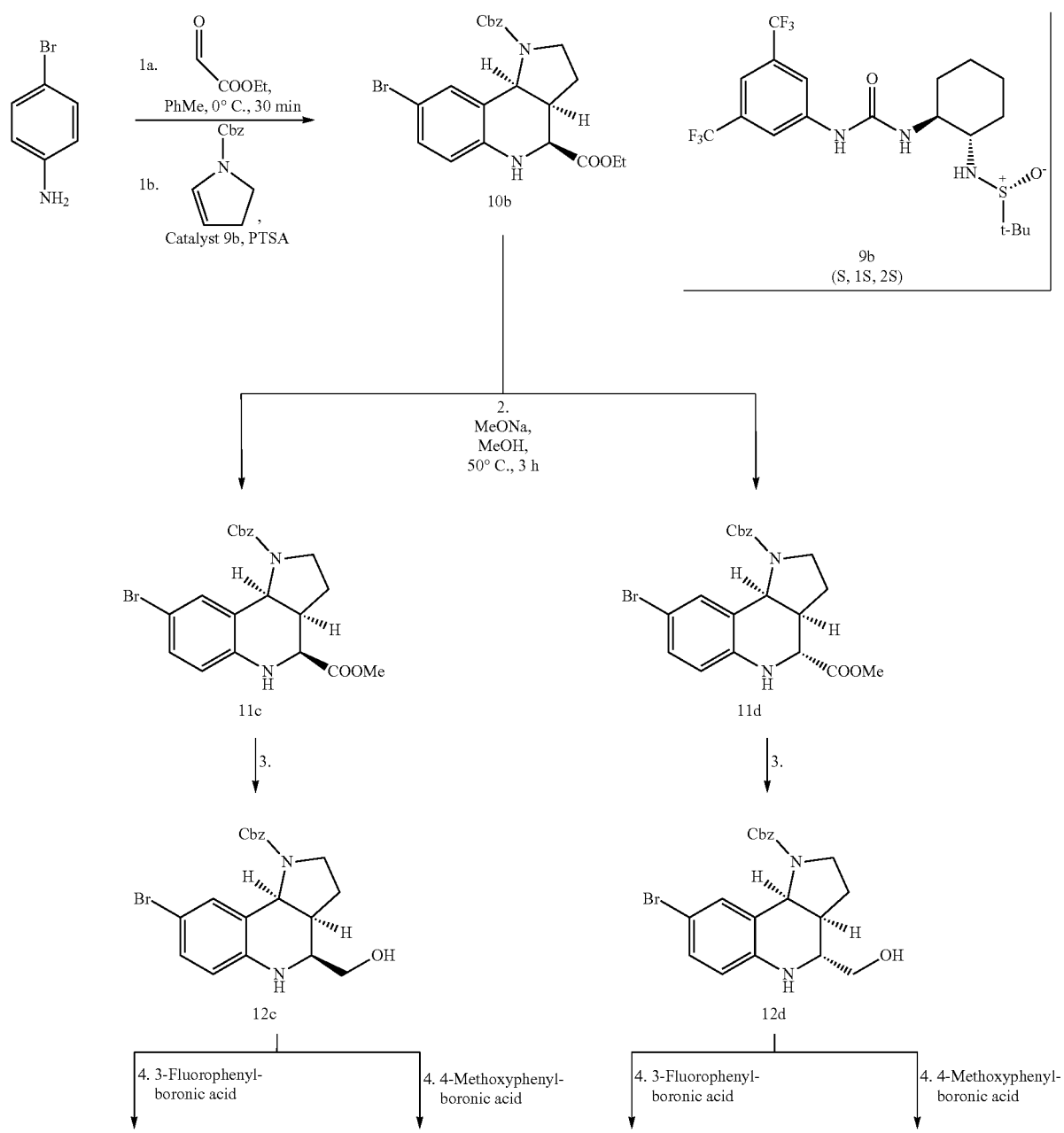

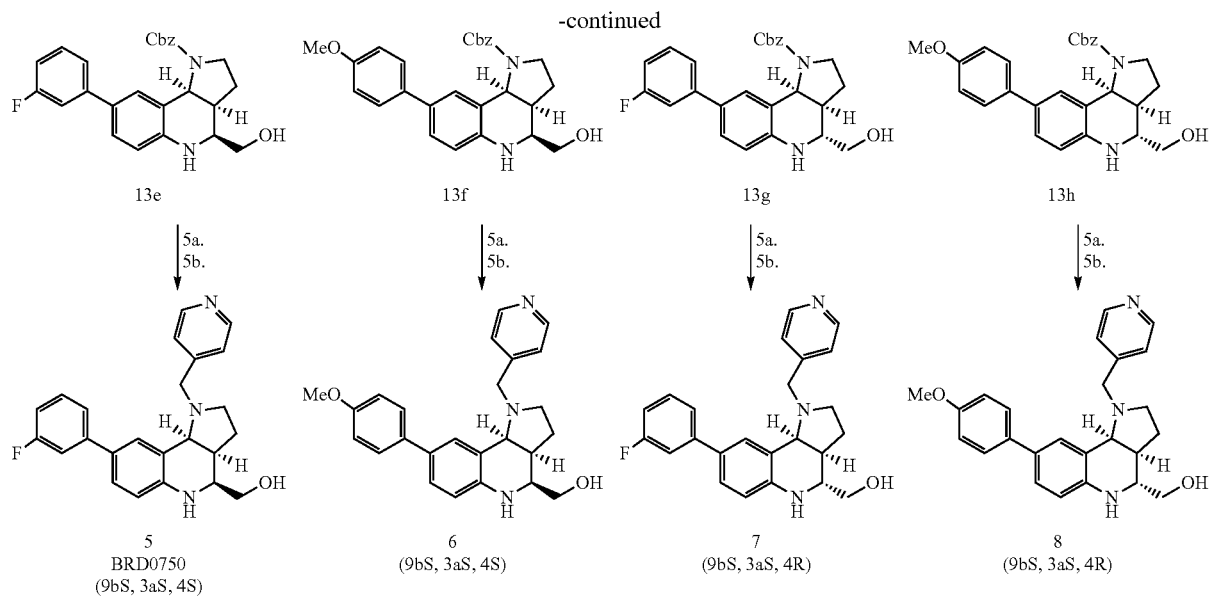

General Procedure A: Microwave-Assisted Suzuki Coupling to Give Hexahydropyrroloquinoline Substrates 13a-h The four isomers of benzyl 8-bromo-4-(hydroxymethyl)-2,3,3a,4,5,9b-hexahydro-1H-pyrrolo[3,2-c]quinoline-1-carboxylate 12a-d were synthesized as described by Jacobsen et al. and Marcaurelle et al. using the chiral urea catalyst 9a or 9b (H. Xu, H. Zhang, E. N. Jacobsen, *Nat. Protoc.* 2014, 9, 1860-1866; B. Gerald, M. W. O'Shea, E. Donckele, S. Kesavan, L. B. Akella, H. Xu, E. N. Jacobsen, L. S. Marcaurelle, *ACS Comb. Sci.* 2012, 14, 621-630). Urea catalysts 9a and 9b were synthesized as described by Jacobsen et al. The obtained NMR spectral data were consistent with those reported in the literature (K. L. Tan, E. N. Jacobsen, *Angew. Chem. Int. Ed.* 2007, 46, 1315-1317.).

The microwave reactions were performed in a Biotage single-mode microwave reactor with a power of 0 to 400 W. A 10-20 mL Biotage microwave reaction vial was charged with the hexahydropyrroloquinoline substrate 12 (1.0 equiv., >90% ee), 3-fluorophenylboronic acid or 4-methoxyphenylboronic acid (1.2 equiv.), potassium carbonate (2.0 equiv.), XPhos Palladium third generation catalyst (5% mol), and a mixture solvent of THF-H$_2$O (v/v, 2/1). The vial was sealed with a septum cap, degassed under high vacuum, and backfilled with an argon atmosphere. The degassing step was repeated three times, and the resulting reaction mixture was microwave irradiated for 45 min at 100° C. The reaction mixture was then cooled to room temperature and filtered through a short pad of Celite. The filtrate was evaporated under vacuum to give crude substrate, usually as off-yellow oily substance, which was purified by flash column chromatography on silica gel eluting with hexane and ethyl acetate (or dichloromethane and methanol).

General Procedure B: Reductive Amination to Give Pyridinylmethylhexahydropyrroloquinoline Compounds 1 to 8

A round-bottom flask was charged with hexahydropyrroloquinoline substrate 13 (1.0 equiv.), palladium on carbon (10% weight), and methanol (0.05 M). The flask was sealed with a rubber septum, degassed under high vacuum, and backfilled with a hydrogen atmosphere. The degassing and hydrogen refilling step was repeated three times, and the resulting reaction mixture was stirred at room temperature for one hour or until the full conversion of the starting material monitored by TLC (methanol in CH$_2$Cl$_2$). The reaction mixture was filtered through a Celite pad and the filtrate was evaporated under vacuum to give the corresponding Cbz-deprotected hexahydropyrroloquinoline substrate.

A flame-dried round-bottom flash was charged with the Cbz-deprotected hexahydropyrroloquinoline substrate (1.0 equiv.) dissolved in dry CH$_2$Cl$_2$ (0.05 M), 4-pyridinecarboxaldehyde (1.5 equiv.), and acetic acid (2.0 equiv.). The reaction mixture was stirred at room temperature for one hour before the adding of NaBH(OAc)$_3$ (3.0 equiv.). The reaction mixture was stirred at room temperature for another three hours or until the full conversion of the starting material monitored by TLC (methanol in CH$_2$Cl$_2$). The reaction mixture was then diluted with CH$_2$Cl$_2$, quenched with a saturated NaHCO$_3$ aqueous solution, and extracted with CH$_2$CL$_2$ (three times). Organic layers were combined, washed with brine, dried over anhydrous Na$_2$SO$_4$, filtered, and concentrated in vacuo to give a crude residue, usually as off-white or light yellow oily substance, which was purified by flash column chromatography on silica gel eluting with hexane and ethyl acetate (or dichloromethane and methanol).

((3aR,4S,9bR)-8-(3-Fluorophenyl)-1-(pyridin-4-ylmethyl)-2,3,3a,4,5,9b-hexahydro-1H-pyrrolo[3,2-c]quinolin-4-yl)methanol (1/BRD7087)

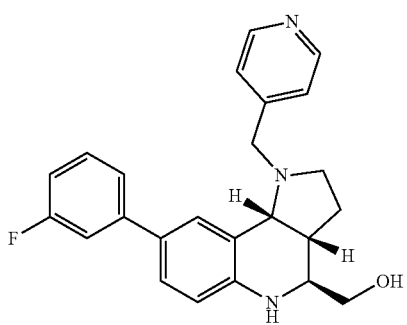 [SMILES: OC[C@H]1Nc2ccc(-c3cccc(F)c3)cc2[C@H]2[C@@H]1CCN2Cc1ccncc1]

Prepared from benzyl (3aR,4S,9bR)-8-(3-fluorophenyl)-4-(hydroxymethyl)-2,3,3a,4,5,9b-hexahydro-1H-pyrrolo[3,2-c]quinoline-1-carboxylate 13a (667 mg, 1.54 mmol) according to General Procedure B. Purification by flash column chromatography eluting with 5% methanol in dichloromethane gave the desired product 3 as a white solid (348 mg, yield 58%).

$R_f$=0.38 (silica gel, 10% methanol in dichloromethane, UV).

$^1$H NMR (400 MHz, CDCl$_3$): δ 8.45 (d, 2H, J=4.8 Hz, aromatic H), 7.35 (d, 2H, J=8.2 Hz, aromatic H), 7.28-7.25 (m, 4H, aromatic H), 7.21 (d, 1H, J=10.5 Hz, aromatic H), 6.97 (t, 1H, J=8.6 Hz, aromatic H), 6.73 (d, 1H, J=8.4 Hz, aromatic H), 4.38 (d, 1H, J=13.8 Hz, CH$_2$OH), 4.01 (d, 1H, J=8.6 Hz, CH$_2$NCH), 3.56-3.53 (m, 2H, NHCHCH and CH$_2$NCH), 3.33 (s, 1H, CH$_2$NCH), 3.27 (d, 1H, J=13.8 Hz, CH$_2$OH), 2.97-2.93 (m, 1H, NCH$_2$CH$_2$), 2.21-2.19 (m, 1H, NCH$_2$CH$_2$), 2.10-2.03 (m, 2H, NCH$_2$CH$_2$ and NHCHCH), 1.65-1.62 (m, 1H, NCH$_2$CH$_2$).

$^{13}$C NMR (100 MHz, CDCl$_3$): δ 164.5 and 162.1 (d, $^1J_{C,F}$=243.4 Hz, aromatic C), 150.0 (aromatic C), 149.1 (2) (pyridinyl C), 144.7 (pyridinyl C), 143.6 and 143.5 (d, $^3J_{C,F}$=7.8 Hz, aromatic C), 130.3 (aromatic C), 130.1 and 130.0 (d, $^3J_{C,F}$=8.8 Hz, aromatic C), 127.8 (aromatic C), 127.6 (aromatic C), 123.6 (2) (pyridinyl C), 121.7 and 121.7 (d, $^4J_{C,F}$=2.8 Hz, aromatic C), 118.3 (aromatic C), 114.6 (aromatic C), 113.0 and 112.8 (d, $^2J_{C,F}$=21.8 Hz, aromatic C), 112.8 and 112.6 (d, $^2J_{C,F}$=21.0 Hz, aromatic C), 64.7 (CH$_2$NCH), 64.1 (CH$_2$NCH), 56.0 (CH$_2$OH), 54.5 (NHCHCH), 51.4 (NCH$_2$CH$_2$), 35.8 (NHCHCH), 25.7 (NCH$_2$CH$_2$).

$^{19}$F NMR (376 MHz, CDCl$_3$): δ −113.5.

[α]$_D^{22}$=+34.40 (c=0.4, CHCl$_3$).

Chiral SFC (AS-H, 1.5 mL/min, MeOH with 0.05% Et$_3$N in CO$_2$, λ=210 nm): $t_R$(minor)=6.4 min, $t_R$(major)=7.0 min.

IR (thin film, cm$^{-1}$): ν$_{max}$ 3413, 2925, 1608, 1522, 1484, 1325, 1261, 1198, 1159, 1077, 869, 819, 782, 752, 693.

LCMS (UV Chromatogram, 210 nm, 2.5 min run): Purity >95% by UV, rt=0.92 min, m/z 390.1 (M+H)$^+$, m/z 434.5 (M+FA-H)$^−$.

HRMS (ESI, m/z): calcd for C$_{24}$H$_{24}$FN$_3$O (M+H)$^+$: 390.1982, found: 390.1976.

((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (2/BRD5779)

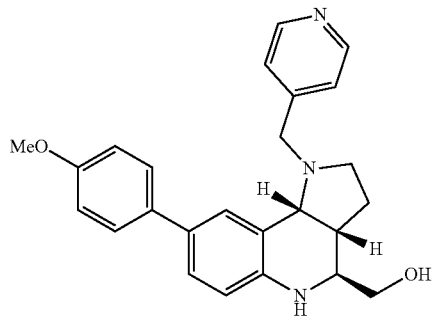 [SMILES: COc1ccc(-c2ccc3c(c2)[C@H]2[C@H](CCN2Cc2ccncc2)[C@@H](CO)N3)cc1]

Prepared from benzyl (3aR,4S,9bR)-4-(hydroxymethyl)-8-(4-methoxyphenyl)-2,3,3a,4,5,9b-hexahydro-1H-pyrrolo[3,2-c]quinoline-1-carboxylate 13b (186 mg, 0.42 mmol) according to General Procedure B. Purification by flash column chromatography eluting with 70% ethyl acetate in hexane gave the desired product 2 as an off-white solid (72 mg, yield 43%).

$R_f$=0.69 (silica gel, 10% methanol in dichloromethane, UV).

$^1$H NMR (400 MHz, CDCl$_3$): δ 8.46 (d, 2H, J=4.9 Hz, aromatic H), 7.44 (d, 2H, J=8.2 Hz, aromatic H), 7.33 (d, 1H, J=8.2 Hz, aromatic H), 7.25-7.24 (m, 3H, aromatic H), 6.97 (d, 2H, J=8.2 Hz, aromatic H), 6.74 (d, 1H, J=8.2 Hz, aromatic H), 4.41 (d, 1H, J=13.8 Hz, CH$_2$OH), 3.99 (d, 1H, J=9.6 Hz, CH$_2$NCH), 3.85 (s, 3H, OCH$_3$), 3.59 (d, 1H, J=9.6 Hz, CH$_2$NCH), 3.53-3.51 (m, 1H, NHCHCH), 3.32 (s, 1H, CH$_2$NCH), 3.25 (d, 1H, J=13.8 Hz, CH$_2$OH), 2.97 (t, 1H, J=9.2 Hz, NCH$_2$CH$_2$), 2.20-2.18 (m, 1H, NCH$_2$CH$_2$), 2.10-2.05 (m, 2H, NCH$_2$CH$_2$ and NHCHCH), 1.66-1.62 (m, 1H, NCH$_2$CH$_2$).

$^{13}$C NMR (100 MHz, CDCl$_3$): δ 158.3 (aromatic C), 149.9 (aromatic C), 149.2 (2) (aromatic C), 143.7 (aromatic C), 134.0 (aromatic C), 130.0 (aromatic C), 129.3 (aromatic C), 127.3 (3) (aromatic C), 123.6 (2) (aromatic C), 118.5 (aromatic C), 114.8 (aromatic C), 114.2 (2) (aromatic C), 64.7 (CH$_2$NCH), 64.1 (CH$_2$NCH), 56.1 (CH$_2$OH), 55.4 (OCH$_3$), 54.5 (NHCHCH), 51.4 (NCH$_2$CH$_2$), 35.9 (NHCHCH), 25.7 (NCH$_2$CH$_2$).

[α]$_D^{22}$=+33.1° (c=0.4, CHCl$_3$).

Chiral SFC (AS-H, 1.5 mL/min, MeOH with 0.05% Et$_3$N in CO$_2$, λ=210 nm): $t_R$(minor)=6.1 min, $t_R$(major)=7.3 min.

IR (thin film, cm$^{-1}$): ν$_{max}$ 3402, 2929, 1614, 1499, 1480, 1246, 1180, 1028, 817, 753.

LCMS (UV Chromatogram, 210 nm, 2.5 min run): Purity >95% by UV, rt=0.84 min, m/z 402.2 (M+H)$^+$, m/z 446.5 (M+FA-H)$^−$.

HRMS (ESI, m/z): calcd for C$_{25}$H$_{27}$N$_3$O$_2$ (M+H)$^+$: 402.2182, found: 402.2172.

((3aR,4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161)

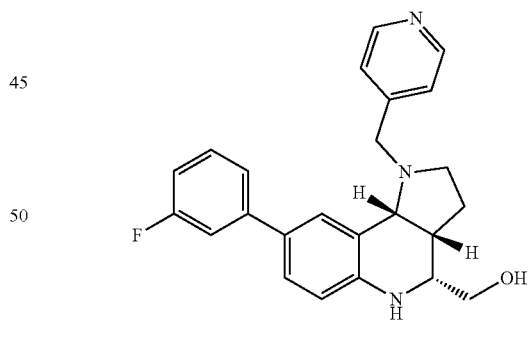

Prepared from benzyl (3aS,4S,9bS)-8-(3-fluorophenyl)-4-(hydroxymethyl)-2,3,3a,4,5,9b-hexahydro-1H-pyrrolo[3,2-c]quinoline-1-carboxylate 13c (276 mg, 0.64 mmol) according to General Procedure B. Purification by flash column chromatography eluting with 5% methanol in dichloromethane gave the desired product 3 as a white solid (66 mg, yield 27%).

$R_f$=0.23 (silica gel, 5% methanol in dichloromethane, UV).

$^1$H NMR (400 MHz, CDCl$_3$): δ 8.55-8.53 (m, 2H, aromatic H), 7.33-7.26 (m, 6H, aromatic H), 7.21 (d, 1H, J=10.8 Hz, aromatic H), 6.97 (t, 1H, J=8.4 Hz, aromatic H), 6.73 (d, 1H, J=8.4 Hz, aromatic H), 4.40 (d, 1H, J=13.5 Hz, CH$_2$OH), 3.90-3.86 (m, 1H, CH$_2$NCH), 3.71-3.65 (m, 2H, NHCHCH and CH$_2$NCH), 3.51-3.47 (m, 2H, CH$_2$NCH and CH$_2$OH), 2.95-2.92 (m, 1H, NCH$_2$CH$_2$), 2.83-2.79 (m, 1H, NCH$_2$CH$_2$), 2.39-2.35 (m, 1H, NCH$_2$CH$_2$), 2.02-1.94 (m, 2H, NHCHCH and NCH$_2$CH$_2$).

$^{13}$C NMR (100 MHz, CDCl$_3$): δ 164.5 and 162.1 (d, $^1J_{C,F}$=244 Hz, aromatic C), 149.5 (2) (pyridinyl C), 148.2 (aromatic C), 145.8 (pyridinyl C), 143.5 and 143.4 (d, $^3J_{C,F}$=7.9 Hz, aromatic C), 130.1 and 130.0 (d, $^3J_{C,F}$=8.2 Hz, aromatic C), 129.4 (aromatic C), 128.8 (aromatic C), 127.5 (aromatic C), 123.9 (2) (pyridinyl C), 121.7 and 121.7 (d, $^4J_{C,F}$=2.3 Hz, aromatic C), 119.4 (aromatic C), 115.2 (aromatic C), 113.0 and 112.8 (d, $^2J_{C,F}$=21.8 Hz, aromatic C), 112.9 and 112.7 (d, $^2J_{C,F}$=21.0 Hz, aromatic C), 64.3 (CH$_2$NCH), 63.3 (CH$_2$NCH), 58.1 (CH$_2$OH), 54.4 (NHCHCH), 51.6 (NCH$_2$CH), 38.1 (NHCHCH), 23.6 (NCH$_2$CH$_2$).

$^{19}$F NMR (376 MHz, CDCl$_3$): δ −113.4.

$[α]_D^{22}$=−29.8° (c=0.4, CHCl$_3$).

Chiral SFC (AS-H, 1.5 mL/min, MeOH with 0.05% Et$_3$N in CO$_2$, λ=210 nm): $t_R$(minor)=6.2 min, $t_R$(major)=6.9 min.

IR (thin film, cm$^1$): $ν_{max}$ 3364, 2917, 1608, 1516, 1480, 1314, 1262, 1193, 1164, 1076, 869, 822, 788, 752, 691.

LCMS (UV Chromatogram, 210 nm, 2.5 min run): Purity >95% by UV, rt=0.82 min, m/z 390 (M+H)$^+$, m/z 434 (M+FA-H)$^−$.

HRMS (ESI, m/z): calcd for C$_{24}$H$_{24}$FN$_3$O (M+H)$^+$: 390.1982, found: 390.1972.

((3aR,4R,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (4/BRD1490)

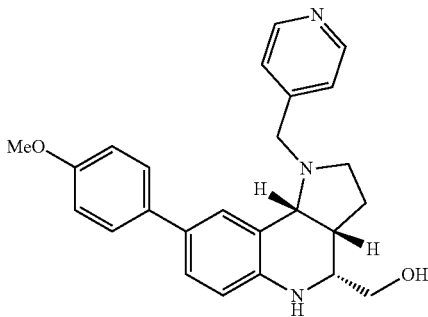 [SMILES: COc1ccc(-c2ccc3c(c2)[C@H]2[C@H](CCN2Cc2ccncc2)[C@H](CO)N3)cc1]

Prepared from benzyl (3aR,4R,9bR)-4-(hydroxymethyl)-8-(4-methoxy-phenyl)-2,3,3a,4,5,9b-hexahydro-1H-pyrrolo[3,2-c]quinoline-1-carboxylate 13d (142 mg, 0.32 mmol) according to General Procedure B. Purification by flash column chromatography eluting with 70% ethyl acetate in hexane gave the desired product 4 as an off-white solid (52 mg, yield 41%).

$R_f$=0.40 (silica gel, 5% methanol in dichloromethane, UV).

$^1$H NMR (400 MHz, CDCl$_3$): δ 8.54 (d, 2H, J=4.9 Hz, aromatic H), 7.44 (d, 2H, J=8.4 Hz, aromatic H), 7.32-7.25 (m, 4H, aromatic H), 6.96 (d, 2H, J=8.4 Hz, aromatic H), 6.73 (d, 1H, J=8.0 Hz, aromatic H), 4.43 (d, 1H, J=13.2 Hz, CH$_2$OH), 3.90-3.89 (m, 1H, CH$_2$NCH), 3.85 (s, 3H, OCH$_3$), 3.71-3.65 (m, 2H, CH$_2$NCH and NHCHCH), 3.49-3.45 (m, 2H, CH$_2$NCH and CH$_2$OH), 2.94-2.80 (m, 2H, NCH$_2$CH$_2$ and NHCHCH), 2.36-2.34 (m, 1H, NCH$_2$CH), 2.00-1.97 (m, 2H, NCH$_2$CH$_2$).

$^{13}$C NMR (100 MHz, CDCl$_3$): δ 158.4 (aromatic C), 150.3 (aromatic C), 149.9 (2) (aromatic C), 144.9 (aromatic C), 134.0 (aromatic C), 130.1 (aromatic C), 129.1 (aromatic C), 127.3 (2) (aromatic C), 127.2 (aromatic C), 123.8 (2) (aromatic C), 119.4 (aromatic C), 115.2 (aromatic C), 114.2 (2) (aromatic C), 64.4 (CH$_2$NCH), 63.3 (CH$_2$NCH), 58.1 (CH$_2$OH), 55.4 (OCH$_3$), 54.5 (NHCHCH), 51.6 (NCH$_2$CH$_2$), 38.2 (NHCHCH), 23.6 (NCH$_2$CH$_2$).

$[α]_D^{22}$=−34.1° (c=0.4, CHCl$_3$).

IR (thin film, cm$^1$): $ν_{max}$ 3364, 2911, 1609, 1495, 1246, 1180, 1045, 1027, 819, 754.

Chiral SFC (AS-H, 1.5 mL/min, MeOH with 0.05% Et$_3$N in CO$_2$, λ=210 nm): $t_R$(minor)=6.8 min, $t_R$(major)=7.1 min.

LCMS (UV Chromatogram, 210 nm, 2.5 min run): Purity >95% by UV, rt=0.79 min, m/z 402.5 (M+H)$^+$, m/z 446.6 (M+FA-H).

HRMS (ESI, m/z): calcd for C$_{25}$H$_{27}$N$_3$O$_2$ (M+H)$^+$: 402.2182, found: 402.2171.

((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (5/BRD0750)

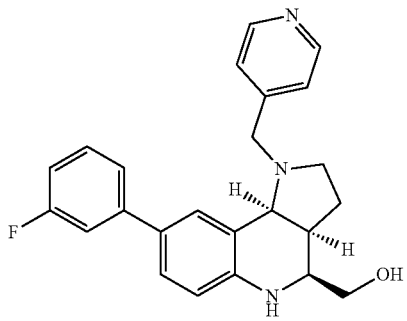 [SMILES: OC[C@H]1Nc2ccc(-c3cccc(F)c3)cc2[C@@H]2[C@H]1CCN2Cc1ccncc1]

Prepared from benzyl (3aS,4S,9bS)-8-(3-fluorophenyl)-4-(hydroxymethyl)-2,3,3a,4,5,9b-hexahydro-1H-pyrrolo[3,2-c]quinoline-1-carboxylate 13e (168 mg, 0.39 mmol) according to General Procedure B. Purification by flash column chromatography eluting with 80% ethyl acetate in hexane gave the desired product 5 as an off-white solid (71 mg, yield 47%).

$R_f$=0.25 (silica gel, 5% methanol in dichloromethane, UV)

$^1$H NMR (400 MHz, CDCl$_3$): δ 8.53 (d, 2H, J=5.0 Hz, aromatic H), 7.34-7.33 (m, 3H, aromatic H), 7.28-7.26 (m, 3H, aromatic H), 7.21 (d, 1H, J=10.6 Hz, aromatic H), 6.96 (t, 1H, J=8.4 Hz, aromatic H), 6.73 (d, 1H, J=8.4 Hz, aromatic H), 4.39 (d, 1H, J=13.2 Hz, CH$_2$OH), 3.87 (dd, 1H, J=11.6 Hz and 5.0 Hz, CH$_2$NCH), 3.71-3.67 (m, 2H, NHCHCH and CH$_2$NCH), 3.51 (d, 1H, J=13.2 Hz, CH$_2$OH), 3.47-3.45 (m, 1H, CH$_2$NCH), 2.96-2.90 (m, 1H, NCH$_2$CH$_2$), 2.82-2.79 (m, 1H, NCH$_2$CH$_2$), 2.39 (dd, 1H, J=17.8 Hz and 8.8 Hz, NCH$_2$CH$_2$), 1.99-1.96 (m, 2H, NHCHCH and NCH$_2$CH$_2$).

$^{13}$C NMR (100 MHz, CDCl$_3$): δ 164.5 and 162.1 (d, $^1J_{C,F}$=243 Hz, aromatic C), 149.7 (2) (pyridinyl C), 148.0 (aromatic C), 145.9 (pyridinyl C), 143.5 and 143.4 (d, $^3J_{C,F}$=7.5 Hz, aromatic C), 130.1 and 130.0 (d, $^3J_{C,F}$=8.6 Hz, aromatic C), 129.4 (aromatic C), 128.8 (aromatic C), 127.5 (aromatic C), 123.9 (2) (pyridinyl C), 121.8 and 121.7 (d, $^4J_{C,F}$=2.8 Hz, aromatic C), 119.5 (aromatic C), 115.2 (aromatic C), 113.0 and 112.8 (d, $^2J_{C,F}$=21.4 Hz, aromatic C), 112.9 and 112.7 (d, $2J_{C,F}$=20.9 Hz, aromatic C), 64.2 (CH$_2$NCH), 63.3 (CH$_2$NCH), 58.1 (CH$_2$OH), 54.4 (NHCHCH), 51.6 (NCH$_2$CH$_2$), 38.1 (NHCHCH), 23.6 (NCH$_2$CH$_2$).

$^{19}$F NMR (376 MHz, CDCl$_3$): δ –113.4.

$[α]_D^{22}$=+23.6° (c=0.4, CHCl$_3$).

Chiral SFC (AS-H, 1.5 mL/min, MeOH with 0.05% Et$_3$N in CO$_2$, λ=210 nm): $t_R$(major)=6.2 min, $t_R$(minor)=6.9 min.

IR (thin film, cm$^1$): $v_{max}$ 3332, 2916, 1608, 1517, 1480, 1300, 1262, 1193, 1167, 1077, 867, 821, 784, 753, 692.

LCMS (UV Chromatogram, 210 nm, 2.5 min run): Purity >95% by UV, rt=0.86 min, m/z 390.5 (M+H)$^+$, m/z 434.5 (M+FA-H)$^-$.

HRMS (ESI, m/z): calcd for C$_{24}$H$_{24}$FN$_3$O (M+H)$^+$: 390.1982, found: 390.1973.

((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (6/BRD6201)

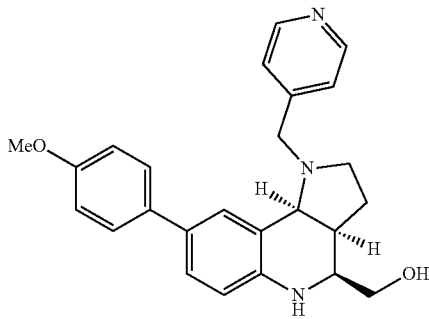 [SMILES: COc1ccc(-c2ccc3c(c2)[C@@H]2[C@@H](CCN2Cc2ccncc2)[C@@H](CO)N3)cc1]

Prepared from benzyl (3aS,4S,9bS)-4-(hydroxymethyl)-8-(4-methoxy-phenyl)-2,3,3a,4,5,9b-hexahydro-1H-pyrrolo[3,2-c]quinoline-1-carboxylate 13f (178 mg, 0.45 mmol) according to General Procedure B. Purification by flash column chromatography eluting with 65% ethyl acetate in hexane gave the desired product 6 as an off-white solid (65 mg, yield 41%).

$R_f$=0.43 (silica gel, 5% methanol in dicholoromethane, UV).

$^1$H NMR (400 MHz, CDCl$_3$): δ 8.54 (d, 2H, J=5.0 Hz, aromatic H), 7.44 (d, 2H, J=8.2 Hz, aromatic H), 7.33-7.25 (m, 4H, aromatic H), 6.96 (d, 2H, J=8.2 Hz, aromatic H), 6.73 (d, 1H, J=8.2 Hz, aromatic H), 4.44 (d, 1H, J=13.2 Hz, CH$_2$OH), 3.92-3.86 (m, 1H, CH$_2$NCH), 3.85 (s, 3H, OCH$_3$), 3.71 (dd, 1H, J=11.3 Hz and 3.6 Hz, CH$_2$NCH), 3.65-3.64 (m, 1H, NHCHCH), 3.48-3.44 (m, 2H, CH$_2$NCH and CH$_2$OH), 2.95-2.91 (m, 1H, NCH$_2$CH$_2$), 2.84-2.81 (m, 1H, NCH$_2$CH$_2$), 2.36-2.34 (m, 1H, NCH$_2$CH$_2$), 2.03-1.95 (m, 2H, NCH$_2$CH$_2$).

$^{13}$C NMR (100 MHz, CDCl$_3$): δ 158.4 (aromatic C), 149.8 (2) (aromatic C), 148.0 (aromatic C), 144.9 (aromatic C), 134.0 (aromatic C), 130.1 (aromatic C), 129.1 (aromatic C), 127.3 (2) (aromatic C), 127.3 (aromatic C), 123.8 (2) (aromatic C), 119.3 (aromatic C), 115.2 (aromatic C), 114.2 (2) (aromatic C), 64.4 (CH$_2$NCH), 63.3 (CH$_2$NCH), 58.1 (CH$_2$OH), 55.4 (OCH$_3$), 54.4 (NHCHCH), 51.6 (NCH$_2$CH$_2$), 38.1 (NHCHCH), 23.7 (NCH$_2$CH$_2$).

$[α]_D^{22}$=–24.6° (c=0.4, CHCl$_3$).

Chiral SFC (AS-H, 1.5 mL/min, MeOH with 0.05% Et$_3$N in CO$_2$, λ=210 nm): $t_R$(major)=6.9 min, $t_R$(minor)=7.2 min.

IR (thin film, cm$^1$): $v_{max}$ 3365, 2925, 1610, 1496, 1246, 1180, 1045, 1027, 818, 756.

LCMS (UV Chromatogram, 210 nm, 2.5 min run): Purity >95% by UV, rt=0.80 min, m/z 402.1 (M+H)$^+$, m/z 446.6 (M+FA-H)$^-$.

HRMS (ESI, m/z): calcd for C$_{25}$H$_{27}$N$_3$O$_2$ (M+H)$^+$: 402.2182, found: 402.2180.

((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (7/BRD5039)

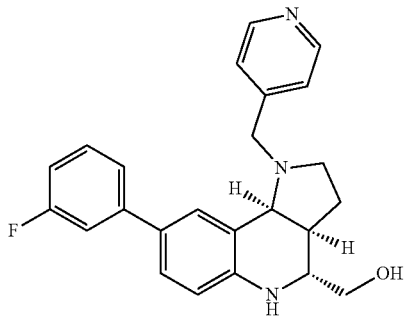 [SMILES: OC[C@@H]1Nc2ccc(-c3cccc(F)c3)cc2[C@@H]2[C@H]1CCN2Cc1ccncc1]

Prepared from benzyl (3aS,4R,9bS)-8-(3-fluorophenyl)-4-(hydroxymethyl)-2,3,3a,4,5,9b-hexahydro-1H-pyrrolo[3,2-c]quinoline-1-carboxylate 13g (168 mg, 0.39 mmol) according to General Procedure B. Purification by flash column chromatography eluting with 80% ethyl acetate in hexane gave the desired product 7 as an off-white solid (83 mg, yield 55%).

$R_f$=0.39 (silica gel, 10% methanol in dichloromethane, UV)

$^1$H NMR (400 MHz, CDCl$_3$): δ 8.46 (d, 2H, J=5.0 Hz, aromatic H), 7.35-7.33 (m, 2H, aromatic H), 7.28-7.25 (m, 4H, aromatic H), 7.21-7.19 (m, 1H, aromatic H), 6.97 (t, 1H, J=8.6 Hz, aromatic H), 6.73 (d, 1H, J=8.4 Hz, aromatic H), 4.37 (d, 1H, J=13.6 Hz, CH$_2$OH), 4.01 (d, 1H, J=9.4 Hz, CH$_2$NCH), 3.57-3.53 (m, 2H, NHCHCH and CH$_2$NCH), 3.37 (s, 1H, CH$_2$NCH), 3.30 (d, 1H, J=13.8 Hz, CH$_2$OH), 2.97-2.93 (m, 1H, NCH$_2$CH$_2$), 2.24-2.21 (m, 1H, NCH$_2$CH$_2$), 2.10-2.04 (m, 2H, NCH$_2$CH$_2$ and NHCHCH), 1.67-1.64 (m, 1H, NCH$_2$CH$_2$).

$^{13}$C NMR (100 MHz, CDCl$_3$): δ 164.5 and 162.1 (d, $^1J_{C,F}$=243.4 Hz, aromatic C), 149.8 (aromatic C), 149.0 (2) (pyridinyl C), 144.6 (pyridinyl C), 143.6 and 143.5 (d, $^3J_{C,F}$=8.4 Hz, aromatic C), 130.3 (aromatic C), 130.1 and 130.0 (d, $^3J_{C,F}$=8.9 Hz, aromatic C), 127.9 (aromatic C), 127.6 (aromatic C), 123.6 (2) (pyridinyl C), 121.7 and 121.7 (d, $^4J_{C,F}$=1.7 Hz, aromatic C), 118.2 (aromatic C), 114.7 (aromatic C), 113.0 and 112.8 (d, $^2J_{C,F}$=21.5 Hz, aromatic C), 112.8 and 112.6 (d, $^2J_{C,F}$=21.0 Hz, aromatic C), 64.7 (CH$_2$NCH), 64.2 (CH$_2$NCH), 56.0 (CH$_2$OH), 54.5 (NHCHCH), 51.4 (NCH$_2$CH$_2$), 35.8 (NHCHCH), 25.7 (NCH$_2$CH$_2$).

$^{19}$F NMR (376 MHz, CDCl$_3$): δ –113.4.

$[α]_D^{22}$=–30.4° (c=0.4, CHCl$_3$).

Chiral SFC (AS-H, 1.5 mL/min, MeOH with 0.05% Et$_3$N in CO$_2$, λ=210 nm): $t_R$(major)=6.4 min, $t_R$(minor)=7.0 min.

IR (thin film, cm$^{-1}$): $v_{max}$ 3334, 2927, 1608, 1522, 1484, 1326, 1261, 1198, 1160, 1076, 868, 819, 782, 752. 694.

LCMS (UV Chromatogram, 210 nm, 2.5 min run): Purity >95% by UV, rt=0.87 min, m/z 390.2 (M+H)$^+$, m/z 434.6 (M+FA-H)$^-$.

HRMS (ESI, m/z): calcd for $C_{24}H_{24}FN_3O$ (M+H)$^+$: 390.1982, found: 390.1976.

((3aS,4R,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (8/BRD0739)

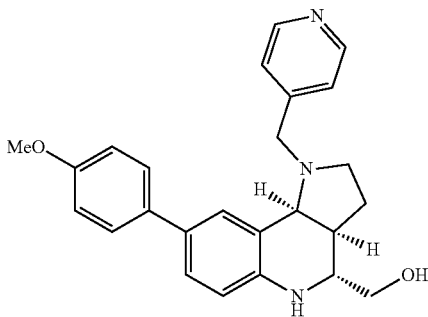 [SMILES: COc1ccc(-c2ccc3c(c2)[C@@H]2[C@@H](CCN2Cc2ccncc2)[C@H](CO)N3)cc1]

Prepared from benzyl (3aS,4R,9bS)-4-(hydroxymethyl)-8-(4-methoxy-phenyl)-2,3,3a,4,5,9b-hexahydro-1H-pyrrolo[3,2-c]quinoline-1-carboxylate 13h (143 mg, 0.32 mmol) according to General Procedure B. Purification by flash column chromatography eluting with 70% ethyl acetate in hexane gave the desired product 8 as an off-white solid (62 mg, yield 48%).

$R_f$=0.67 (silica gel, 10% methanol in dichloromethane, UV)

$^1$H NMR (400 MHz, CDCl$_3$): δ 8.46 (d, 2H, J=4.8 Hz, aromatic H), 7.44-7.43 (d, 2H, J=8.2 Hz, aromatic H), 7.32-7.27 (m, 4H, aromatic H), 6.96 (d, 2H, J=8.2 Hz, aromatic H), 6.73 (d, 1H, J=8.2 Hz, aromatic H), 4.39 (d, 1H, J=13.8 Hz, CH$_2$OH), 3.99 (d, 1H, J=10.0 Hz, CH$_2$NCH), 3.85 (s, 3H, OCH$_3$), 3.58-3.52 (m, 2H, CH$_2$NCH and NHCHCH), 3.37 (s, 1H, CH$_2$NCH), 3.29 (d, 1H, J=13.8 Hz, CH$_2$OH), 2.96 (t, 1H, J=9.0 Hz, NCH$_2$CH$_2$), 2.24-2.18 (m, 1H, NCH$_2$CH$_2$), 2.10-2.07 (m, 2H, NCH$_2$CH$_2$ and NHCHCH), 1.68-1.64 (m, 1H, NCH$_2$CH$_2$).

$^{13}$C NMR (100 MHz, CDCl$_3$): δ 158.3 (aromatic C), 149.8 (aromatic C), 149.1 (2) (aromatic C), 143.7 (aromatic C), 134.0 (aromatic C), 129.9 (aromatic C), 129.3 (aromatic C), 127.4 (aromatic C), 127.3 (2) (aromatic C), 123.7 (2) (aromatic C), 118.2 (aromatic C), 114.8 (aromatic C), 114.2 (2) (aromatic C), 64.6 (CH$_2$NCH), 64.2 (CH$_2$NCH), 56.1 (CH$_2$OH), 55.4 (OCH$_3$), 54.6 (NHCHCH), 51.4 (NCH$_2$CH), 35.9 (NHCHCH), 25.7 (NCH$_2$CH$_2$).

$[\alpha]_D^{22}$=−23.4° (c=0.4, CHCl$_3$).

Chiral SFC (AS-H, 1.5 mL/min, MeOH with 0.05% Et$_3$N in CO$_2$, λ=210 nm): $t_R$(major)=6.1 min, $t_R$(minor)=7.3 min.

IR (thin film, cm$^1$): $\nu_{max}$ 3402, 2929, 1614, 1499, 1246, 1180, 1029, 817, 753.

LCMS (UV Chromatogram, 210 nm, 2.5 min run): Purity >95% by UV, rt=0.80 min, m/z 402.2 (M+H)$^+$, m/z 446.6 (M+FA-H)$^-$.

HRMS (ESI, m/z): calcd for $C_{25}H_{27}N_3O_2$ (M+H)$^+$: 402.2182, found: 402.2172.

tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14)

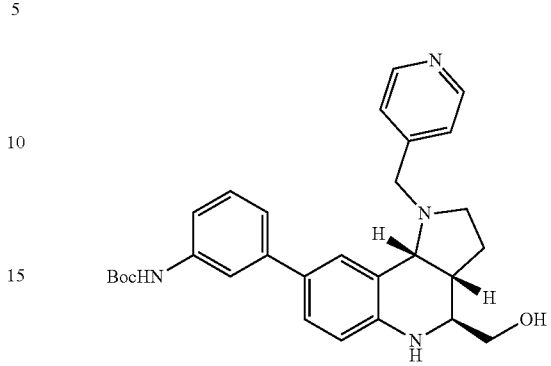

Prepared from benzyl (3aR,4S,9bR)-8-(3-((tert-butoxycarbonyl)amino)-phenyl)-4-(hydroxymethyl)-2,3,3a,4,5,9b-hexahydro-1H-pyrrolo[3,2-c]quinoline-1-carboxylate 13i (210 mg, 0.53 mmol) according to General Procedure B. Purification by flash column chromatography eluting with 60% to 90% ethyl acetate in hexane gave the desired product 14 as a white solid (205 mg, yield 79%).

$R_f$=0.28 (silica gel, 10% methanol in dichloromethane, UV).

$^1$H NMR (400 MHz, CDCl$_3$): δ 8.45 (d, 2H, J=5.0 Hz, aromatic H), 7.50 (s, 1H, aromatic H), 7.35-7.29 (m, 5H, aromatic H), 7.18 (d, 1H, J=7.3 Hz, aromatic H), 6.71 (d, 1H, J=8.2 Hz, aromatic H), 4.34 (d, 1H, J=13.8 Hz, CH$_2$OH), 3.98 (d, 1H, J=10.2 Hz, CH$_2$NCH), 3.58 (d, 1H, J=10.2 Hz, CH$_2$NCH), 3.53-3.51 (m, 1H, NHCHCH), 3.36-3.32 (m, 2H, CH$_2$NCH and CH$_2$OH), 2.99-2.97 (m, 1H, NCH$_2$CH$_2$), 2.27-2.25 (m, 1H, NCH$_2$CH$_2$), 2.10-2.03 (m, 2H, NCH$_2$CH$_2$ and NHCHCH), 1.69-1.67 (m, 1H, NCH$_2$CH$_2$), 1.54 (s, 9H, tert-butyl CH$_3$).

$^{13}$C NMR (100 MHz, CDCl$_3$): δ 171.2 (CONH), 152.9 (aromatic C), 148.8 (aromatic C), 144.3 (aromatic C), 142.0 (aromatic C), 138.8 (aromatic C), 130.3 (aromatic C), 129.3 (aromatic C), 127.9 (aromatic C), 123.8 (aromatic C), 121.0 (aromatic C), 116.5 (aromatic C), 116.4 (aromatic C), 114.8 (aromatic C), 80.5 (tert-butyl C), 64.6 (CH$_2$NCH), 64.3 (CH$_2$NCH), 56.0 (CH$_2$OH), 54.4 (NHCHCH), 51.4 (NCH$_2$CH$_2$), 35.8 (NHCHCH), 28.4 (tert-butyl CH$_3$), 25.8 (NCH$_2$CH$_2$).

$[\alpha]_D^{22}$=+57.6° (c=0.5, CHCl$_3$).

Chiral SFC (AS-H, 1.5 mL/min, MeOH with 0.05% Et$_3$N in CO$_2$, λ=210 nm): $t_R$(minor)=6.5 min, $t_R$(major)=6.9 min.

IR (thin film, cm$^{-1}$): $\nu_{max}$ 3425, 2930, 1706, 1606, 1514, 1366, 1241, 1162, 1065, 788, 754, 699.

LCMS (UV Chromatogram, 210 nm, 2.5 min run): Purity >85% by UV, rt=0.99 min, m/z 487.6 (M+H)$^+$, m/z 531.7 (M+FA-H)$^-$.

HRMS (ESI, m/z): calcd for $C_{29}H_{35}N_4O_3$ (M+H)$^+$: 487.2709, found: 487.2720.

Example 2. Assays for Detection of RNA Guided Endonuclease Activities

Fluorescence Polarization-Based Assay

Binding to PAM-site (NGG for SpCas9) is an important first step in target recognition by SpCas9. Since disruption of PAM-site binding (e.g., by mutating SpCas9 residues involved in PAM-site recognition or mutating PAM-sequence) disrupts SpCas9 activity, it was hypothesized that inhibitors disrupting SpCas9's PAM-binding also render SpCas9 inactive. The affinity of SpCas9 for a single PAM site is weak, which portends well for identifying potential inhibitors, but the low affinity creates a challenge in developing a robust assay for SpCas9-PAM binding activity.

SpCas9 affinity for DNA sequences increases monotonically with the increase in the number of PAM sites. Fluorescence polarization (FP) is a useful technique to monitor protein:DNA interaction, including for example, Cas9-gRNA (ribonucleoprotein) complex and target DNA (12PAM). It was discovered that the fluorescence polarization signal of the fluorophore appended to the DNA increased when target DNA bound to the [Cas9:guideRNA] complex (FIG. 1A). The following fluorophore-labelled PAM-rich target DNA was used:

(SEQ ID NO: 1)
5'-GGCTGGACCACGCGGGAAAATCCACCTAGGTGGTTCCTCTTCGG

ATGTTCCATCCTTT/36-FAM-3'

(SEQ ID NO: 2)
3'-CCGACCTGGTGCGCCCTTTTAGGTGGATCCACCAAGGAGAAGCC

TACAAGGTAGGAAA-5'

Figure 1B:
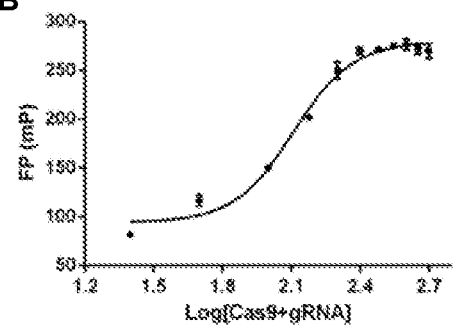
FIG. 1B is a graph showing a dose-dependent increase in FP signal with increasing equivalents of [Cas9:guideRNA] complex relative to those of 12 PAM-DNA.

As the target DNA is much smaller than the [Cas9:guideRNA] complex, the target DNA's tumbling rate is significantly reduced upon binding to [Cas9:guideRNA] complex. Exploiting the above results, an assay was developed that monitors the change in the fluorescence polarization of the fluorophore-labelled PAM-rich target DNA (henceforth called 12PAM-DNA) upon binding to [Cas9:guideRNA] complex. In this assay, the complexation of [Cas9:guideRNA] to 12PAM-DNA showed a dose-dependent increase in fluorophore polarization (FIG. 1B).

Figure 1C:
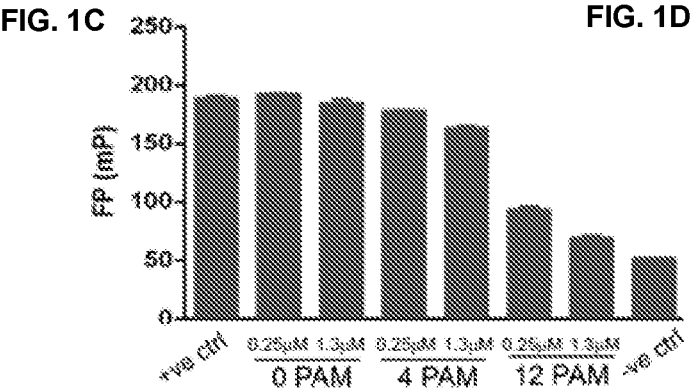
FIG. 1C is a graph showing results of competition experiments using DNA sequences with varying numbers of PAM-sites. A decrease in FP signal was observed as the number of PAM-sites increased on the competitor.
Figure 1D:
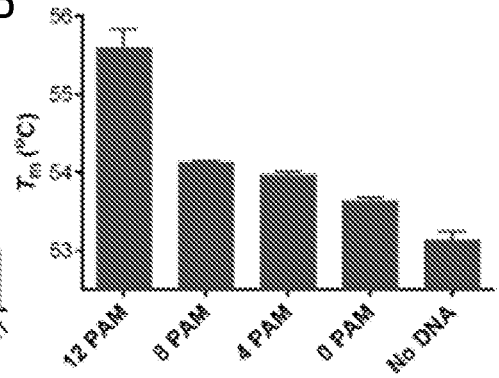
FIG. 1D is a graph showing that thermal stability of [Cas9:guideRNA] complex increased as PAM-sites increased on the interacting DNA.

The FP-assay was validated using competition and differential scanning fluorimetry experiments. In the competition experiment, 12PAM-DNA was competed with DNA sequences containing a varying number of PAM-sites. A drop in FP-signal of 12PAM-DNA was observed that was proportional to the number of PAM-sites on the competitor DNA (FIG. 1C). Next, differential scanning fluorimetry was used, which can detect the perturbation in thermal stability of a protein upon ligand binding. The melting temperature of the [SpCas9:guideRNA] complex was determined in the presence of DNA sequences with varying number of PAM-sites (FIG. 1D). The melting temperature increase was proportional to the number of PAM-sites on the target DNA. It was found that Z-prime of the FP-assay (in a 384-well format) is between 0.6-0.8, which further confirms the robustness of the assay.

Motivated by these findings, a pilot screening of ~15,000 compounds was performed in two replicates (FIG. 2A). These compounds belonged to Broad Institute's "informer set" and the "performance diverse set" (Wawer et al., *Proc Natl Acad Sci USA* 2014, 111, 10911-6) which primarily includes compounds from commercial sources. Broad Institute has ~100,000 diversity-oriented synthesis compounds in various libraries. However, screening all of these compounds has the potential to be inefficient, as compounds within a single library are relatively similar to each other, and may perform similarly in assays. The Computational Chemical Biology group at the Broad Institute has established a list of ~10,000 compounds, called the "Informer set," that maximally represent the diversity across all diversity-oriented synthesis compounds. Finally, 12PAM-DNA without fluorophore was used as a positive control. Compounds were classified as "hits" (circled in red; FIG. 2A) if they lowered the FP-signal by values greater than 3 standard deviations ($3\sigma$) of DMSO.

All the "hits" came from Broad Institute's in-house libraries and none from the commercial libraries. Interestingly, compounds from specific libraries were observed to be highly enriched in hits pointing to the strong structure-activity relationship. Most excitingly, dose curves of "hits" from spirocyclic-azetidine library demonstrated stereochemical-dependence on the activity (FIG. 2B); compounds, BRD4172 and BRD1656, are diastereomers that have >15-fold difference in $IC_{50}$. Without intending to be bound by theory, the stereochemical-activity relationship points to specific nature of the interaction between these compounds and SpCas9. The differential potency of these compounds was able to be confirmed in a DNA cleavage assay.

In a typical experimental protocol, a plasmid DNA substrate containing target gene corresponding to the guide RNA (gRNA) was incubated with Cas9/gRNA complex at 37° C. for 10 min before quenching by addition of EDTA. For compound testing, Cas9/gRNA RNP complex was incubated with compounds at the indicated concentration for 30 min before introducing cleavable plasmid DNA into it. Reaction mixtures were then analyzed by running on an agarose gel with ethidium bromide as the DNA staining agent.

Briefly, SpCas9 activity was followed by quantifying the amount of cleaved product of a target gene using agarose DNA gel (FIGS. 2E and 2F). Dose-dependence was observed in a reduction in the amount of cleaved product only for the two most potent compounds from the screen (FIGS. 2E and 2F).

Spinach Transcription Assay

Figure 3A:
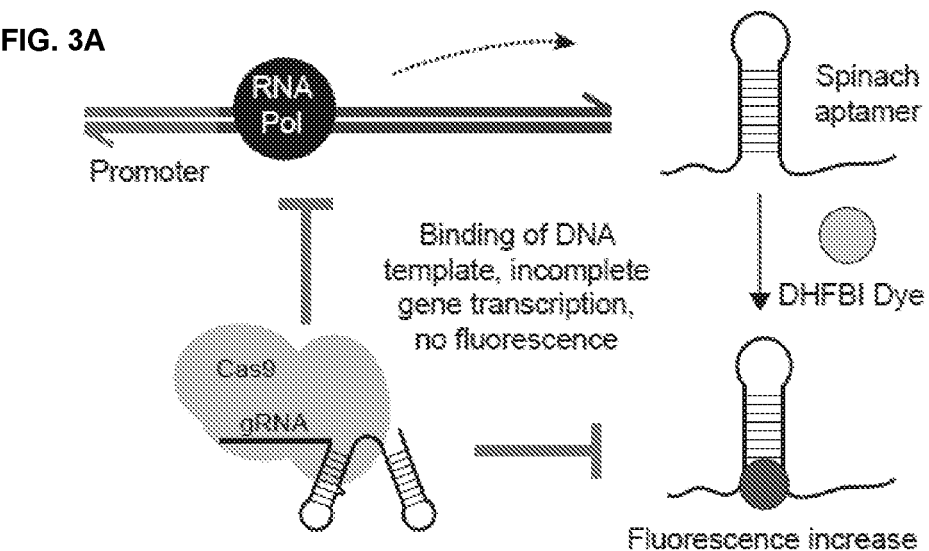
FIG. 3A is a schematic of a spinach-based in vitro transcription assay for monitoring Cas9 nuclease activity. In absence of Cas9, T7 RNA polymerase is recruited to a T7 promoter-containing DNA template to transcribe the spinach RNA aptamer, which can bind to the fluorogenic molecule DFHBI. Cleavage of the DNA by Cas9 results in complete termination of transcription or production of unproductive RNA, resulting in loss of fluorescence. Cas9 can recognize PAM sites native to the T7 and spinach sequences, or variable PAMs proximal and distal to the T7 promoter.

A mechanism-independent assay was developed to assess any Cas9 nuclease activity in vitro. Thus, an in vitro transcription based assay was developed wherein the transcribed mRNA is the "spinach aptamer" that fluoresces in the presence of a small molecule (Paige et al., *Science* 2011, 333, 642-6) (FIG. 3A; Table 1). Coupling of an in vitro transcription (IVT) reaction produces the RNA aptamer Spinach which, upon binding to the small molecule DFHBI, produces a fluorescent complex. A synthetic gene-like construct was designed to use the bacteriophage T7 RNA Polymerase (T7 RNAP) to drive the production of the Spinach RNA aptamer. This dsDNA construct, termed a 'genelet,' consists of a T7 RNAP promoter upstream of the region that codes for the spinach RNA. Cas9 gRNAs designed to bind to and/or cleave PAM-containing sites within the Spinach DNA template (FIG. 3B), would be able to interfere with T7 RNAP transcription and inhibit production of a functional DFHBI-binding RNA, and hence decrease fluorescence (FIG. 3A).

TABLE 1

| Spinach Transcription Assay sequences | |
|---|---|
| Spinach aptamer | GGGAGACGCAACUGAAUGAAAUGGUGAAGGACG GGUCCAGGUGUGGCUGCUUCGGCAGUGCAGCUU GUUGAGUAGAGUGUGAGCUCCGCGUAACUAGUC GCGUCAC (SEQ ID NO: 20) |
| Guide RNA | GCUAUAGGACGCGACCGAAAGUUUUAGAGCUAG AAAUAGCAAGUUAAAAUAAGGCUAGUCCGUUAU CAACUUGAAAAAGUGGCACCGAGUCGGUGCUUU U (SEQ ID NO: 11) |

TABLE 1-continued

Spinach Transcription Assay sequences

| | |
|---|---|
| Spinach DNA NonTemplate Strand | TAATACGACTCACTATAGGACGCGACCGAAATG GTGAAGGACGGGT (SEQ ID NO: 3) |
| Spinach DNA Template Strand | ACCCGTCCTTCACC<u>ATTTCGGTCGCGTCCTATA GT</u>GAGTCGTATTA (SEQ ID NO: 21) |
| Spinach DNA Template | GCGCGCTTTCTAATACGACTCACTATAGGGTGA CGCGACCGAAATGGTGAAGGACGGGTCCAGTGC TTCGGCACTGTTGAGTAGAGTGTGAGCTCCGTA ACTGGTCGCGTC (SEQ ID NO: 14) |
| Spinach RNA aptamer | <u>GGU</u>GACGCGACCGAAAUGGUGAAGGACGGGUCC AGUGCUUCGGCACUGUUGAGUAGAGUGUGAGCU CCGUAACUGGUCGCGUC (SEQ ID NO: 12) |
| Spinach DNA Template (general) | GCGCGCNNNNTAATACGACTCACTATAGGGNNN NGACGCGACCGAAATGGTGAAGGACGGGTCCAG TGCTTCGGCACTGTTGAGTAGAGTGTGAGCTCC GTAACTGGTCGCGTC (SEQ ID NO: 15) |
| Spinach RNA aptamer (general) | GGNNNNGACGCGACCGAAAUGGUGAAGGACGGG UCCAGUGCUUCGGCACUGUUGAGUAGAGUGUGA GCUCCGUAACUGGUCGCGUC (SEQ ID NO: 13) |

T7 Promoter = TAATACGACTCACTA (SEQ ID NO: 22)
Cpf1 PAM = TTTN
SpCas9 PAM = NGG
SaCas9 PAM = NNGGGT
NNNN represents any nucleotide A, G, T, or C. The length of the string of NNNN is arbitrary, and can be expanded to accommodate the PAM consensus motif of any RNA-programmable DNA nuclease. The first "NNNN" site accommodates distal-PAM binding nucleases such as those of the Cpf1 family, while the second "NNNN" site accommodates both distal and proximal PAM binding nucleases (such as those of the Cpf1 family and Cas9 family, respectively).

Figure 3B:
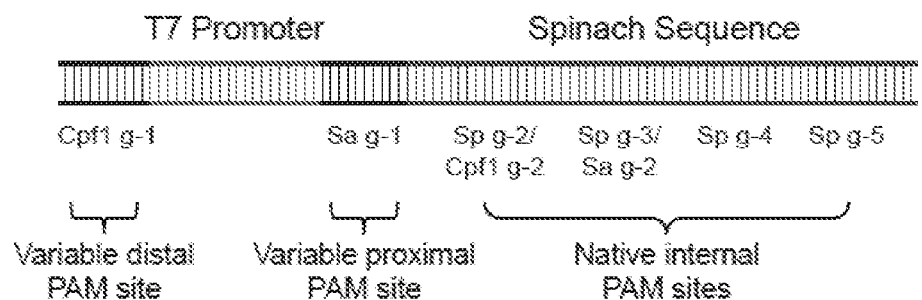
FIG. 3B is a schematic of the DNA template, detailing gRNA sites, both engineered and native.
Figure 3C:
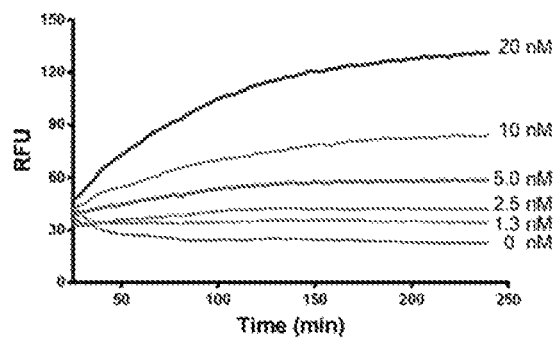
FIG. 3C is a graph depicting validation of the Spinach-assay.

Using a T7 polymerase for transcription, as low as 1 nM of the spinach gene was able to be detected (FIG. 3B). When [SpCas9: guideRNA] complex was added to the transcription mix, transcription was blocked as evident by the lack of increase in fluorescence over time (FIG. 3C). Note that addition of SpCas9 or guideRNA alone did not block transcription. Finally, it was found that one of the potent spirocyclic compounds from the primary screening successfully blocked the transcription inhibition of [SpCas9: guideRNA] complex.

Figure 3D:
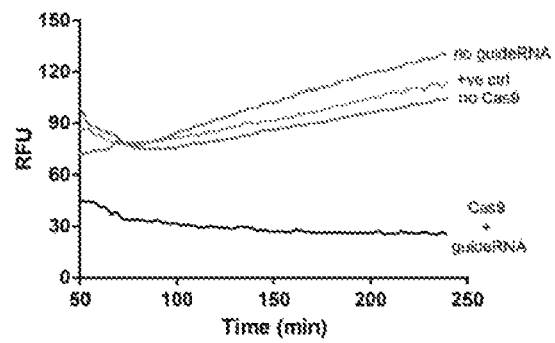
FIG. 3D is a graph depicting that SpCas9-mediated knockdown of spinach gene led to loss of fluorescence.

Without being bound by theory, as long as the correct PAM sequence is present in the DNA template, it is possible to use any Cas nuclease with the appropriate gRNA (Table 1). Analysis of the Spinach sequence revealed a number of NGG sites evenly distributed throughout the sequence, allowing for preliminary optimization of the assay with SpCas9. Indeed, titering the amount of DNA template used (0.1 nM) was able to detect nanomolar levels of SpCas9 activity using a guide RNA that targeted site Sp-g1 (FIG. 3C). This activity was dependent on the SpCas9 concentration and was highly dependent on the site of cleavage—scanning the length of the spinach sequence with 4 different SpCas9 guides (Sp-g1 through g4) revealed that binding events 5' to the DFHBI-binding $L_{12}$ loop resulted in fluorescence loss, while binding after this loop produced fluorescence (FIG. 3D).

Figure 3E:
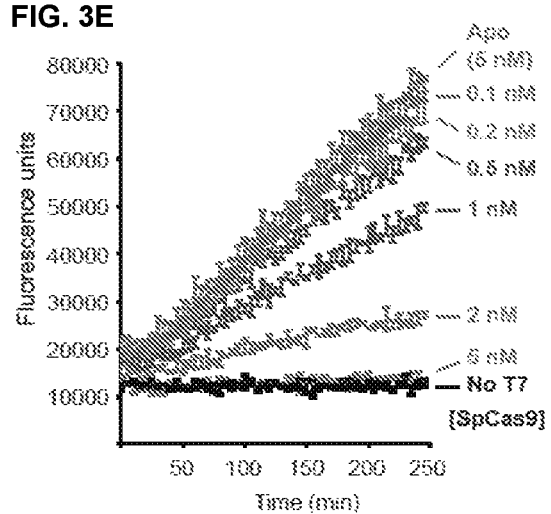
FIG. 3E is a graph showing that SpCas9:gRNA targeting site Sp g-2 caused loss of spinach fluorescence in a dose-dependent manner. ApoCas9 at 5 nM did not result in cleavage, indicating that this loss is due to cleavage of the spinach DNA template. Error bars represent the standard deviation from n=3 technical replicates.
Figure 3F:
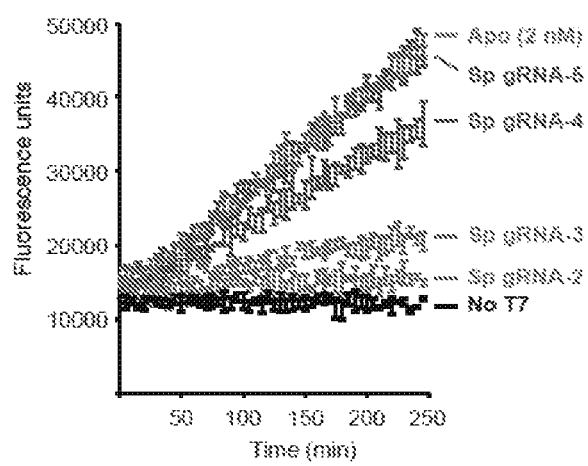
FIG. 3F is a graph showing that SpCas9:gRNA-mediated fluorescence loss was dependent on the position of the gRNA, with PAM sites closer to the T7 promoter (in order: Sp g-2, g-3, g-4, and g-5) being more efficient. ApoCas9 at 2 nM did not result in cleavage. Error bars represent the standard deviation from n=3 technical replicates.
Figure 3G:
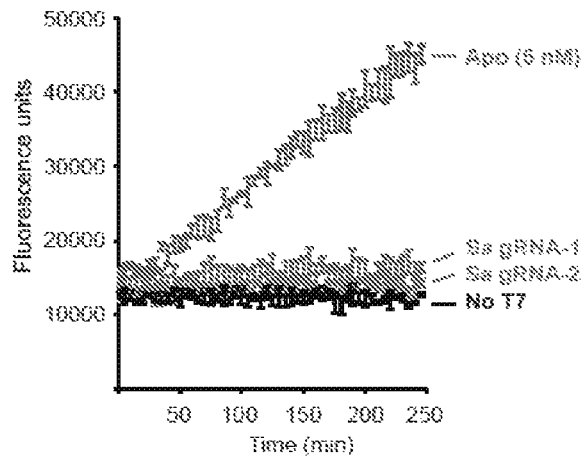
FIG. 3G is a graph showing Cas nuclease-mediated inhibition of IVT in SaCas9. Active SaCas9:gRNA (5 nM) can be used at both an endogenous PAM site (Sa g-1) and an installed GGGT proximal PAM site (Sa g-2). ApoSaCas9 (5 nM) did not result in cleavage. Error bars represent the standard deviation from n=3 technical replicates.
Figure 3H:
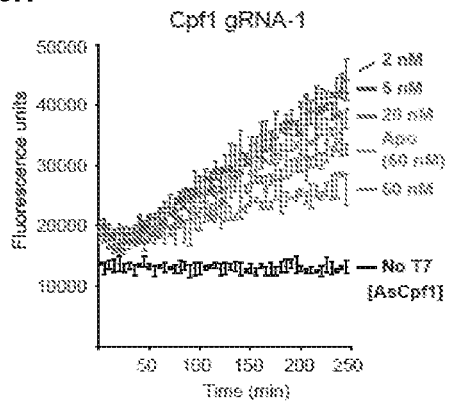
FIG. 3H is a set of graphs showing Cas nuclease-mediated inhibition of IVT in AsCpf1. Active AsCpf1:gRNA can cleave an installed distal TTTC PAM site (Cpf1 gRNA-1; upper) or native TTTC site (Cpf1 gRNA-2; lower) in a dose dependent manner, albeit with lower efficiency compared to other tested Cas nucleases. Error bars represent the standard deviation from n=3 technical replicates.
Figure 3I:
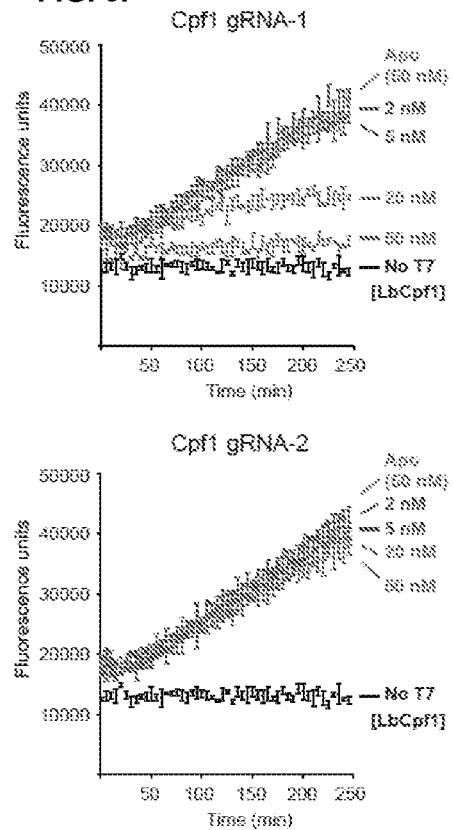
FIG. 3I is a set of graphs showing Cas nuclease-mediated inhibition of IVT in LbCpf1. Active LbCpf1:gRNA can cleave an installed distal TTTC PAM site (Cpf1 gRNA-1; upper) or native TTTC site (Cpf1 gRNA-2; lower) in a dose dependent manner, albeit with lower efficiency compared to other tested Cas nucleases. Error bars represent the standard deviation from n=3 technical replicates.
Figure 3J:
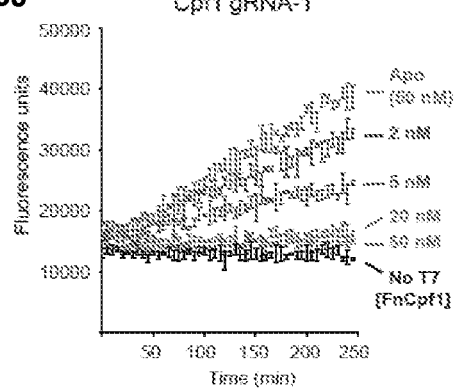
FIG. 3J is a set of graphs showing Cas nuclease-mediated inhibition of IVT in FnCpf1. Active FnCpf1:gRNA can cleave an installed distal TTTC PAM site (Cpf1 gRNA-1; upper) or native TTTC site (Cpf1 gRNA-2; lower) in a dose dependent manner, albeit with lower efficiency compared to other tested Cas nucleases. Error bars represent the standard deviation from n=3 technical replicates.

While this indicated that no modifications would be needed to assess this assay in the context of SpCas9, it hindered the generalizability of the assay to include Cas9 nucleases with more complex PAM recognitions. Indeed, the spinach gene only contained only one NNGGGT and TTTN site each, which are the PAM recognition sequences for SaCas9 and AsCpf1/LbCpf1, respectively. To overcome this limitation, additional nucleotides were inserted that could accommodate arbitrary PAM sites—one between the T7 promoter and the spinach gene (proximal site, intended for 3'-PAM binding Cas enzymes), and one upstream of the T7 promoter (distal site, intended for 5'-PAM binding Cas enzymes like Cpf1. The proximal site contained a TAGGGT SaCas9 PAM, and the distal site contained a TTTC Cpf1 PAM (FIG. 3B). Early termination of spinach transcription resulted in optimal fluorescence loss. Without being bound by theory, it was reasoned that these sites would allow direct targeting of the T7 promoter to completely abolish transcription. When comparing the activity of SaCas9 with a guide RNA targeting an internal spinach site (Sa-g1) and the proximal variable site (Sa-g2), comparable loss of DFHBI fluorescence was observed with nanomolar levels of SaCas9 (FIG. 3E).

Figure 4A:
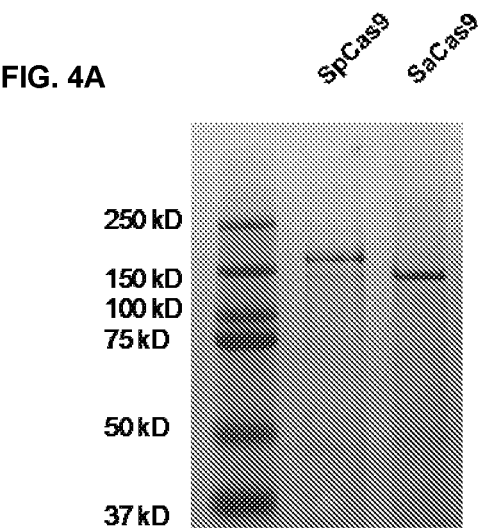
FIG. 4A is an image of an SDS-PAGE gel showing purified SaCas9 and SpCas9.
Figure 4B:
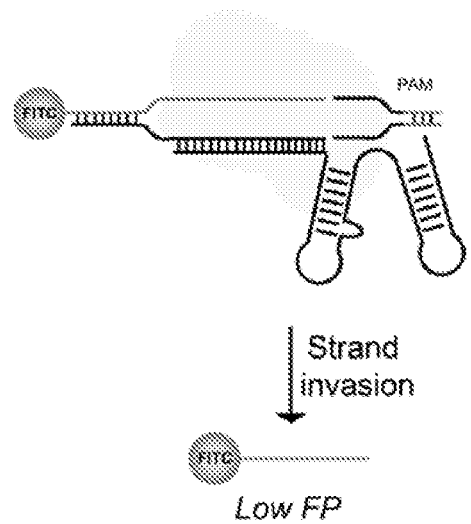
FIG. 4B is a schematic depicting a fluorescence polarization-based strand invasion assay to monitor nuclease activity of Cas9.
Figure 4C:
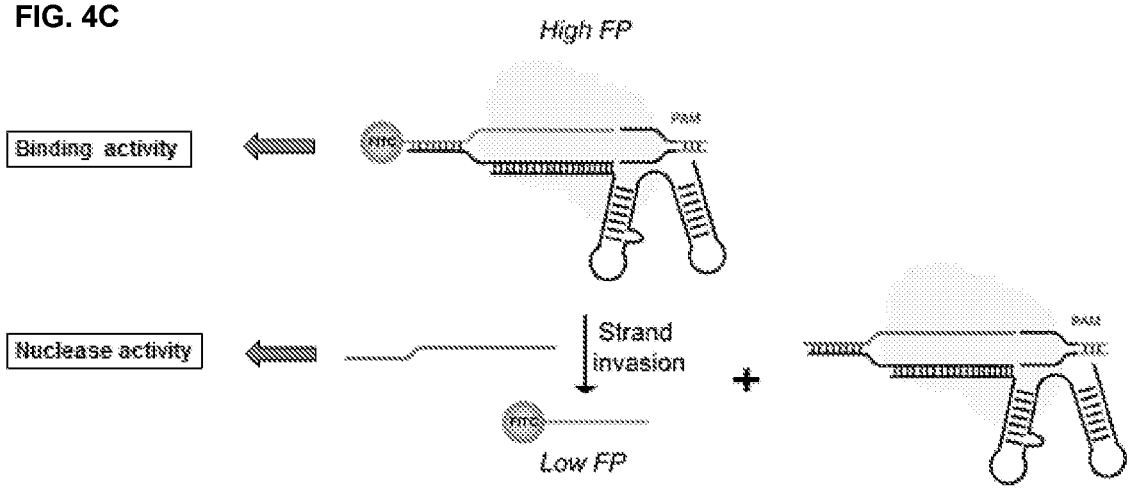
FIG. 4C is a schematic depicting measurement of Cas9 nuclease activity by strand invasion.

To assess the generalizability of our assay, it was assessed whether the activities 3 different Cpf1 orthologs—*Acidaminococcus* sp. Cpf1 (AsCpf1), *Lachnospiraceae bacterium* ND2006 Cpf1 (LbCpf1), or *Francisella tularensis* subsp. *novicida* Cpf1 (FnCpf1) could be sensitively detected. In general, the Cpf1 orthologs had lower cleavage efficiency compared to the Cas9 nucleases, as was previously reported (Kim, 2016), although nanomolar detection was observed (FIGS. 4A-4C). Of the orthologs tested, FnCpf1 exhibited the widest dose response range with similar activity for the two target sites tested (FIG. 4C). While successful inhibition of fluorescence was observed for both AsCpf1 and LbCpf1, their efficiencies were much lower than FnCpf1, SpCas9, or SaCas9, and required >200 fold excess protein to detect cleavage of 0.1 nM DNA (FIGS. 4A-4B). Interestingly, each Cpf1 ortholog yielded different activity depending on the gRNA site, with the installed distal PAM site generally being active toward all Cpf1s tested. LbCpf1 was not able to cleave the endogenous TTTC PAM site, but was very active toward the distal site PAM (FIG. 4B). This trend of activity was reversed for AsCpf1, although it was capable of cleaving both targets (FIG. 4A). In all cases, denaturing gels confirmed the expected sizes of gRNAs and crRNAs.

EGFP Disruption Assay

Figure 3K:
FIG. 3K is a schematic depicting an EGFP-disruption assay in U2OS.EGFP cells.
Figure 3L:
FIG. 3L depicts the results of an EGFP knockdown experiment, showing images corresponding to Control EGFP-disruption assay (left panel); EGFP-disruption assay—Cas9 (center panel); and EGFP-disruption assay—Cas9+BRD2940. EGFP knockdown using SpCas9 led to loss of fluorescence, which was recovered by the compound BRD2940.
Figure 3M:
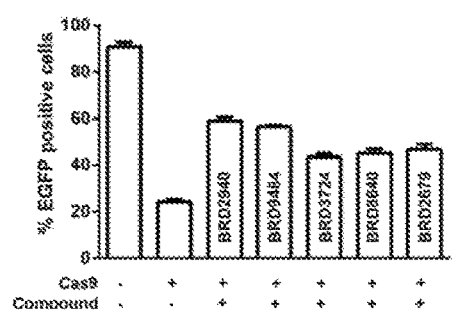
FIG. 3M is a graph showing testing of compounds identified by the FP-assay in the EGFP-assay
Figure 3N:
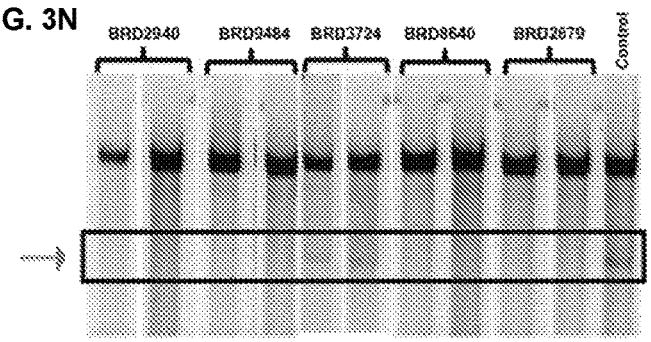
FIG. 3N depicts the results of a Surveyor assay in the absence (left lanes) or presence (right lanes) of compounds identified by the FP-assay. The Surveyor fragment was absent in compound treated cells but present in control assays. The results of the Surveyor assay confirmed Cas9 inhibition by the FP-assay hit compounds. Exemplary data are shown of assay performed in replicate.

Joung and co-workers (Fu et al., *Nat Biotechnol* 2013, 31, 822-6; Kleinstiver et al., *Nature* 2015, 523, 481-5) have reported a U2OS.EGFP cell line wherein knockdown of EGFP gene by leads to loss of EGFP fluorescence (FIGS. 3K and 3L). By quantifying the percentage of EGFP positive cells using flow cytometry, one can estimate SpCas9 activity. The low throughput, flow cytometry-readout was replaced with a high-throughput readout using a high-content, automated microscope imaging. This assay can be run in a 96-well format and the data can be analyzed by a high-throughput image analysis platform, called ImageExpress. A 70-80% reduction in EGPF positive cells was observed upon SpCas9 mediated knockdown. Further, it was found that most of FP-assay "hits" inhibited SpCas9 in cells, as the compound-treated cells did not lose EGFP fluorescence (FIG. 3M). It has been confirmed that these "hits" are active in the Surveyor assay, which is considered to be the gold standard for Cas9 activity in cells, but is highly tedious and low-throughput. These compounds successfully inhibited indel formation in the EMX1 gene in HEK293T cells (FIG. 3N) at 10-20^M of compound concentration.

Strand Invasion Assay

To measure the Cas9 nuclease activity, a technique was designed based on DNA strand invasion. It was hypothesized that, after a DSB by Cas9 on the substrate DNA, the fluorophore labeled (FAM) 5'-end of the non-target strand can be replaced by a corresponding single-stranded cold DNA (FIG. 4B). Without being bound by theory, the displacement of the cleaved fluorophore labeled 5'-end by cold DNA leads to the loss of fluorophore from the Cas9:gRNA-DNA ternary complex which results in a decrease in the fluorescence polarization signal (FIG. 4C). Thus, the extent of loss in the fluorescence polarization signal provides a readout of the Cas9 nuclease activity. It is anticipated that this assay would be useful to evaluate the potency of a Cas9 inhibitor.

Figure 4D:
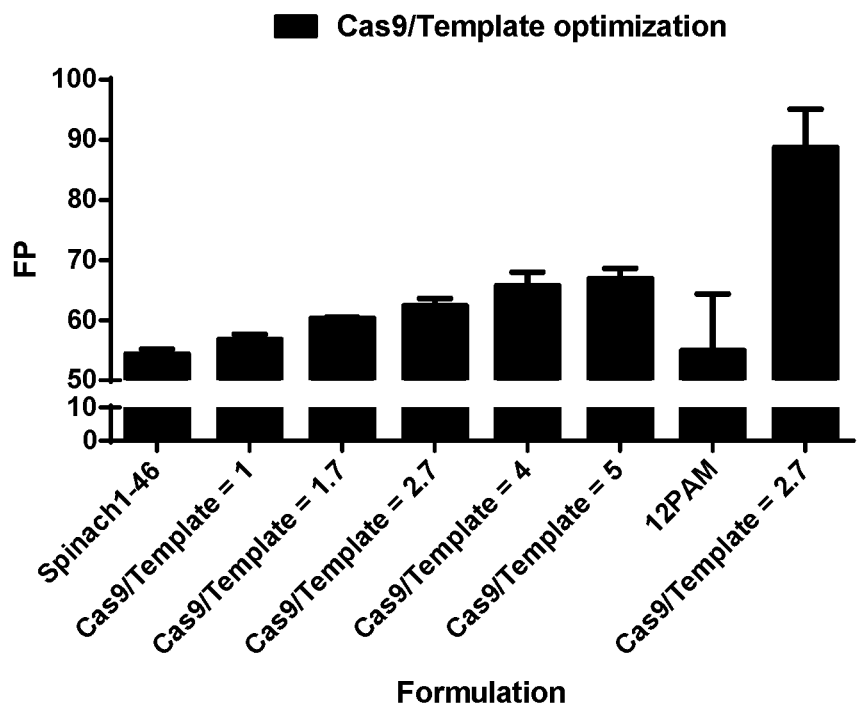
FIG. 4D is a graph depicting optimization of Cas9: Substrate ratio in the fluorescence polarization-based strand invasion assay. Data columns corresponding to the 12PAM DNA template were included as positive control.
Figure 4E:
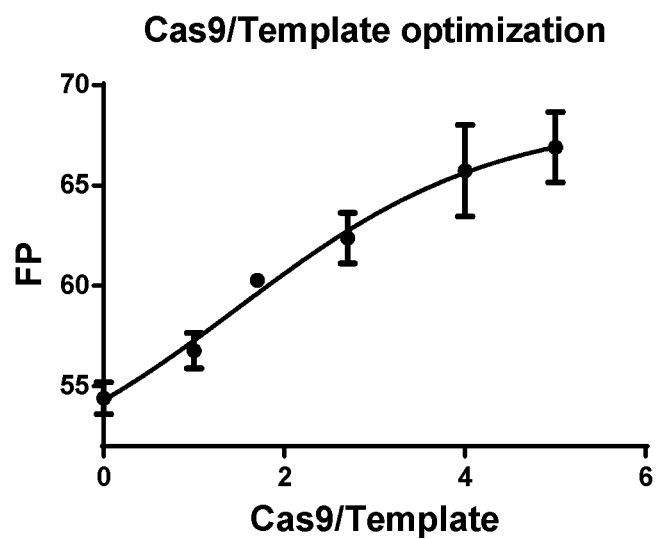
FIG. 4E is a graph depicting optimization of Cas9: Substrate ratio in the fluorescence polarization-based strand invasion assay.
Figure 4F:
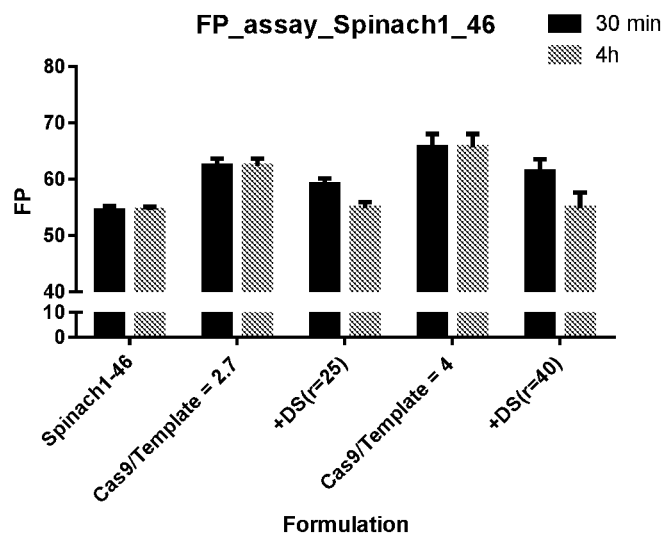
FIG. 4F is a graph depicting fluorescence polarization (FP) in the Cas9 strand invasion assay. The results validate the strand invasion experiment.
Figure 4G:
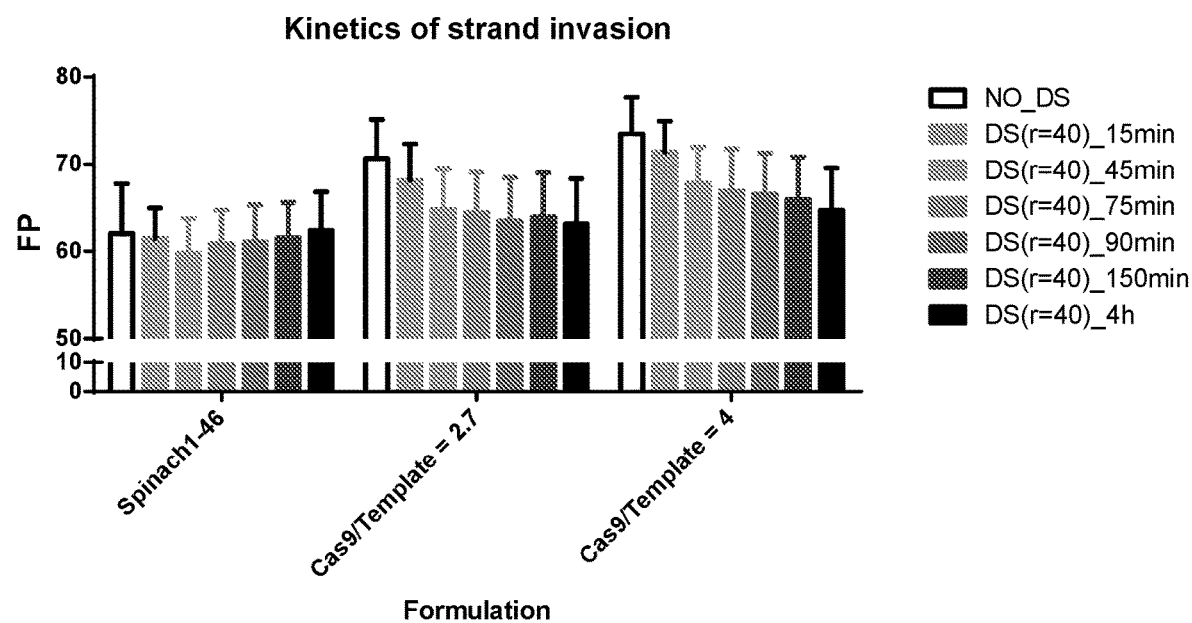
FIG. 4G is a graph depicting kinetics of strand invasion in the Cas9 strand invasion assay. The results validate the strand invasion experiment.

Initially, performed a fluorescence polarization assay was performed with increasing concentration of Cas9:gRNA keeping the substrate DNA concentration constant and a dose curve was generated (FIGS. 4D and 4E). From the dose curve two RNP:DNA ratios were picked below the saturation point and the displacement assay was performed. While binding of Cas9/gRNA with DNA template enhanced the fluorescence polarization value, addition of excess unlabeled DNA corresponding to the 5'-end revert back the signal in a time dependent manner (FIGS. 4F and 4G). Moreover, addition of the excess cold DNA to the substrate DNA did not affect its FP value indicating a lack of interference with the assay. These results indicated that, Cas9 nuclease activity can be followed up using this fluorescence polarization based strand-invasion assay. It is anticipated that, the strand-invasion assay can be used to screen Cas9 inhibitors in a high throughput manner.

Strand Displacement Assay.

Figure 5A:
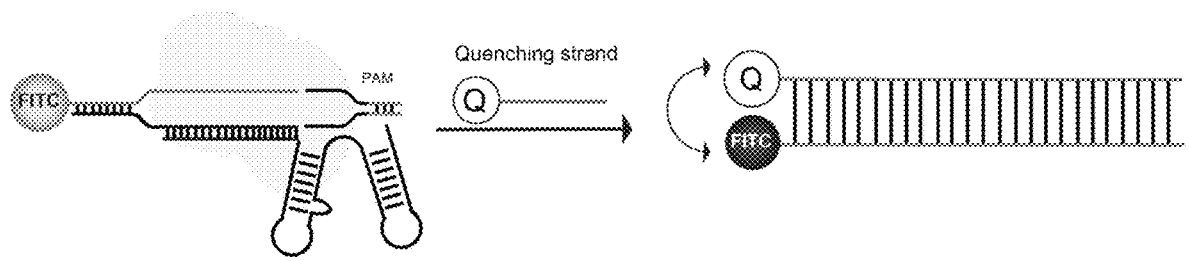
FIG. 5A is a schematic depicting a fluorescence quencher based Cas9 strand invasion assay.
Figure 5B:
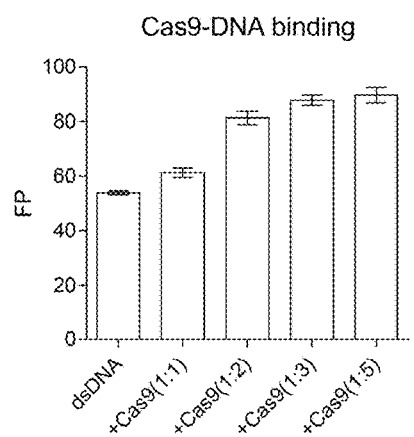
FIG. 5B is a graph showing Cas9-DNA binding in the fluorescence quencher based Cas9 strand invasion assay.
Figure 5C:
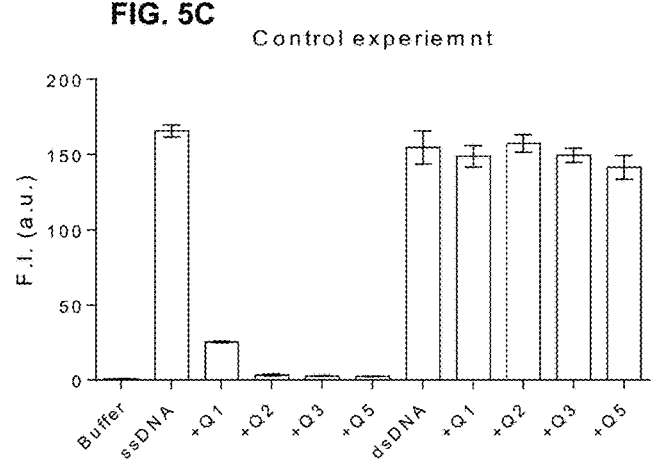
FIG. 5C is a graph showing that the 3'-quencher-DNA strand efficiently diminished FAM fluorescence only in the ss-non-target DNA in a ratiometric fashion while there was no effect on the ds-target DNA in the fluorescence quencher based Cas9 strand invasion assay.
Figure 5D:
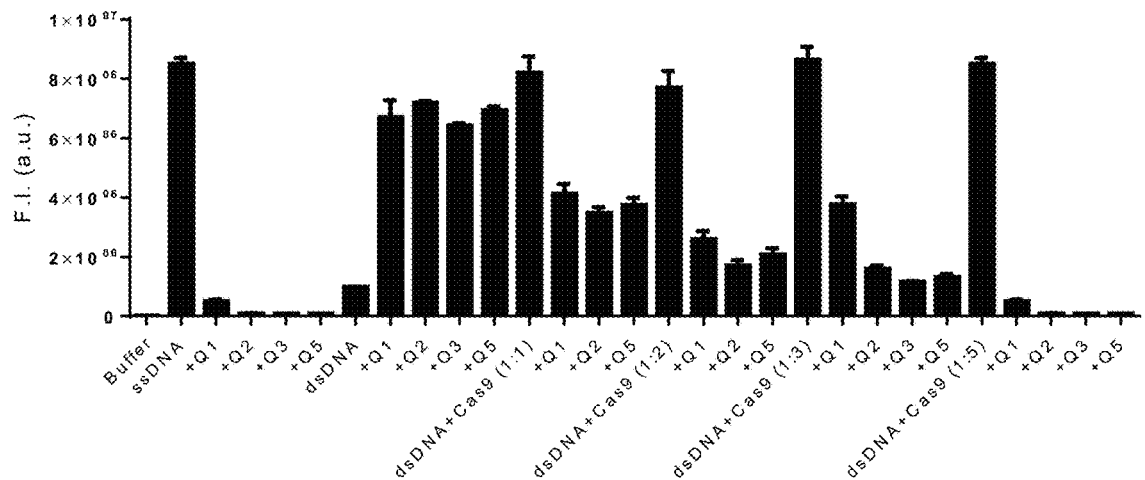
FIG. 5D is a graph showing systematically enhanced readout was observed with increasing quencher concentration in different Cas9 compositions in the fluorescence quencher based Cas9 strand invasion assay.
Figure 5E:
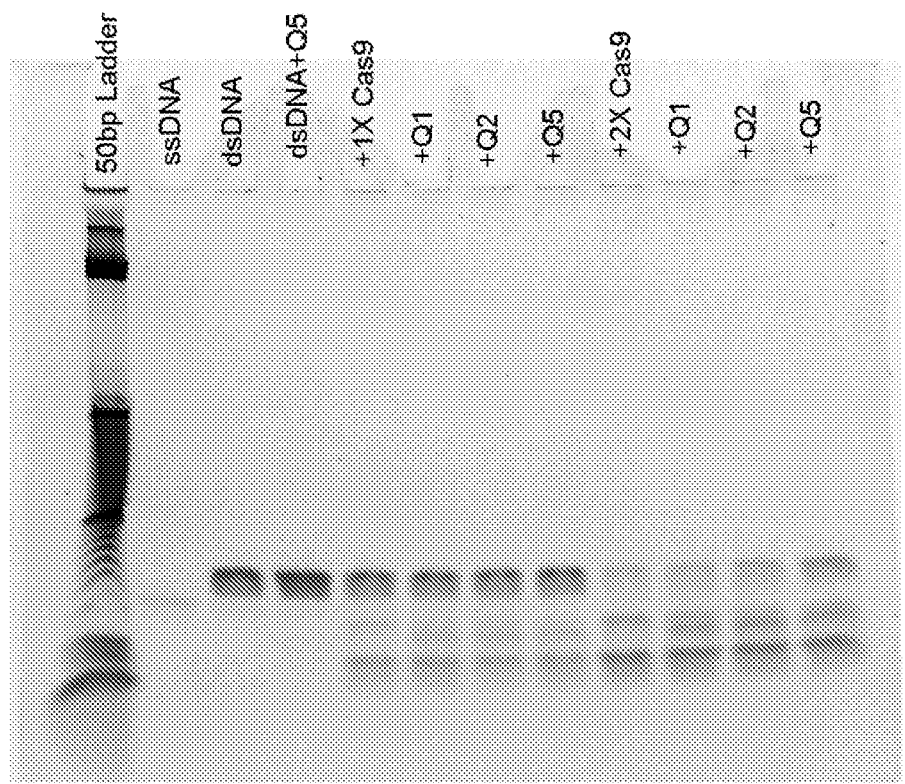
FIG. 5E depicts gel electrophoresis results of the fluorescence quencher based Cas9 strand invasion assay showing that DNA fragments were generated in the presence of Cas9.

In another approach, the previously described strand invasion assay was modified to make it more sensitive and effective with an orthogonal readout of fluorescence instead of fluorescence polarization. In this assay, the substrate DNA remained the same as the strand invasion assay, though the sequence of the invading cold DNA was changed in such a way that it can hybridize with the 5'-end free DNA available only after the Cas9 mediated cleavage. Moreover, the DNA strand was conjugated with a fluorescence quencher at the 3'-end which can readily quench FAM fluorescence only when it hybridizes with the labile non-target strand (FIG. 5A). As a proof of principle, the DNA strand bearing a quencher on the 3'-end was incubated with both ds-target DNA and ss-non-target DNA and the fluorescence signal measured. It was found that the 3'-quencher-DNA strand efficiently diminished the FAM fluorescence only in the ss-non-target DNA in a ratiometric fashion while there was no effect on the ds-target DNA (FIGS. 5B and 5C). Based on these result, fluorescence quencher based strand displacement technique was applied to measure Cas9 nuclease activity in a biochemical setup. Upon addition of the quencher strand into the Cas9 reaction, a significant drop in the FAM fluorescence signal was observed. Without being bound by theory, this indicated formation of FAM-quencher DNA duplex with the nicked non-target strand. The phenomenon was validated in different Cas9 compositions with increasing quencher concentration and a systematically enhanced readout was observed (FIG. 5D). To further confirm that the fluorescence signal drop was due to the Cas9 cleavage and FAM-quencher DNA duplex formation, the samples were analyzed by gel electrophoresis (FIG. 5E). The gel electrophoresis results showed the appearance of two cleaved DNA fragments in presence of Cas9. Moreover, upon introduction of the quencher strand, a clear disappearance of the larger DNA fragments corresponding to the 5'-end cleaved product could be observed while a new band appeared. Without being bound by theory, the appearance of the new band was due to the FAM-quencher DNA duplex formation. These results confirmed this design strategy can quantitatively detect Cas9 cleaved DNA product and hence provide a way to measure Cas9 activity.

Figure 1E:
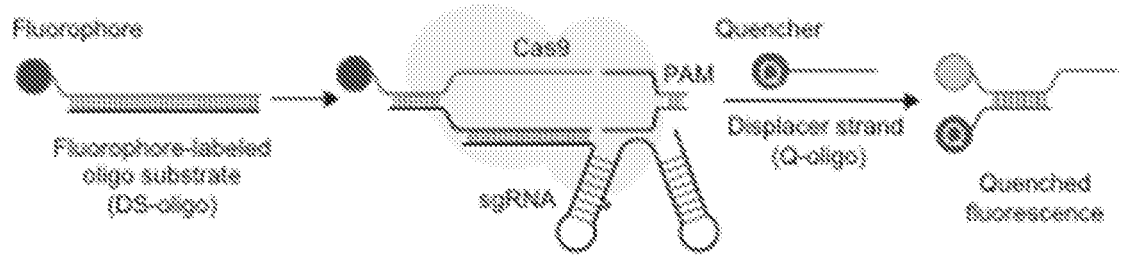
FIG. 1E is a schematic of a fluorescence-based strand displacement assay for monitoring Cas9 nuclease activity. Following Cas9 cleavage, a fluorophore bearing double stranded oligo (DS-oligo) is displaced by a quencher (Q)-bearing displacer strand (Q-oligo), resulting in a decrease in fluorescent signal.
Figure 1F:
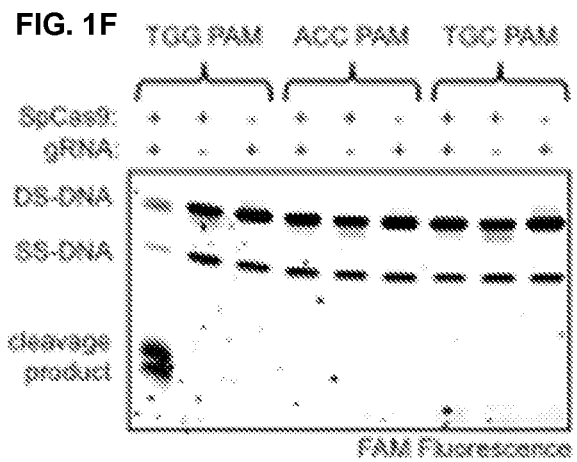
FIG. 1F depicts gel-monitored cleavage of fluorophore labeled oligos. Fluorophore labeled oligos (100 nM) were cleaved by SpCas9 (500 nM) in a PAM-dependent manner. Gel is representative of 2 biological replicates.

Although SpCas9 binds to its DNA substrate with nanomolar affinity, even following double stranded cleavage, it was discovered that of the 4 resulting DNA fragments, the distal non-target strand is weakly held, and can be displaced upon addition of excess complementary single stranded DNA (Richardson, 2016) (FIG. 1E). In this system, the 5' end of the non-target strand is fluorescently labeled, and the fluorescence is quenched in a cleavage-dependent manner by adding in excess a complementary DNA strand labeled with a 3' quencher. Upon displacement and annealing of the two strands, fluorescence is quenched by a FRET mechanism, thereby providing a proxy measurement for Cas9 activity at the RuvC domain based on the extent of fluorescence loss. Double stranded oligos (DS-oligo) labeled with 6-carboxyfluorescein were generated containing either a TGG PAM motif for recognition by SpCas9, or ACC and TGC PAMs that should not be recognized by SpCas9 (Table 2). Cleavage of DS-oligo substrate oligos by SpCas9:gRNA was verified by monitoring the FAM fluorescence in a denaturing gel (FIG. 1F), validating the PAM dependence on activity.

Figure 1G:
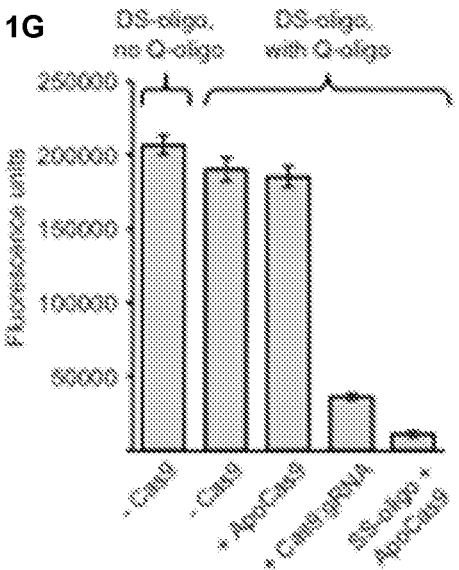
FIG. 1G is a graph showing that DS-oligo fluorescence is not quenched in the presence of Q-oligo unless the duplex is disrupted by cleavage via an active Cas9:gRNA complex. A single DNA strand with fluorophore (SS-Oligo) can be completely quenched by the Q-oligo in the absence of a duplex. Error bars represent standard deviation from 3 technical replicates (n=3), and is representative of 2 biological replicates.
Figure 1H:
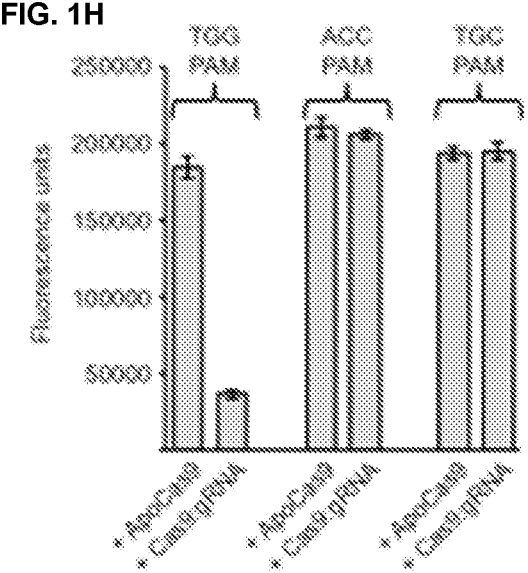
FIG. 1H is a graph showing that quenching via strand displacement is dependent on the presence of a NGG PAM in the DS-oligo when using SpCas9, indicating the specificity of the interaction. Error bars represent standard deviation from 3 technical replicates (n=3), and is representative of 2 biological replicates.
Figure 1I:
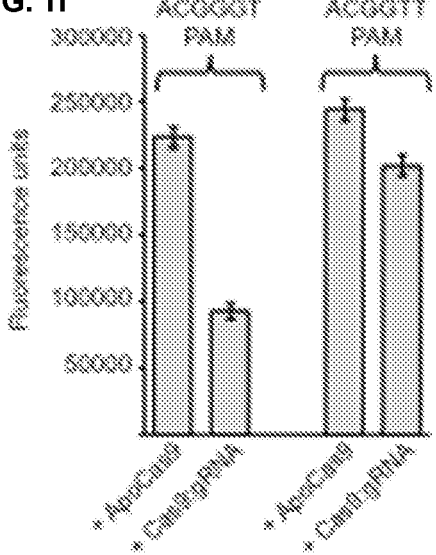
FIG. 1I is a graph showing that strand displacement is generalizable to SaCas9. SaCas9 strand displacement had comparable efficiency to SpCas9, and was dependent on an NNGGGT PAM sequence. Error bars represent standard deviation from 3 technical replicates (n=3), and is representative of 2 biological replicates.

An oligo complementary to the 5'-end of the non-target strand was generated, containing an Iowa-Black FQ quencher on the 3' terminus (Q-oligo) (Table 2). Excess Q-oligo (5 nM) could not disrupt the fluorescence of duplex DS-oligo (1 nM), but was capable of quenching the FAM-labeled strand outside of a duplex (SS-oligo, 1 nM). When SpCas9:gRNA complex (5 nM) was added, a significant loss of fluorescence was observed. This activity was dependent on gRNA-mediated cleavage of DNA and not local DNA melting caused by Cas9 binding to the PAM motif, as addition of ApoCas9 to DS-oligo and Q-oligo did not result in fluorescence loss (FIG. 1G). In agreement with the substrate cleavage observed via denaturing gel, strand displacement was dependent on the correct TGG PAM motif, as no quenching was observed with the ACC or TGC PAM oligos (FIG. 1H). Strand displacement is generalizable to SaCas9 with comparable efficiency to SpCas9, and is dependent on an NNGGGT PAM sequence (FIG. 1I).

TABLE 2

| Strand Displacement Assay sequences | |
| --- | --- |
| SpCas9 DNA Substrate | 5'-6-FAM/TAATACGACTCACTATAGGAC GCGACCGAAATGGTGAAGGACGGGT-3' (SEQ ID NO: 3) |
| SaCas9 DNA Substrate | 5'-6-FAM/ACTCACTATAGGGACGCGACC GAAATGGTGAAGGACGGGTCCAGTGCTTCG G-3' (SEQ ID NO: 4) |
| Cpf1 (all species) DNA Substrate | 5'-CGTCCTTCACCATTTCGGTCGCGTCCC TATAGTGAGTCGTATTAGTTCCAT/6-FAM-3' (SEQ ID NO: 5) |
| DNA Substrate | 5'-6-FAM/ATGGAACTAATACGACTCACT ATAGGGACGCGACCGAAATGGTGAAGGAC G-3' (SEQ ID NO: 6) |
| SpCas9 Quencher Strand | 5'-ATAGTGAGTCGTATTA/3IABkFQ-3' (SEQ ID NO: 7) |
| SaCas9 Quencher Strand | 5'-CGTCCCTATAGTGAGT/3IABkFQ-3' (SEQ ID NO: 8) |

TABLE 2-continued

Strand Displacement Assay sequences

| | |
|---|---|
| Cpf1 (all species) Quencher Strand | 5'-5IABkFQ/ATGGAACTAATACGAC-3' (SEQ ID NO: 9) |
| Quencher Strand | 5'-GTCGTATTAGTTCCAT/3IABkFQ-3' (SEQ ID NO: 10) |

DNA substrates for the strand displacement assay shown are double stranded, and only include a fluorophore (6-FAM) on the strand shown.
Quencher strand sequences for the strand displacement assay shown are single stranded, and include a quencher (Iowa Black® FQ).

Figure 1J:
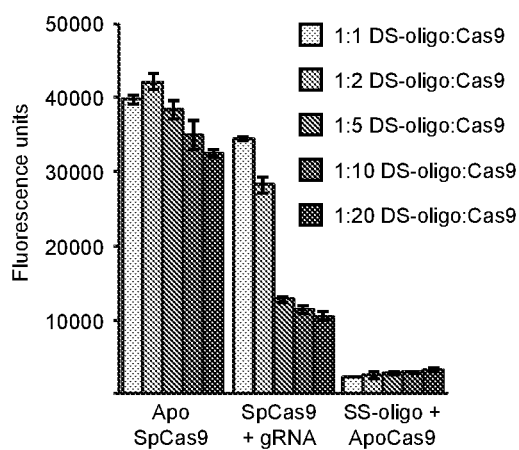
FIG. 1J is a graph depicting optimization of the relative ratio of the SpCas9:gRNA complex (1-200 nM) to DS-oligo (fixed at 1 nM) while holding the Q-oligo concentration fixed (5 nM). Using a 5-fold excess of SpCas9:gRNA maximizes activity while minimizing background quenching from SpCas9 simply binding to DNA. Data is presented as the average background-subtracted fluorescence from 3 technical replicates. Error bars represent standard deviation (n=3).
Figure 1K:
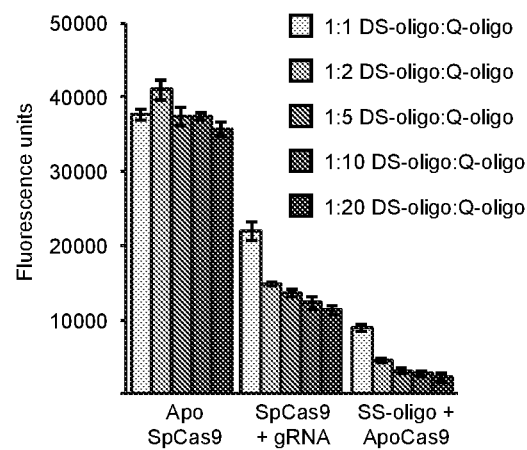
FIG. 1K is a graph depicting optimization of the relative amounts of Q-oligo (1-200 nM) and DS-oligo (fixed at 1 nM) while holding the SpCas9:gRNA concentration fixed (5 nM). A 2-fold excess of Q-oligo is sufficient to displace the cut strand. Data is presented as the average background-subtracted fluorescence from 3 technical replicates. Error bars represent standard deviation (n=3).
Figure 1L:
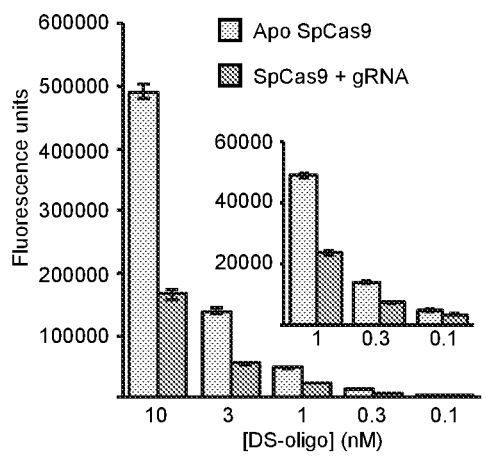
FIG. 1L is a graph depicting a determination of the DS-oligo limit of detection, fixing [SpCas9] and [Q-oligo] at 5-fold relative amount of DS-oligo and conducting the reaction for 120 min. Data is presented as the average background-subtracted fluorescence from 3 technical replicates, and is representative of 2 biological replicates. Error bars represent standard deviation (n=3). Inset is enlarged view of the 1, 0.3, and 0.1 nM points.
Figure 1M:
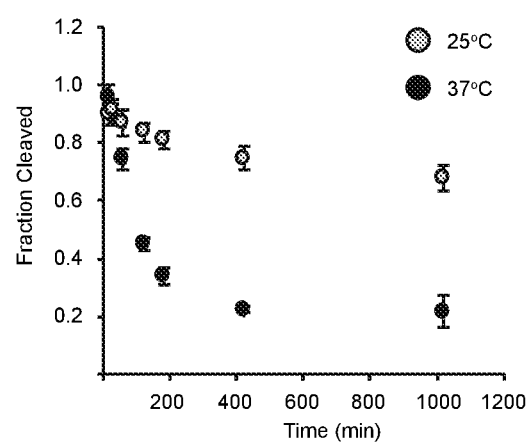
FIG. 1M is a graph depicting a time course of strand displacement, fixing [SpCas9] and [Q-oligo] at 5-fold relative amount of DS-oligo (1 nM). Reactions were incubated at either 25° C. or 37° C. Data is presented as fraction with 3 technical replicates, and is representative of 2 biological replicates. Error bars represent standard deviation (n=3).

The ratio of Q-oligo and Cas9:gRNA to the DS-oligo substrate was characterized by testing relative ratios of 1:1, 1:2, 1:5, 1:10, and 1:20, and found that a 5-fold excess of each reagent relative to DS-oligo is sufficient to yield maximum quenching (FIGS. 1J and 1K). Using these optimized conditions, the assay was capable of detecting low (<5 nM) nanomolar quantities of SpCas9 (FIG. 1L). Optimizing the kinetics of this assay showed that 2.5 hours was sufficient to see >80% quenching at 37° C. (FIG. 1M). In agreement with previous reports, SpCas9 activity at room temperature was very weak although observable using our strand displacement assay (FIG. 1M). Thus, the assay provides a sensitive, specific, and potentially high-throughput readout of SpCas9 nuclease activity, at least as it pertains to the RuvC nuclease domain.

Encouraged by the success at assessing SpCas9 activity, the assay scheme was applied to other CRISPR nucleases. It was possible that such generalizability might be hindered by lack of detailed studies on the catalytic mechanisms of Cas9-nucleases from other classes and bacterial species. However, given the similarities between *Staphylococcus aureus* Cas9 (SaCas9) and SpCas9 protein fold and modes of DNA substrate binding, SaCas9 strand displacement was tested to see if it would proceed in the same manner. Using FAM-labeled oligos containing an SaCas9-recognizable ACGGGT PAM and a ACGGTT non-target PAM (ref Friedland 2015) with the appropriate Q-oligo, PAM- and Cas9:gRNA-dependent loss of fluorescence was observed (FIG. 1I) with similar efficiencies and detection limits as SpCas9. Similar results were observed with Cas nucleases of the Cpf1 family, particularly FnCpf1.

Figure 3O:
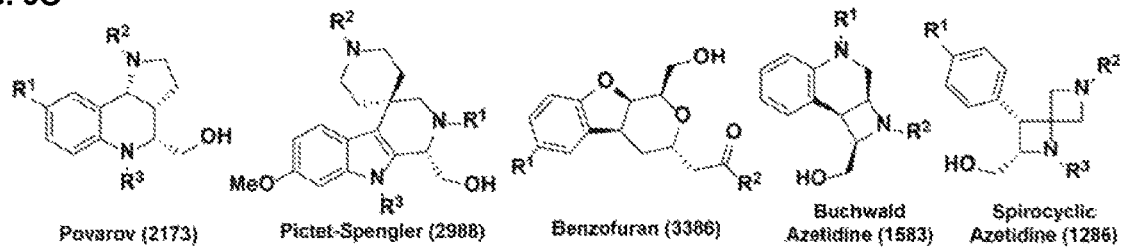
FIG. 3O depicts selected compound libraries identified as having Cas9 inhibitory activity. The selected compound libraries are used to optimize the potency of Cas9 inhibitors. Number of compounds available in each library is shown in parenthesis.
Figure 3P:
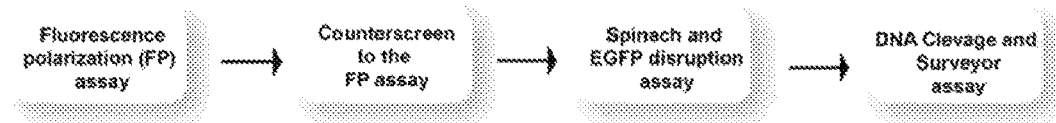
FIG. 3P is a workflow for optimization of the potency of the Cas9 inhibitors. Workflows comprise one or more of the Fluorescence polarization (FP) assay; a counterscreen to the FP assay to identify false positive results; Spinach assay; EGFP disruption assay; DNA cleavage assay and/or Surveyor assay.
Figure 3Q:
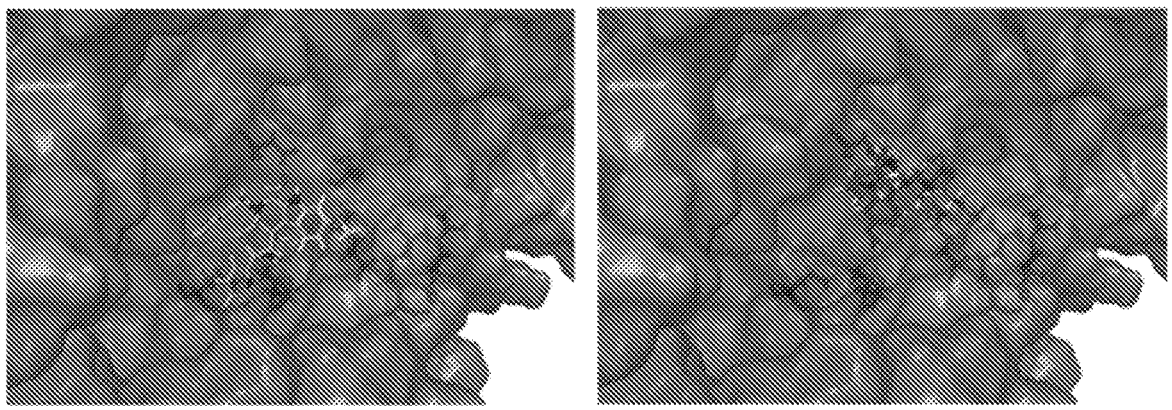
FIG. 3Q are images depicting surface-show of the binding pose for two selected Cas9 inhibitors with a Pictet-Spengler scaffold determined by Glide docking.
Figure 3R:
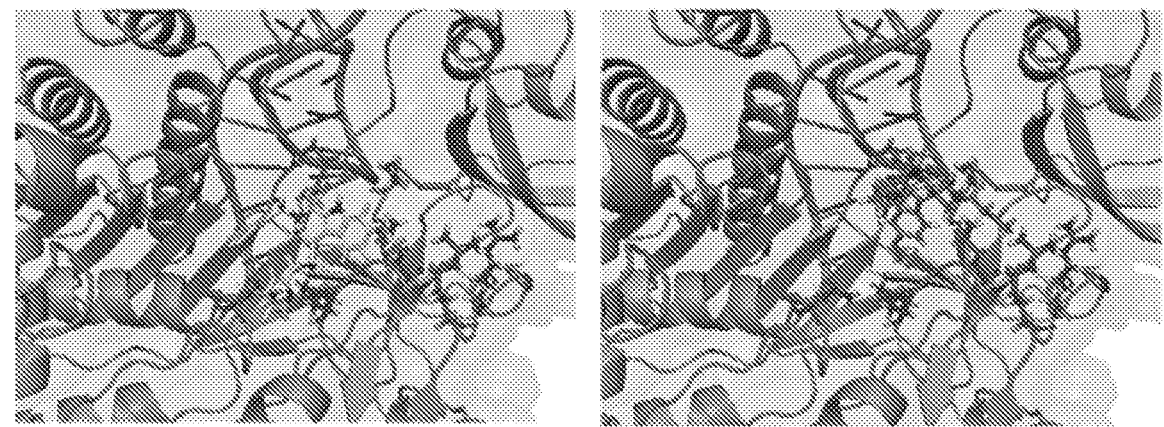
FIG. 3R are images depicting ribbon-show of the binding pose for two selected Cas9 inhibitors with a Pictet-Spengler scaffold determined by Glide docking.

Example 3. Identification of Small Molecule Inhibitors Using Assays for Detection of RNA Guided Endonuclease Activities Using the primary screening assay (FP-assay) (FIG. 1A) and multiple secondary assays (e.g., DNA cleavage, Spinach aptamer, EGFP disruption, and Surveyor assays), several SpCas9 inhibitors were identified with moderate potencies in biochemical ($IC_{50}$=600 nM) and cellular assays (~10 µM). It was found that "hits" belonged to specific diversity-oriented synthesis libraries (FIG. 3O). Schrödinger software was used to perform docking of selected active Cas9 inhibitors. The calculations show that active compounds bind at a pocket proximal to the Arginine-guanine interactions which are important PAM-recognition interactions and that electrostatic and hydrogen-bonding interactions play an important role in the binding (FIGS. 3Q and 3R). Interestingly, the inactive analogs had poorer docking scores in comparison with that of the active analogs, indicating that a computational approach was able to reproduce experimental data. Importantly, the calculations were performed with relatively small computational effort (~1 CPU hr) as a result of the small number of rotatable bonds in the identified active compounds, raising the possibility of using this software for high-throughput screening of compound libraries.

Structure-activity optimizations involve synthesis and potency evaluation of the structural analogs of the "hits" in an iterative fashion. However, this iterative approach is tedious, labor intensive, expensive, and time-consuming. Conveniently, multiple analogs of the "hits" (FIG. 3O) already exist at the Broad Institute as a part of their compound library. Structure-activity optimization entails testing compounds present in the selected libraries (FIG. 3O) following the workflow described in FIG. 3P. Briefly, FP-based primary screening assay was used followed by a counter-screen assay to eliminate false positives. In the counter-screen assay, fluorophore labeled DNA template was incubated with either DMSO or compounds and the FP values measured. Thus, the counterscreen assay identified compounds that affect the fluorescence polarization of the 12PAM-DNA in the absence of [SpCas9:guideRNA] complex. Compounds that altered the fluorescence polarization signal of the fluorophore labeled DNA template was identified as false positive and subsequently removed from the data.

Figure 6A:
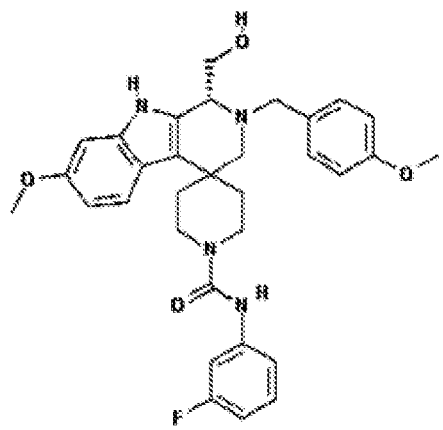
FIG. 6A depicts the chemical structure of hit compounds BRD-K33182911-001-01-8 (BRD2911); BRD-K36151368-001-01-8 (BRD1368); BRD-K86027682-001-01-8 (BRD7682); and BRD-K96745813-001-01-5 (BRD5813).
Figure 6A:
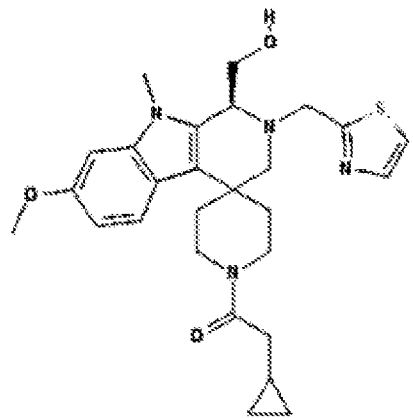
Figure 6A:
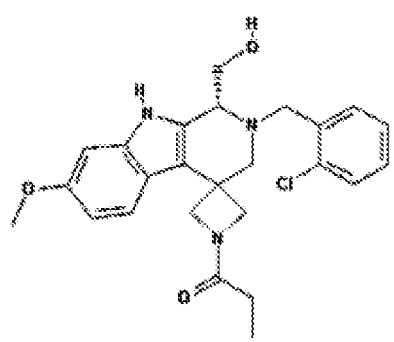
Figure 6A:
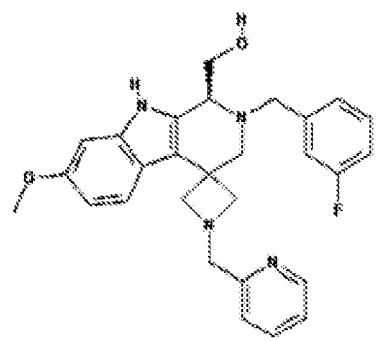
Figure 6A:
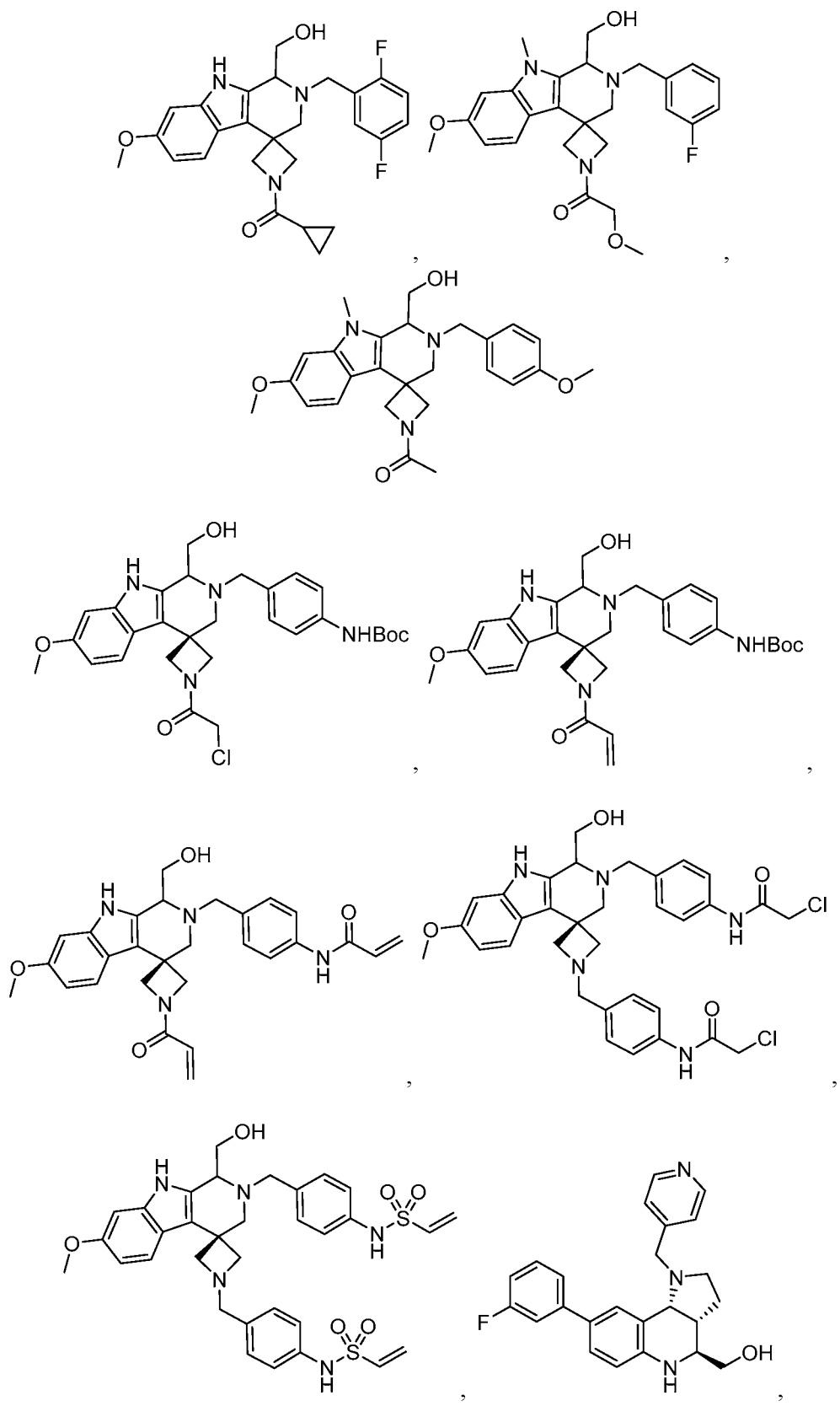
Figure 6A:
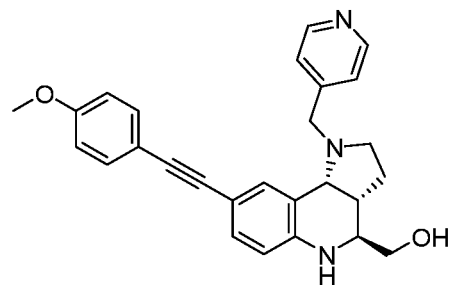
Figure 6B:
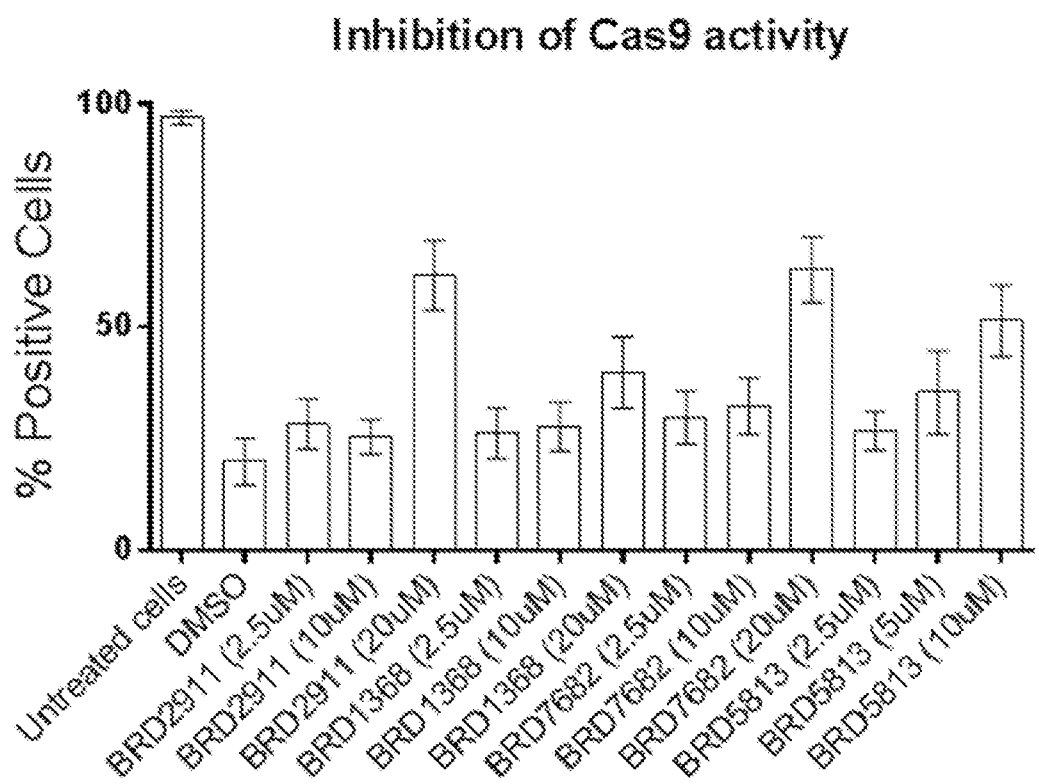
FIG. 6B is a graph depicting compound mediated inhibition of Cas9 activity in egfp-U2OS cells (48 h treatment) for the compounds shown in FIG. 5A.
Figure 6C:
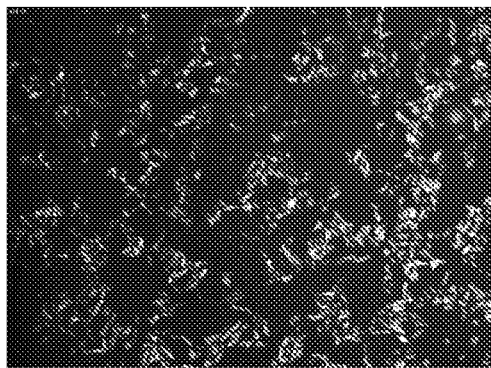
FIG. 6C are cell images for compound mediated inhibition of Cas9 activity in egfp-U2OS cells (48 h treatment) for the compounds shown in FIG. 5A.
Figure 6C:
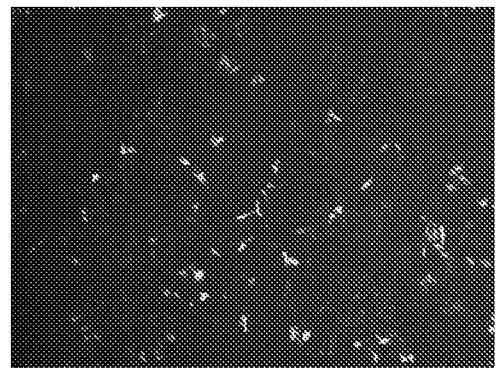
Figure 6C:
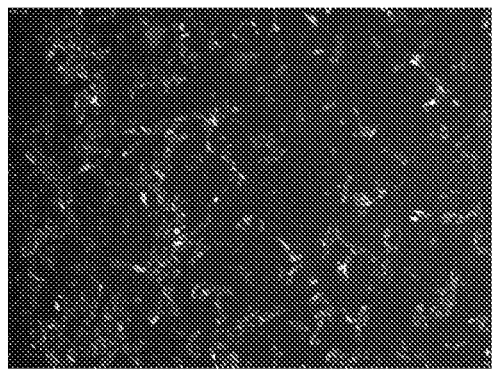
Figure 6C:
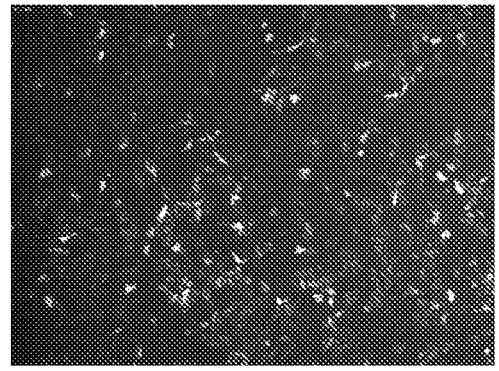
Figure 6C:
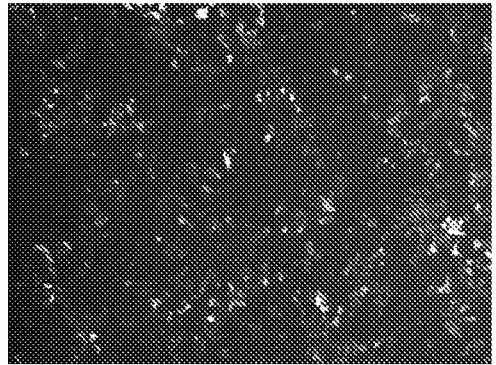
Figure 6C:
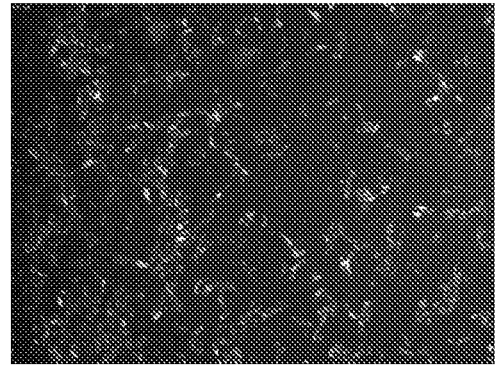
Figure 6D:
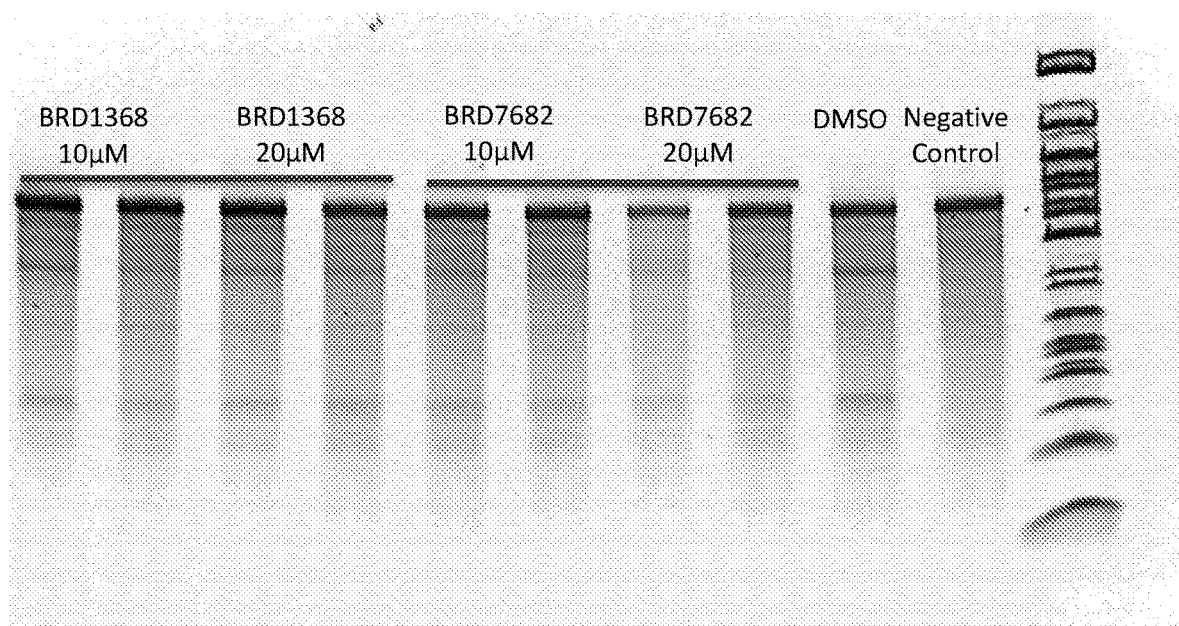
FIG. 6D are images showing compound mediated inhibition of Cas9 activity in HEK293T cells (48 h treatment) as measured by Surveyor assay for the compounds shown in FIG. 5A.
Figure 6D:
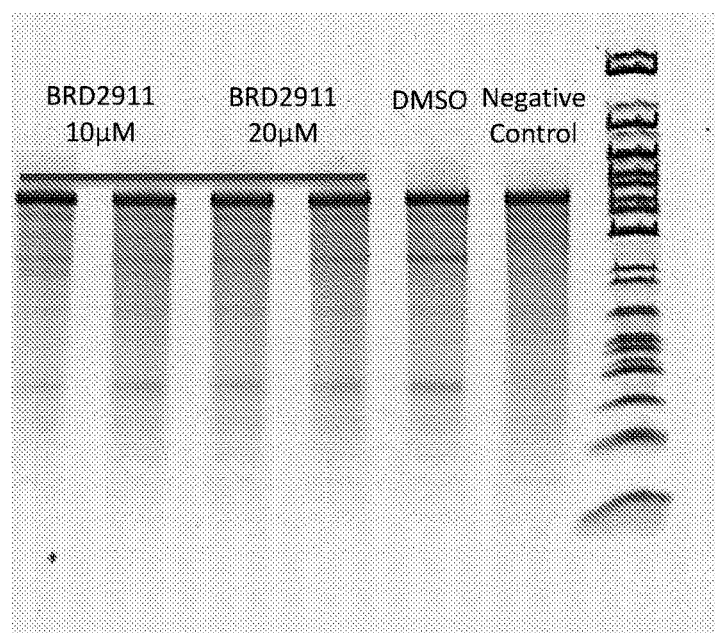

Following counter-screening, the "surviving hits" are tested using EGFP disruption assay and Spinach assay (FIGS. 6A-6C). Finally, DNA cleavage and Surveyor assay are be used to test the "hits" of the Spinach and EGFP disruption assays (FIG. 6D). The goal is to improve the current potency from 600 nM to <100 nM in the biochemical assays.

Example 4. Structure-Guided Enhancement of DNA Recognition by Cas9:gRNA Complex

Figure 7A:
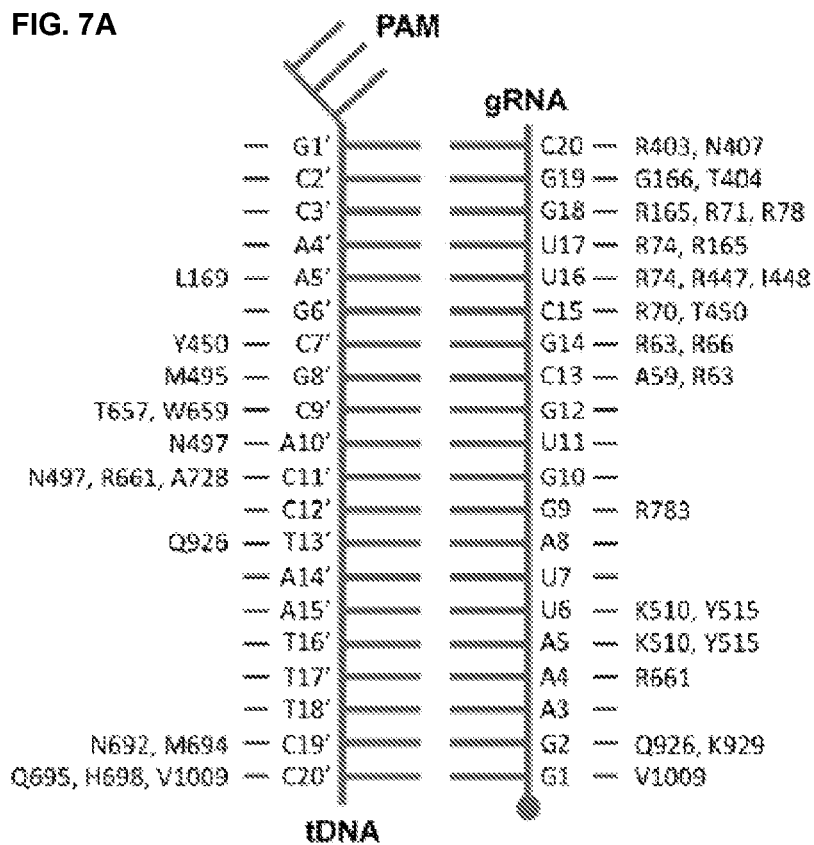
FIG. 7A is a graphical listing of Cas9 residues (PDB structure 4008) found to interact with gRNA and DNA via salt bridges, hydrogen bonds, or hydrophobic/stacking interactions.
Figure 7B:
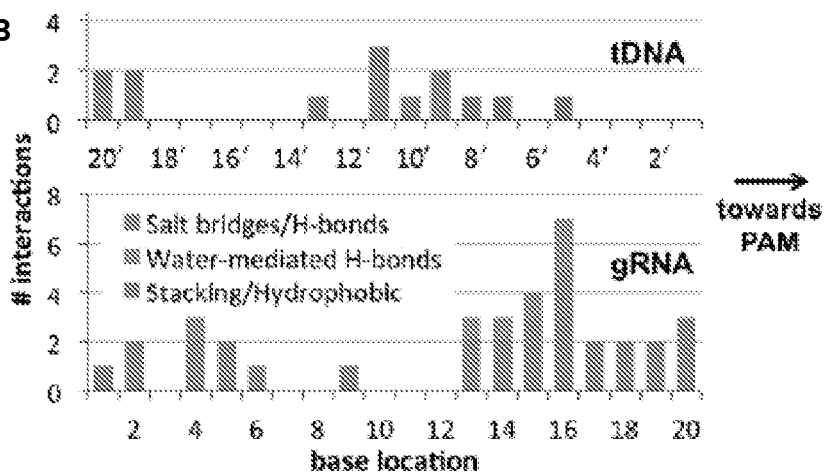
FIG. 7B is a graph representing the number of Cas9: DNA (top) and Cas9:gRNA (bottom) interactions as a function of base location.
Figure 7C:
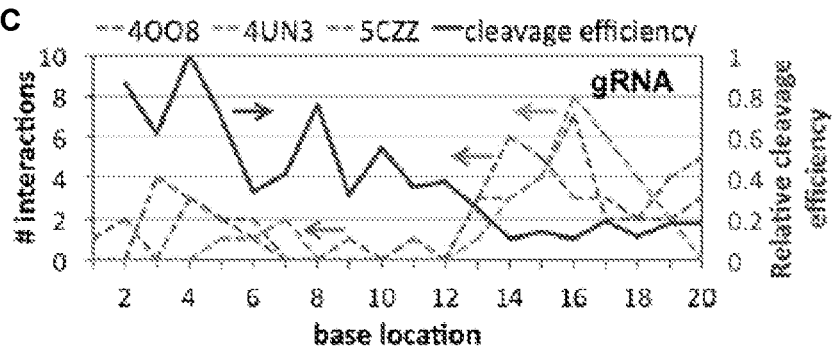
FIG. 7C is a graph depicting experimental cleavage efficiencies measured for single base pair mismatches with DNA at each gRNA base location (averaged over the 3 mismatches at each location) relative to perfectly matched DNA. The tolerance for mismatches at each base location was inversely correlated to the number of Cas9:gRNA interactions at each base location, determined from the StCas9 and two SpCas9 crystal structures.

Cas9:gRNA complex is considerably more tolerant to base pair mismatches between the gRNA and the target DNA at PAM-distal sites compared to PAM-proximal sites. To investigate the molecular basis for such a gradient in sequence specificity, the interactions of Cas9 with gRNA and with target DNA were analyzed in three different crystal structures of the ternary complex (FIG. 7A). The number of salt bridges, hydrogen bonds, water mediated hydrogen-bonds, and hydrophobic (stacking mostly) interactions were calculated as a function of base location from PAM site. A clear gradient in the total number of gRNA-Cas9 interactions with the base location was observed, with a broad stretch of strong interactions occurring at locations 1 to 8 bases from the PAM site and a smaller stretch of weak interactions at locations 14 to 20 bases away (FIG. 7B). In contrast, the DNA-Cas9 interaction profile was uniformly weak with no clear gradient across the 20-base stretch (FIG. 7B). Without intending to be bound by theory, these results indicate that Cas9 tightly contacts the gRNA portion of the RNA-DNA duplex near the PAM site while the DNA portion is contacted weakly throughout the duplex. Interestingly, the total number of interactions correlated well with the inverse of the measured tolerance for mismatches at each base location (FIG. 7C). Without intending to be bound by theory, it was hypothesized that the low sequence specificity of Cas9 at locations distant from the PAM site arises from the paucity of strong interactions holding gRNA at this distal region.

The results described herein were obtained using the following materials and methods.

Materials and Instruments

All oligos were purchased from IDT, and were either purified by HPLC for use in strand displacement assays or by desalting for use in in vitro transcription experiments. Single time point fluorescence measurements were taken using an Envision plate reader with a FITC top mirror (403), FITC 485 excitation filter (102), and BODIPY TMP FP 531 emission filter (105). Gel images were acquired with an Azure Biosystems C400 or C600.

Oligonucleotide and Plasmid Cleavage Assays

Oligonucleotides were annealed by heating to 95° C. for 5 minutes, followed by slow cooling to 25° C. at a rate of 0.1° C./sec to produce a double stranded oligo (DS-oligo). Oligo-annealing solutions were prepared by mixing 10 µM of each complementary strand together in the presence of 1× Cas9 assay buffer (20 mM Tris-HCl, pH=7.5, 150 mM KCl, 1 mM EDTA, 50 mM $MgCl_2$). A T7-promoter spinach (ref) sequence cloned into pUC57-Kan and linearized with AsiS1 was used as the plasmid substrate for Cas9 cleavage.

A Cas9:gRNA complex was first preformed by mixing each component at a ratio of 1:1.2 (Cas9:gRNA) and incubating at room temperature for 15 minutes. Cas9:gRNA complexes (500 nM) were mixed with either 100 nM of oligonucleotide or 5 nM (100 ng) of linearized plasmid in 1× assay buffer, and incubated at 37° C. for 1 hour. For oligonucleotide cleavage assays, Proteinase K (Qiagen) and RNAse (Qiagen) were added to final concentrations of 200 µg/L and 100 µg/µL, respectively, and incubated at 37° C. for at least 30 minutes. Samples were boiled in loading buffer and 50 mM EDTA for 10 min, and run on a 15% TBE-Urea gel (ThermoFisher EC68855) for 70 minutes at 200 V. FAM fluorescence was measured prior to staining with SYBR gold (ThermoFisher) to visualize total nucleotide content. For plasmid cleavage assays, loading buffer was directly added to reactions and run on 1.6-2% agarose gels with 0.01% ethidium bromide.

Fluorescence Strand Displacement Assays (SDA)

Assay components and solutions were prepared at 10× working stocks prior to mixing. Concentrations are given as the final concentrations. In a typical assay, a Cas9:gRNA complex was first formed as described above. Cas9 without gRNA (ApoCas9) was treated similarly. DS-oligo (1 nM) was mixed with quencher oligo (Q-oligo, 5 nM) in 1× Cas9 assay buffer. Reactions were initiated by addition of Cas9: gRNA (5 nM), distributed among a 384-well plate (Corning 3575) (3 technical replicates per experiment), and incubated at 37° C. for 2-3 hours. Fluorescence was read on an Envision plate reader, using 485 nm emission and 535 nm excitation wavelengths. Typical controls included replacing Cas9:gRNA with ApoCas9 (maximum possible fluorescence), replacing DS-oligo with the single stranded FAM-labeled oligo (SS-oligo, maximum possible quenching), and omitting FAM labeled oligos altogether (background fluorescence from ApoCas9 and Q-oligo). Fraction cleaved was calculated by subtracting SS-oligo controls from matched Apo-Cas9+DS-oligo and Cas9/gRNA+DS-oligo samples and normalizing to ApoCas9+DS-oligo samples.

Cas Nuclease Binding In Vitro Transcription Spinach Assay

HiScribe T7 High Yield RNA in vitro transcription kits were purchased from NEB (E2040S). The Spinach aptamer template and non-template oligonucleotides were annealed as described above. In a typical assay, a Cas9/Cpf1:gRNA complex was first formed as described above. Cas9/Cpf1 without gRNA (ApoCas9/ApCpf1) was treated similarly. A typical assay was performed by mixing the following components together from the 10× stocks to get the indicated final concentrations: NTPs (6.7 mM), 10× T7 reaction buffer (0.67×), murine RNase inhibitor (M0314L) (1.3 U), DFHBI (1 mM), DNA template (0.1 nM), and water to a final volume of 25 mL. ApoCas9 or Cas9:gRNA complexes (10×) were added to initiate cleavage and incubated at 37° C. for 30 minutes. Transcription was initiated by adding 2 mL of T7 RNA polymerase, or was omitted to assess background fluorescence. Reactions (27 µL) were transferred to a 384-well plate and the fluorescence was monitored at 37° C.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. In the case of conflict, the present specification, including definitions, will control.

What is claimed is:

1. A method of inhibiting the activity of an RNA guided endonuclease-guide RNA complex, the method comprising contacting the RNA guided endonuclease-guide RNA complex with a small molecule;

wherein the small molecule is a compound having the formula of Formula I:

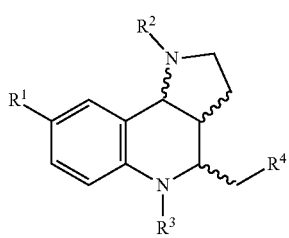

(I)

wherein $R^1$ is independently selected at each occurrence from hydrogen, —X, —R, -$L_1$-X, or -$L_1$-R; and $R_2$-$R_4$ are independently selected from hydrogen, —X, —R, -$L_1$-X, or -$L_1$-R; where X is independently selected at each occurrence from CN, OH, $CF_3$, COOH, OR, $NR_2$, or halogen;

$L_1$ is selected from —$(CH_2)_n$—, —$(CH_2)_n$—C(O)O—, —$(CH_2)_n$—C(O)—NH—, —C(O)—NH—$(CH_2)_n$—, —$(CH_2)_n$—NH—C(O)—, —$(CH_2)_n$—NH—$SO_2$—, —NH—$SO_2$—$(CH_2)_n$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —$R^L$—NH—C(O)—$(CH_2)_n$—, —$R^L$—NH—S(O)$_2$—$(CH_2)_n$—, —S—, —S(O)—, —S(O)$_2$—; wherein n is independently at each occurrence 0, 1, 2, 3, 4, 5, or 6;

$R^L$ is independently selected at each occurrence from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I; and R is independently selected at each occurrence from $C_{1-12}$ hydrocarbons, optionally substituted with one or more groups selected from CN, OH, CF, COOH, and $NH_2$, and/or with 1-10 heteroatoms selected from O, S, N, P, F, Cl, Br, I, and combinations thereof.

2. A method of inhibiting the activity of an RNA guided endonuclease-guide RNA complex, the method comprising contacting the RNA guided endonuclease-guide RNA complex with a small molecule, wherein the small molecule is a compound of Formula IA, IB, IC, or ID:

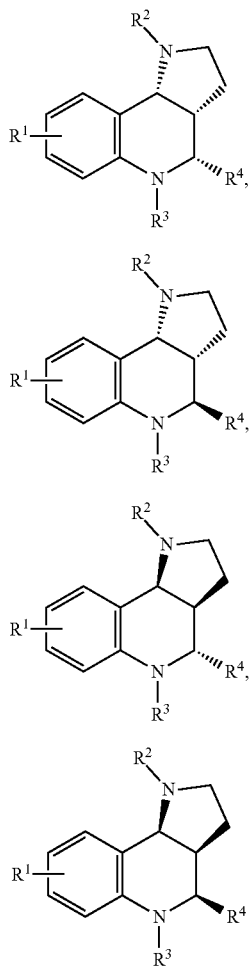

wherein $R^1$ is independently selected at each occurrence from hydrogen, —X, —R, or -$L_1$-R; and
$R^2$-$R^4$ are independently selected from hydrogen, —X, —R, or -$L_1$-R; where
X is independently selected at each occurrence from CN, OH, $CF_3$, COOH, OR, $NR_2$, or halogen;
$L_1$ is selected from —$(CH_2)_n$—, —$(CH_2)_n$—C(O)O—, —$(CH_2)_n$—C(O)—NH—, —$(CH_2)_n$—NH—C(O)—, —$(CH_2)_n$—NH—$SO_2$—, —$(CH_2)_n$—$SO_2$—NH—, —$(CH_2)_n$—$SO_2$—, —$(CH_2)_n$—$SO_2$—NH—C(O)—, —$(CH_2)_n$—$R^L$—, —$R^L$—C(O)—O—, —$R^L$—NH—C(O)—$(CH_2)_n$—, —$R^L$—NH—$S(O)_2$—$(CH_2)_n$—, —S—, —S(O)—, —$S(O)_2$—;
wherein n is independently at each occurrence 0, 1, 2, 3, 4, 5, or 6;
$R^L$ is independently selected at each occurrence from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I; and
R is independently selected at each occurrence from $C_{1-12}$ hydrocarbons, optionally substituted with one or more groups selected from CN, OH, $CF_3$, COOH, and $NH_2$ and/or with 1-10 heteroatoms selected from O, S, N, P, F, Cl, Br, I, and combinations thereof.

3. The method of claim 2, wherein the small molecule is selected from a compound having the structure

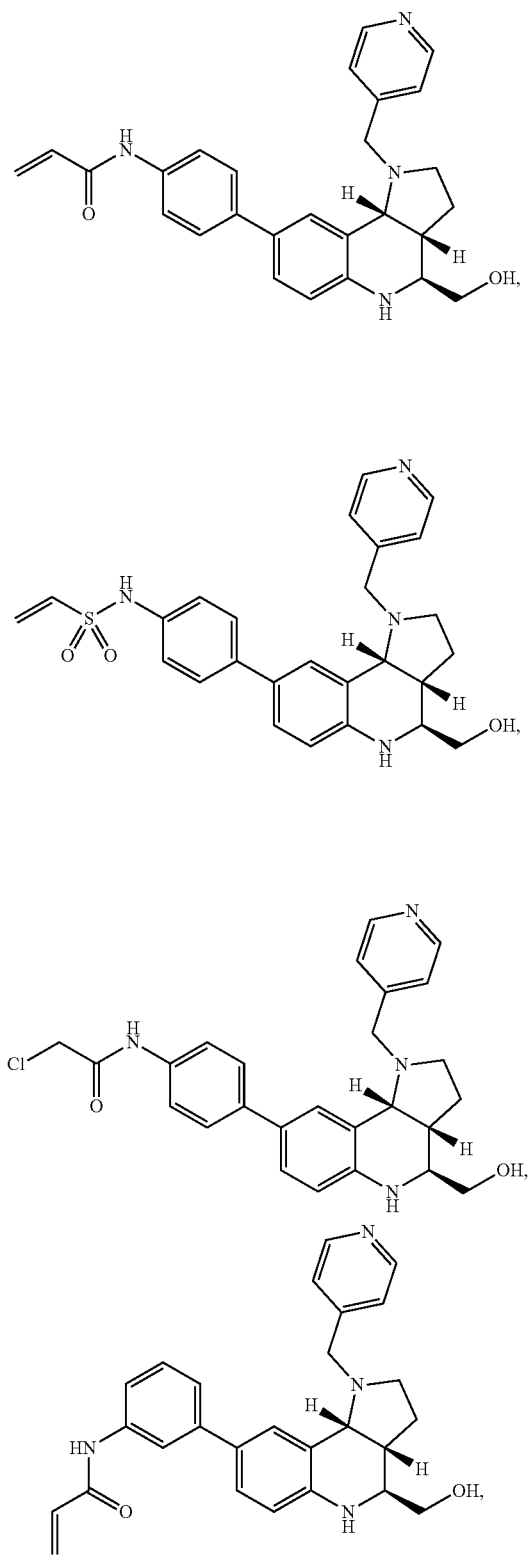

135
-continued
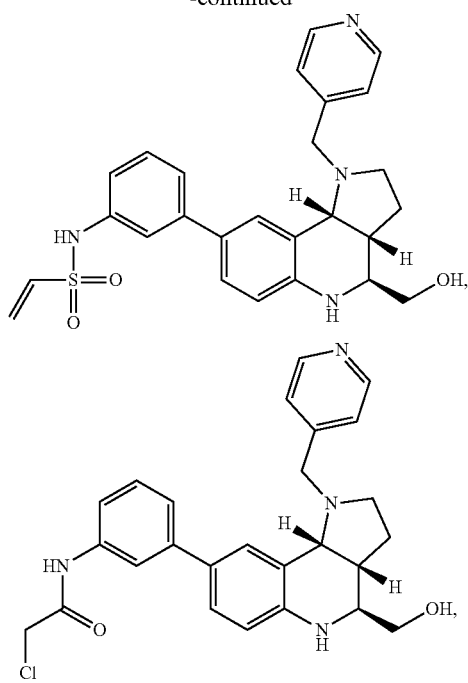
136
-continued
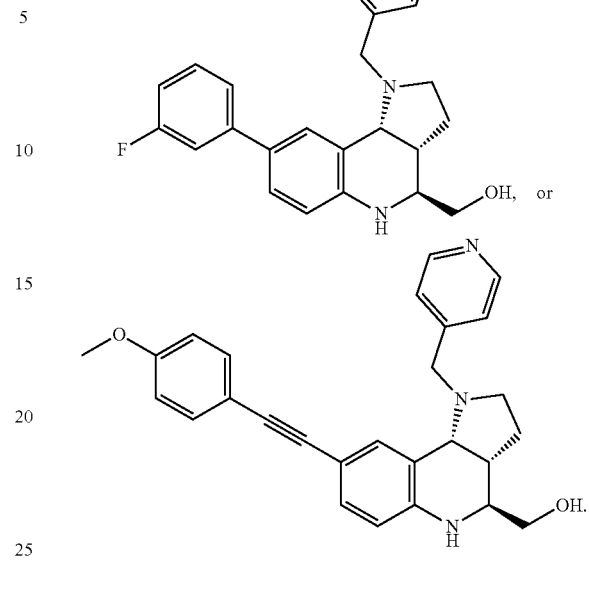
* * * * *